US007972577B2

(12) United States Patent
Horiike et al.

(10) Patent No.: US 7,972,577 B2
(45) Date of Patent: Jul. 5, 2011

(54) CHIP USING METHOD AND TEST CHIP

(75) Inventors: Yasuhiro Horiike, Tokyo (JP); Akinori Yokogawa, Kyoto (JP)

(73) Assignees: National Institute for Materials Science, Ibaraki (JP); Rohm Co., Ltd., Kyoto (JP)

( * ) Notice: Subject to any disclaimer, the term of this patent is extended or adjusted under 35 U.S.C. 154(b) by 0 days.

(21) Appl. No.: 12/707,399

(22) Filed: Feb. 17, 2010

(65) Prior Publication Data

US 2010/0158757 A1 Jun. 24, 2010

Related U.S. Application Data

(62) Division of application No. 10/595,262, filed on Apr. 3, 2006.

(30) Foreign Application Priority Data

Oct. 3, 2003 (JP) ................................ 2003-346439

(51) Int. Cl.
*B01L 3/00* (2006.01)
*C12Q 1/68* (2006.01)
*G01N 9/30* (2006.01)

(52) U.S. Cl. ............ 422/506; 422/50; 422/72; 422/500; 422/501; 422/502; 422/503; 422/504; 422/507

(58) Field of Classification Search .................... 422/50, 422/72, 99–102, 500–504, 507
See application file for complete search history.

(56) References Cited

U.S. PATENT DOCUMENTS

| | | | |
|---|---|---|---|
| 4,788,154 | A | 11/1988 | Guigan |
| 4,883,763 | A | 11/1989 | Holen et al. |
| 4,892,708 | A | 1/1990 | Wogoman |
| 6,399,361 | B2 | 6/2002 | Brotherston et al. |
| 2004/0018117 | A1 | 1/2004 | Desmond et al. |

FOREIGN PATENT DOCUMENTS

| | | | |
|---|---|---|---|
| JP | 2003-083958 | A | 3/2003 |
| JP | 2004-109082 | A | 4/2004 |
| JP | 2004-109099 | A | 4/2004 |

*Primary Examiner* — Jill Warden
*Assistant Examiner* — Dean Kwak
(74) *Attorney, Agent, or Firm* — Global IP Counselors, LLP

(57) ABSTRACT

A measuring chip is configured for separating and measuring a target component in a sample by rotation around first and second axes of rotation. The measuring chip includes a centrifugal separation tube that centrifugally separates the target component from the sample by rotating the measuring chip around the first axis of rotation; a first holding section installed in the bottom of the centrifugal separation tube, wherein non-target components other than the target component in the sample are introduced therein by rotation around the first axis of rotation, and the first holding section holds the non-target components during rotation around the second axis of rotation; and a measuring section connected to one end of the centrifugal separation tube that measures the non-target components introduced from the centrifugal separation tube by rotation around the second axis of rotation.

3 Claims, 47 Drawing Sheets

CHIP USING METHOD AND TEST CHIP

CROSS-REFERENCE TO RELATED APPLICATIONS

This application is a divisional application of U.S. patent application Ser. No. 10/595,262 filed Apr. 3, 2006, which is a national phase filing of PCT/JP2004/014988 filed Oct. 4, 2004. U.S. patent application Ser. No. 10/595,262 claims priority under 35 U.S.C. §119(a) to Japanese Patent Application No. 2003-346439 filed Oct. 3, 2003. The entire disclosures of U.S. patent application Ser. No. 10/595,262, PCT/JP2004/014988, and Japanese Patent Application No. 2003-346439 are hereby incorporated herein by reference.

TECHNICAL FIELD

The present invention relates to a method for using a chip in which a sample containing a target component has been introduced thereto, and to a test chip for testing the target component.

BACKGROUND ART

In order to diagnose hepatic and hepatobiliary disease, and alcoholic hepatopathy and to observe therapeutic processes, biochemical tests are widely carried out by sampling and measuring the concentration of enzymes in the liver, kidney, pancreas, etc., or the concentration of products thereof in the blood. Devices for conducting such biochemical tests include a blood analyzer for centrifugal separation of plasma using centrifugal force that is disclosed in Japanese Patent Application Publication No. 2003-83958. This blood analyzer performs operations in such that that it centrifugally separates serum or plasma from blood by rotating a chip with a blood sample that has been introduced therein by rotation around an axis of rotation, removing the centrifugally separated plasma from the chip by a pump means, and then introducing the plasma into an analysis tool. In another example, U.S. Pat. No. 4,883,763 discloses a sample processing card, wherein a sample is introduced into a sample measuring means via a capillary with centrifugal force by rotation around two axes of rotation, and the measured sample is then mixed with reagents. Furthermore, U.S. Pat. No. 6,399,361 discloses a micro analyzer, wherein the use of centrifugal force by rotation around an axis of rotation enables accurate measurement of biological samples, etc.

However, the blood analyzer shown in Japanese Patent Application Publication No. 2003-83958 enables the separation of plasma as a target component by using centrifugal force generated by rotation around an axis of rotation, but does not provide means for measuring the plasma after separation. Accordingly, the target component must be removed by a pump means in order to be introduced into an analyzer after separation, and therefore the sequential operations of separation, accurate measurement, etc. of the target component may not be performed within the same chip, leading to complicated processing. The sample processing card described in U.S. Pat. No. 4,883,763 removes a supernatant liquid from centrifugally separated samples using centrifugal force by means of rotation around two axes of rotation in order to extract a target component. At this point, the supernatant liquid containing the target component must be removed in a manner that enables the prevention of contamination with non-target components collected on the bottom due to centrifugal force, and thus fails to provide efficient extraction of the target component from the sample. Furthermore, the card performs the rotation around A in order to separate the target component from the non-target components, the rotation around B and A in order to measure the target component, and the rotation around B in order to mix the target component with reagents. Accordingly, switching must be performed at least three times, i.e., switching from A to B, switching from B to A, and switching from A to B, and this is complicated. Furthermore, a micro analyzer described in the U.S. Pat. No. 6,399,361 measures a centrifugally separated fluid by removing a wax valve provided in a predetermined position to make the fluid flow out. Therefore, the micro analyzer described in U.S. Pat. No. 6,399,361 needs to have a wax valve provided. In addition, the application of heat, such as with infrared rays, may be needed in order to remove this wax valve, leading to the need for complicated temperature control. Furthermore, when the melting and dissolution of the wax valve results in wax being mixed into the sample, the sample and the target component may be contaminated, disabling accurate measurement and determination of the target component.

Then, an object of present invention is to provide a test chip that enables efficient and convenient separation and measurement.

Another object of the present invention is to provide a method for using a chip having a sample containing a target component introduced therein that enables efficient and convenient separation and measurement.

SUMMARY OF THE INVENTION

In order to solve the above described problems, a first aspect of the present invention provides a measuring chip for separating and measuring a target component in a sample by rotation around a first axis and a second axis of rotation, comprising: a centrifugal separation tube for centrifugally separating the target component from the sample by rotating the measuring chip around the first axis of rotation; a first holding section provided in the bottom of the centrifugal separation tube, wherein components (hereinafter referred to as non-target components) other than the target component in the sample are introduced therein by rotation around the first axis rotation, and the first holding section holds the non-target components during rotation around the second axis of rotation; and a measuring section connected to one end of the centrifugal separation tube that measures the target component introduced from the centrifugal separation tube by rotation around the second axis of rotation.

A sample is introduced into a centrifugal separation tube, and then a target component is centrifugally separated from the sample in the centrifugal separation tube by rotating a chip around a first axis of rotation. At this point, components other than the target component in the sample (hereinafter referred to as non-target components) are introduced into a first holding section provided in the bottom of the centrifugal separation tube. Next, the target component separated by rotation around the second axis of rotation is introduced into a measuring section for measurement. In this rotation around the second axis of rotation, the non-target components introduced into the first holding section are held untreated in the first holding section. Use of the measuring chip enables collective separation and measurement of the target component in the sample, by the first axis of rotation and the second axis of rotation. Since the non-target components are held in the first holding section, in removing of the target component into the measuring section, mixing of the non-target components into the target component may be suppressed, allowing effective removal of the target component separated in the centrifugal separation tube into the measuring section. Therefore, efficient separation and efficient measurement of the target component can be realized. Furthermore, as mentioned above, since switching of the first axis of rotation to the second axis of rotation allows separation and measurement of the sample, convenient separation and measurement process can also be realized.

The measuring section has a desired volume and enables accurate measurement of a sample introduced from the centrifugal separation tube. As mentioned above, separation and measurement performed only by rotation of the chip do not need connection of the measuring chip to devices such as pumps for separation and measurement, allowing a simplified configuration of the overall device with the measuring chip to be laid thereon. Separation and measurement that can be collectively performed in one chip can enable miniaturization of the measuring chip.

Here, the measuring chip preferably includes a waste fluid reservoir connected with the measuring section, the waste fluid reservoir having a volume exceeding the volume of the measuring section in rotation around the second axis of rotation, the waste fluid reservoir preferably having a waste fluid reservoir main unit, and a waste fluid reservoir connecting section for connecting the waste fluid reservoir main unit to the measuring section, and the waste fluid reservoir main unit preferably formed in a U-shape having an opening on the side of the first axis of rotation. Target component having a volume exceeding the volume of the measuring section is introduced into the waste fluid reservoir connected to the measuring section by rotation around the second axis of rotation. Thus, the target component may be accurately measured by the measuring section. More particularly, the excessive target component that has overflowed from the measuring section is introduced into the waste fluid reservoir main unit from the measuring section, by rotation around the second axis of rotation, in order to introduce the target component into the measuring section from the centrifugal separation tube. Subsequently, the target component in the waste fluid reservoir main unit may be held untreated within the U shaped waste fluid reservoir main unit having an opening on the side of the first axis of rotation, by rotation around the first axis of rotation for removing the target component from the measuring section. Thus, backflow of the target component from the waste fluid reservoir to the measuring section may be prevented, thereby obtaining accurate measurement of the target component.

A second aspect of the present invention provides a measuring chip, wherein the centrifugal separation tube in the first aspect of the present invention is a U-shaped tube.

Since non-target components are held in the first holding section of the bottom of the U-shaped tube, and the target component is placed within the U-shaped tube during rotation around the first axis of rotation, separation of the target component from the non-target components can be realized. Next, since the non-target components are held untreated in the first holding section during rotation around the second axis of rotation, the target component located within the U-shaped tube extending to an end on the side of the measuring section and to another end in the bottom of the U-shaped tube may be effectively introduced into the measuring section. Thus, the target component in the sample may be efficiently separated.

A third aspect of the present invention provides a measuring chip, wherein an opening of the U-shaped tube of the centrifugal separation tube in the first aspect of the present invention forms an angle that is 90 degrees or less.

Since the opening of the U-shaped tube forms an angle of 90 degrees or less, the area occupied by the centrifugal separation tube on the measuring chip may become smaller.

A fourth aspect of the present invention provides a measuring chip, wherein in the first aspect of the present invention, the distance to the second axis of rotation becomes smaller as the tube extends to a second end of the centrifugal separation tube from the first end thereof connected to the measuring section.

The centrifugal separation tube is formed so that it may have a smaller distance to the second axis of rotation, as it extends to the second end from the bottom. Accordingly, by rotation around the second axis of rotation, a target component is sent in the direction of the bottom from the second end of the centrifugal separation tube. In addition, the centrifugal separation tube is formed so that the distance to the second axis of rotation will increase as it extends to the first end connected to the measuring section from the bottom. Accordingly, the target component is delivered in the direction extending to the first end from the bottom of the centrifugal separation tube by rotation around the second axis of rotation. Accordingly, by rotation around the second axis of rotation, the separated target component may be efficiently moved to the measuring section.

A fifth aspect of the present invention provides a measuring chip, wherein in the first aspect of the present invention, the distance between a first end of the centrifugal separation tube connected to the measuring section and the first axis of rotation is smaller than the distance between the second end of the centrifugal separation tube and the first axis of rotation.

Since the first end is closer to the first axis of rotation than to the second end, when centrifugally separating a sample in the centrifugal separation tube by rotation around the first axis of rotation, the sample may be prevented from being introduced into the measuring section.

A sixth aspect of the present invention provides a measuring chip, wherein the first holding section in the first aspect of the present invention has a holding section main unit, and a holding section connecting tube that connects the holding section main unit and a centrifugal separation tube, and the area of a cross-section of the holding section connecting tube is formed to be larger than the area of a cross-section of the centrifugal separation tube.

When the cross-sectional area of the holding section connecting tube is formed to be larger than the cross-sectional area of the centrifugal separation tube, air in the holding section main unit may be efficiently removed from the holding section connecting tube to the centrifugal separation tube during the introduction of a sample in the first holding section.

A seventh aspect of the present invention provides a measuring chip, wherein the first holding section in the first aspect of the present invention has a holding section main unit, and a holding section connecting tube for connecting the holding section main unit and the centrifugal separation tube, the holding section connecting tube is formed in a tubular shape, and an extension line of the tube axis of the holding section connecting tube intersects with the first axis of rotation.

Since the direction of the centrifugal force by rotation around the first axis of rotation is almost coincident with the direction of the tube axis of the holding section connecting tube, non-target components may be efficiently introduced to the first holding section from the centrifugal separation tube, leading to efficient separation of a target component and non-target components.

An eighth aspect of the present invention provides a measuring chip, wherein in the first aspect of the present invention tion, the first holding section has a holding section main unit, and a holding section connecting tube for connecting the holding section main unit and the centrifugal separation tube, the distance between the holding section main unit and the first axis of rotation is larger than the distance between the holding section connecting tube and the first axis of rotation, and the distance between the holding section main unit and the second axis of rotation is larger than the distance between the holding section connecting tube and the second axis of rotation.

Since the holding section main unit is located to be more distant from the first axis of rotation than from the holding section connecting tube, the centrifugal force works in the direction of the holding section main unit located to be more distant from the first axis of rotation than from the holding section connecting tube, by rotation around the first axis of rotation, leading to efficient introduction of non-target components into the holding section main unit. And since the holding section main unit is located to be more distant from the second axis of rotation than the holding section connecting tube, the centrifugal force works in the direction of the holding section main unit located to be more distant from the second axis of rotation than from the holding section connecting tube, by rotation around the second axis of rotation. Accordingly, non-target components introduced by rotation around the first axis of rotation are held untreated in the holding section main unit. Therefore, backflow of the non-target components from the holding section connecting tube to the centrifugal separation tube becomes difficult, guaranteeing reliable separation of the target component and the non-target components. As mentioned above, efficient introduction of only the target component to the measuring section may be attained.

A ninth aspect of the present invention provides a measuring chip, wherein the depth of the holding section main unit in the seventh or eighth invention of the present application becomes deeper as the holding section main unit separates from the second axis of rotation.

Since the depth in the holding section connecting tube, which is an entrance of the holding section main unit, is shallower, and the depth of the holding section main unit becomes deeper as the distance from the holding section connecting tube becomes larger, backflow of non-target components from the holding section main unit through the holding section connecting tube may be prevented during rotation around the second axis of rotation. The volume of the holding section main unit can be larger without enlarging the area of the measuring chip by enlarging the size only in the depth direction. Thus, miniaturization of the measuring chip can be achieved, while improving separation efficiency of the target component.

A tenth aspect of the present invention provides a measuring chip, wherein in the seventh or eighth invention of the present application, the cross-sectional area of the holding section main unit expands as the holding section main unit separates from the second axis of rotation.

Since the cross-sectional area in the holding section connecting tube, which is an entrance of the holding section main unit, is small, and the cross-sectional area of the holding section main unit becomes larger as the distance from the holding section connecting tube becomes larger, backflow of non-target components from the holding section main unit through the holding section connecting tube can be prevented during rotation around the second axis of rotation.

An eleventh aspect of the present invention provides a measuring chip, wherein the chip of the first aspect of the present invention further comprises a second holding section provided in the bottom of the centrifugal separation tube, the non-target components are introduced by rotation around the first axis of rotation, and the non-target components are held in rotation around the second axis of rotation.

The non-target components that cannot be held only by the first holding section can be held in the second holding section by further providing the second holding section. For example, even in the case where a larger amount of sample is introduced into the centrifugal separation tube, and therefore a larger amount of the non-target components are to be separated, the target component can be separated into the centrifugal separation tube by introducing a large amount of the non-target components into the first and the second holding section.

A twelfth aspect of the present invention provides a measuring chip, wherein in the first aspect of the present invention, the centrifugal separation tube has a first tube extending to the bottom of the centrifugal separation tube from a first end of the centrifugal separation tube connected to the measuring section, and a second tube extending from the bottom to a second another end, and the measuring chip further comprises a bypass tube for connecting the first tube of the centrifugal separation tube to the second tube, and a third holding section provided in the bypass tube, the non-target components being introduced by rotation around the first axis of rotation into the third holding section, the third holding section holding the non-target components during rotation around the second axis of rotation.

For example, when a large amount of sample that fills the centrifugal separation tube and the bypass tube is introduced, the non-target components are held in the third holding section connected to the bypass tube, while they are also held in the first holding section of the bottom of the centrifugal separation tube, in rotation around the first axis of rotation. Accordingly, the target component of the sample is separated in the centrifugal separation tube and the bypass tube. On the other hand, when a smaller amount of sample insufficient for filling the bypass tube is introduced only into the centrifugal separation tube, the non-target components are separated and held only in the first holding section in the bottom of the centrifugal separation tube during rotation around the first axis of rotation. Note that when the first holding section is only enlarged in order to hold a larger amount of the non-target components obtained from a larger amount of the sample, not only the non-target components but the target component will be separated into the first holding section when separating a smaller amount of the samples, decreasing the amount of the target components after separation. As mentioned above, by providing the third holding section in the bypass tube, the target component and the non-target components may be efficiently separated based on the amount of the sample.

A thirteenth aspect of the present invention provides a measuring chip, wherein in the twelfth aspect of the present invention, the distance between the connecting portion of the bypass tube to the first tube, and the first axis of rotation, is smaller than the distance between the bypass tube to a connecting portion of the second tube, and the first axis of rotation, When a sample is incorporated from an inlet connected to the second tube of the centrifugal separation tube by rotation around the first axis of rotation, the bypass tube will be filled after the interior of the centrifugal separation tube is filled. Accordingly, the bypass tube does not work for a smaller amount of the sample, but the bypass tube does work only for a larger amount of the ample.

A fourteenth aspect of the present invention provides a measuring chip, wherein in the twelfth aspect of the present invention, the bypass tube and the connecting portion of the second tube form an angle of less than 90 degrees.

Since the bypass tube is inclined with respect to the bottom of the centrifugal separation tube as mentioned above, the bypass tube will be filled after the interior of the centrifugal separation tube is filled during the incorporation of a sample from the inlet connected to the second tube of the centrifugal separation tube. Accordingly, the bypass tube does not work for a smaller amount of sample, but the bypass tube does works only for a larger amount of the sample.

A fifteenth aspect of the present invention provides a measuring chip, wherein in the first aspect of the present invention, the measuring section has a measuring section connecting tube that connects the centrifugal separation tube and the measuring section, and an extension line of the measuring section connecting tube intersects the second axis of rotation.

Since the rotation around the second axis of rotation is almost in agreement with the direction of the measuring section connecting tube, a target component may be efficiently introduced to the measuring section from the centrifugal separation tube.

A sixteenth aspect of the present invention provides a measuring chip, wherein in the first aspect of the present invention, the measuring section further has a measuring section main unit that measures the target component introduced from the centrifugal separation tube by rotation around the second axis of rotation, and the measuring section main unit has a structure formed therein.

When the target component is introduced by rotation around the second axis of rotation, surface tension works between the target component and the surface of a structure, thus enabling prevention of backflow of the target component to the centrifugal separation tube.

A seventeenth aspect of the present invention provides a measuring chip, wherein in the first aspect of the present invention, the measuring chip further comprises a regulation tube connected to the centrifugal separation tube and to the measuring section, the regulation tube serving to regulate the amount of sample centrifugally separated with the centrifugal separation tube. The sample is introduced into the centrifugal separation tube, and into the regulation tube connected to the centrifugal separation tube, before centrifugal separation, and thereby the centrifugal separation tube is filled with the sample. When the centrifugal separation tube rotates around the first axis of rotation in a state where the centrifugal separation tube is filled with the sample, a target component is centrifugally separated from the sample filled in the centrifugal separation tube, that is, the sample of an amount equivalent to the volume of the centrifugal separation tube. Thus, since the sample can be introduced by using the regulation tube so that the interior of the centrifugal separation tube can be filled with the sample, the amount of the sample to be introduced can be regulated in a fixed amount for each introduction of a sample. Therefore, since a fixed amount of the sample may be centrifugally separated by the centrifugal separation tube, an almost fixed amount of the target component may be obtained.

An eighteenth aspect of the present invention provides a measuring chip, wherein in the seventeenth aspect of the present invention, the regulation tube has a first point and a second point in the regulation tube, and the distance between the first point and the first axis of rotation is smaller than the distance between the second point and the first axis of rotation.

In order to obtain a target component, a sample is introduced into the centrifugal separation tube and the regulation tube connected to the centrifugal separation tube. At this point, the sample is filled into the centrifugal separation tube and the regulation tube. When the measuring chip rotates around the first axis of rotation in this state, since the second point in the regulation tube has a larger distance than the distance to the first axis of rotation, a larger centrifugal force than the centrifugal force in the first point of the regulation tube is applied. Accordingly, the sample will be separated bordering on the first point. That is, a sample on the side of the centrifugal separation tube is introduced into the centrifugal separation tube from the first point to be centrifugally separated. On the other hand, a sample in the side of the regulation tube from the first point will be introduced into the regulation tube. Accordingly, an almost fixed amount of target components may be obtained from a fixed amount of the samples filled in the interior of the centrifugal separation tube.

A nineteenth aspect of the present invention provides a measuring chip for separating and measuring a target component in a sample by rotation around each of a first axis and a second axis of rotation, comprising: a centrifugal separation tube for centrifugally separating the target component from the sample by rotating the measuring chip around the first axis of rotation; a first holding section provided in the bottom of the centrifugal separation tube, wherein non-target components in the sample are introduced therein by rotation around the first axis of rotation, and the first holding section holds the non-target components during rotation around the second axis of rotation; and a plurality of measuring sections for measuring the target component introduced from the centrifugal separation tube by rotation around the second axis of rotation, wherein a first stage measuring section in a plurality of the measuring sections is connected with one end of the centrifugal separation tube, a measuring section after the first stage measuring section is connected to the preceding stage measuring section so as to introduce the target component into the following stage measuring section from the preceding stage measuring section, and the volume of the following stage measuring section is smaller than the volume of the preceding stage measuring section.

Separation and measurement of the target component in the sample can collectively be performed using two of the first axis of rotation and the second axis of rotation. Since non-target components are held in the first holding section, contamination of the non-target components to the target component may be suppressed in removing the target component out to the measuring sections of a plurality of stages, enabling effective removal of the target component separated in the centrifugal separation tube to the measuring section. As mentioned above, since the sample may be separated and measured by switching of the first axis of rotation to the second axis of rotation, the separation and measurement process may be simpler. Furthermore, the measuring section comprises a plurality of stages, and thus the remainder of the target component introduced into the preceding stage measuring section to be measured will be introduced into the following stage measuring section to be measured. Accordingly, a desired amount of the target component may be obtained from each of the measuring section comprising a plurality of stages. At this point, since the volume of the preceding stage measuring section is formed to be larger than the volume of the following stage measuring section, overflow of the target component introduced into the preceding stage measuring section to the centrifugal separation tube side from the following stage measuring section or the preceding stage measuring section side may be suppressed.

A twentieth aspect of the present invention provides a measuring chip, wherein in the nineteenth aspect of the present invention the measuring chip further comprises removing tubes connected to each of the measuring sections, and each extension line of each of the removing tubes intersects with the first axis of rotation.

Since the direction of the centrifugal force of rotation around the first axis of rotation is almost in agreement with the extending direction of each of the removing tubes, a target component measured by each of the measuring sections can be efficiently removed from the removing tube by rotation around the first axis of rotation.

A twenty-first aspect of the present invention provides a measuring chip, wherein in the nineteenth aspect of the present invention, the first stage measuring section has a measuring section connecting tube for connecting the centrifugal separation tube and the measuring section, each of the measuring sections after the following stage measuring section has a measuring section connecting tube for connecting the preceding stage measuring section and the following stage measuring section, and an extension line of the measuring section connecting tube of the first stage measuring section and extension lines of each of the measuring section connecting tubes of the measuring sections after the following stage measuring section intersect on the second axis of rotation.

Since the direction of the centrifugal force of the rotation around the second axis of rotation is almost in agreement with extending directions of each of the measuring section connecting tubes, the target component may be efficiently introduced into each of the measuring sections by rotation around the second axis of rotation.

A twenty-second aspect of the present invention provides a test chip for determining a target component in a sample by rotation around a first axis and a second axis of rotation, comprising: a centrifugal separation tube for centrifugally separating the target component from the sample by rotating the measuring chip around the first axis of rotation; a first holding section provided in the bottom of the centrifugal separation tube, wherein non-target components in the sample are introduced therein by rotation around the first axis rotation, and the first holding section holds the non-target components during rotation around the second axis of rotation; a measuring section connected to one end of the centrifugal separation tube, for measuring the target components introduced from the centrifugal separation tube by rotation around the second axis of rotation; at least one reagent reservoir storing a reagent therein; a mixing section connected with the reagent reservoir and the measuring section, the mixing section mixing the target component introduced from the measuring section by another rotation around the first axis of rotation, with the reagent introduced from the reagent reservoir by rotation around the first axis of rotation and/or the second axis of rotation; a photodetection path connected to the mixing section, the photodetection path passing a mixed substance obtained by mixing the reagent and the target component; a light inlet connected with the photodetection path, for introducing light into the photodetection path; and a light outlet connected with the photodetection path, for removing the light after passing through the photodetection path.

The sample is introduced into the centrifugal separation tube, and the target component is centrifugally separated from the sample in the centrifugal separation tube by rotating the chip around the first axis of rotation. At this point, the non-target components are introduced into the first holding section provided in the bottom of the centrifugal separation tube. Next, the target component separated by rotation around the second axis of rotation is introduced into the measuring section to be measured. The non-target components introduced into the first holding section in this rotation around the second axis of rotation are held untreated in the first holding section. Furthermore, the target component is introduced from the measuring section into the mixing section by rotation around the first axis of rotation, and is mixed with the reagent. Here, the reagent is introduced into the mixing section from the reagent reservoir by rotation around the first axis of rotation and/or the second axis of rotation. The mixed substance mixed therein is introduced into the photodetection path, and the target component is determined by detection of light that has passed through the interior of the photodetection path. Use of the test chip will enable collective performance of separation, measurement, mixing with the reagent, and determination of the target component in the sample, by means of the first axis of rotation and the second axis of rotation. Since the non-target components are held in the first holding section, contamination to the target component by the non-target components will be suppressed during the removal of the target component to the measuring section, and therefore the target component separated in the centrifugal separation tube may be effectively removed out into the measuring section. Accordingly, separation and measurement of the target component may be efficiently performed. Furthermore, as described above, switching of the first axis of rotation to the second axis of rotation, and of the second axis of rotation to the first axis of rotation will enable separation, measurement, and determination of the sample, and therefore simpler processes can be realized.

At this point, the measuring section has a desired volume and can accurately measure the target component introduced from the centrifugal separation tube. Since separation and measurement may be performed by only the rotation of the chip as described above, connection of the test chip with apparatuses, such as pumps, for separation and measurement, is unnecessary, allowing simplification of the structure of the overall apparatus with the test chip placed thereon. Since the sample is not removed to the exterior of the test chip until determination after the sample is introduced therein, contamination of the target component may be reduced and accurate determination of the target component will be realized. Furthermore, separation, measurement, mixing, and determination can be performed in one chip, and therefore miniaturization of the chip can be achieved.

Here, a connecting portion of the reagent reservoir and the mixing section is preferably located on the side of the second axis of rotation with respect to the bottom of the mixing section, and the volume of the bottom of the mixing section is preferably formed larger than the volume of the reagent reservoir. The reagent introduced into the mixing section from the reagent reservoir by rotation around the first axis of rotation will not cause backflow to the reagent reservoir from the mixing section by rotation around the second axis of rotation.

A twenty-third aspect of the present invention is a test chip for determining a target component in a sample by rotation around a first axis and a second axis of rotation, comprising: a centrifugal separation tube for centrifugally separating the target component from the sample by rotating the measuring chip around the first axis of rotation; a first holding section provided in the bottom of the centrifugal separation tube, wherein non-target components in the sample are introduced therein by rotation around the first axis rotation, and the first holding section holds the non-target components during rotation around the second axis of rotation; and a plurality of determining sections for measuring the target component introduced from the centrifugal separation tube by rotation around the second axis of rotation.

Each of the plurality of determining sections comprises a measuring section; at least one reagent reservoir having a reagent stored therein; a mixing section connected with the reagent reservoir and the measuring section, the mixing section mixing the target component introduced from the measuring section by another rotation around the first axis of rotation, and a reagent introduced from the reagent reservoir by rotation around the first axis of rotation and/or on the second axis of rotation; a photodetection path connected with the mixing section, the photodetection path passing a mixed substance of the reagent and the target component; a light inlet connected with the photodetection path, the light inlet introducing light into the photodetection path; and a light outlet connected with the photodetection path, the light outlet removing the light after passing through the interior of the photodetection path, wherein a measuring section of a first stage determining section among the plurality of determining sections is connected with one end of the centrifugal separation tube, a measuring section of the determining sections after the first stage is connected with the measuring section of the preceding stage determining section, so that the target component is introduced into the measuring section of the following stage determining section from the measuring section of the preceding stage determining section, and the volume of the measuring section of the following stage determining section(s) is smaller than the volume of the measuring section of the preceding stage determining section.

Separation, measurement, and determination of the target component in a sample may collectively be performed using two of the first axis of rotation and the second axis of rotation. Since the non-target components are held in the first holding section, contamination of the non-target components to the target component is suppressed in removing out the target component into the a plurality of stages of measuring sections, and therefore the target component separated in the centrifugal separation tube may be effectively removed out into the measuring section. Moreover, as described above, since switching of the first axis of rotation to the second axis of rotation and switching the second axis of rotation to the first axis of rotation may separate and measure the sample, a simpler separating and measuring process can be realized. Furthermore, the determining section constitutes a plurality of stages, and a remainder of the target component introduced into the measuring section of the preceding stage determining section and measured is then introduced into the measuring section of the following stage determining section to be measured.

Accordingly, in each of the determining sections of a plurality of stages, the target component in a desired amount may be measured and determined. Since the volume of the measuring section of the preceding stage determining section is formed to be larger than the volume of the measuring section of the following stage determining section at this point, overflow of the target component introduced into the measuring section of the preceding stage determining section, from the measuring section of the following stage determining section, into the centrifugal separation tube side or into the measuring section of the preceding stage determining section, may be reduced.

A twenty-fourth aspect of the present invention provides a test chip, wherein in the twenty-third aspect of the present invention, the test chip further comprises a removing tube for connecting each of the measuring sections with each of the mixing section of the determining sections, and each extension line of each of the removing tubes intersects on the first axis of rotation.

Since the direction of the centrifugal force of the rotation around the first axis of rotation is almost coincident with an extending direction of each of the removing tubes, the target component measured by each of the measuring sections may be efficiently removed out from the removing tubes by rotation around the first axis of rotation.

A twenty-fifth aspect of the present invention provides a test chip, wherein the measuring section of the first stage determining section has a measuring section connecting tube for connecting the centrifugal separation tube with the measuring section of the determining section, each of the measuring section of the determining section after the following stage has a measuring section connecting tube for connecting the measuring section of the preceding stage determining section with the measuring section of the following stage determining section, and an extension line of the measuring section connecting tube of the measuring section of the first stage determining section, and each extension line of each of the measuring section connecting tubes of the measuring sections of the determining section after the following stage intersect on the second axis of rotation, in the twenty-third aspect of the present invention.

Since the direction of the centrifugal force of the rotation around the second axis of rotation is almost coincident with an extending direction of each of the measuring section connecting tubes, the target component may be efficiently introduced into each of the measuring sections by rotation around the second axis of rotation.

A twenty-sixth aspect of the present invention provides a test chip, wherein in the twenty-second or twenty-third aspect of the present invention, the test chip further comprises a sampling needle connected with the centrifugal separation tube, the sampling needle serving to extract the sample.

Since the sampling needle is connected to the test chip, extraction, separation, measurement, and determination of the sample may be collectively performed. Accordingly, contamination of the sample may be reduced and accurate determination can be realized.

A twenty-seventh aspect of the present invention provides a method for using a test chip, a target component being introduced therein, comprising the steps of: centrifugally separating the target component from a sample by rotation around a first axis of rotation, and holding non-target components; and measuring the target component by rotation of chip around a second axis of rotation while holding the non-target components in an untreated state.

In the separating step, the target component is centrifugally separated from the sample by rotation around the first axis of rotation. At this point, the non-target components are held in the untreated state. In the following measuring step, the target component is measured by rotation around the second axis of rotation. Here, the non-target components held by the separating step are held in an untreated state. Use of the method enables collective performance of separation and measurement of the target component in the sample, using two of the first axis of rotation and the second axis of rotation. Since the non-target components are held untreated, contamination of the non-target components into the target component may be suppressed in measuring of the target component, allowing effective measurement of the target component. As described above, since the sample may be separated and measured by switching of the first axis of rotation to the second axis of rotation, separation and measurement process may be simpler. Furthermore, separation and measurement enabled only by rotation of the chip do not require connection with an apparatus, such as a pump, of the chip for separation and measurement, and the structure of the entire apparatus with the chip laid thereon can be more simplified.

A twenty-eighth aspect of the present invention provides a method for using a chip, the chip comprising a reagent reservoir holding a reagent; and a mixing section connected with the reagent reservoir, the method further comprising the steps of: introducing the reagent into the mixing section from the reagent reservoir by rotation around the first axis of rotation and/or the second axis of rotation of the chip; and mixing the target component with the reagent, the target component measured in the measuring step being introduced into the mixing section by rotation around the first axis of rotation of the chip.

The reagent is introduced into the mixing section by rotation around the same axis of rotation as the axis of the separating step and/or the measuring step. The target component separated and measured is introduced into the mixing section by rotation around the first axis of rotation, and, subsequently is mixed with the reagent. Use of the method described above allows collective performance of separation, measurement, and mixing with the reagent of the target component in the sample. Furthermore, since switching of the first axis of rotation to the second axis of rotation and the second axis of rotation to the second axis of rotation enables performance of separation, measurement, and mixing with the reagent of the sample, a simpler process can be realized.

Since the target component is accurately measured at this point, a mixed substance having a desired mixing ratio between the reagent and the target component may be obtained.

As described above, performance of separation, measurement, and mixing only by means of the rotation of the chip may further simplify the structure of the entire apparatus containing the chip currently laid thereon. Since neither the sample nor the target component is removed out of the chip in steps until the sample is introduced and mixed with the reagent, contamination of the sample or the target component may be reduced. In addition, since separation and measurement may be performed in one chip, miniaturization of the chip may be achieved.

Here, introduction of the reagent is preferably performed concurrently with the separation, measurement, or mixing. Introduction of the reagent into the mixing section is performed at the time of the rotation of the chip in the separation, measurement, or mixing. Accordingly, a mixed substance may quickly be obtained.

Moreover, the method further preferably comprises the steps of: irradiating light onto the mixed substance of the target component and the reagent; and determining the target component by extracting the light after passing through the interior of the mixed substance. Light is irradiated onto the mixed substance of the reagent and the target component, and then the light is extracted after passage in order to determine the target component. Accordingly, use of the method enables collective performance of separation, measurement, mixing with the reagent, and determination of the target component in the sample, by two of the first axis of rotation and the second axis of rotation. Furthermore, performance of separation, measurement, mixing, and determination in one chip may achieve miniaturization of the chip. Since the target component is accurately measured at this point, a mixed substance having a desired mixing ratio between the reagent and the target component may be obtained. Moreover, since the target component is not removed out from the chip, contamination of the target component may be reduced to be determined accurately.

PREFERRED EMBODIMENTS OF THE INVENTION

Basic Constitution

Figure 1A:
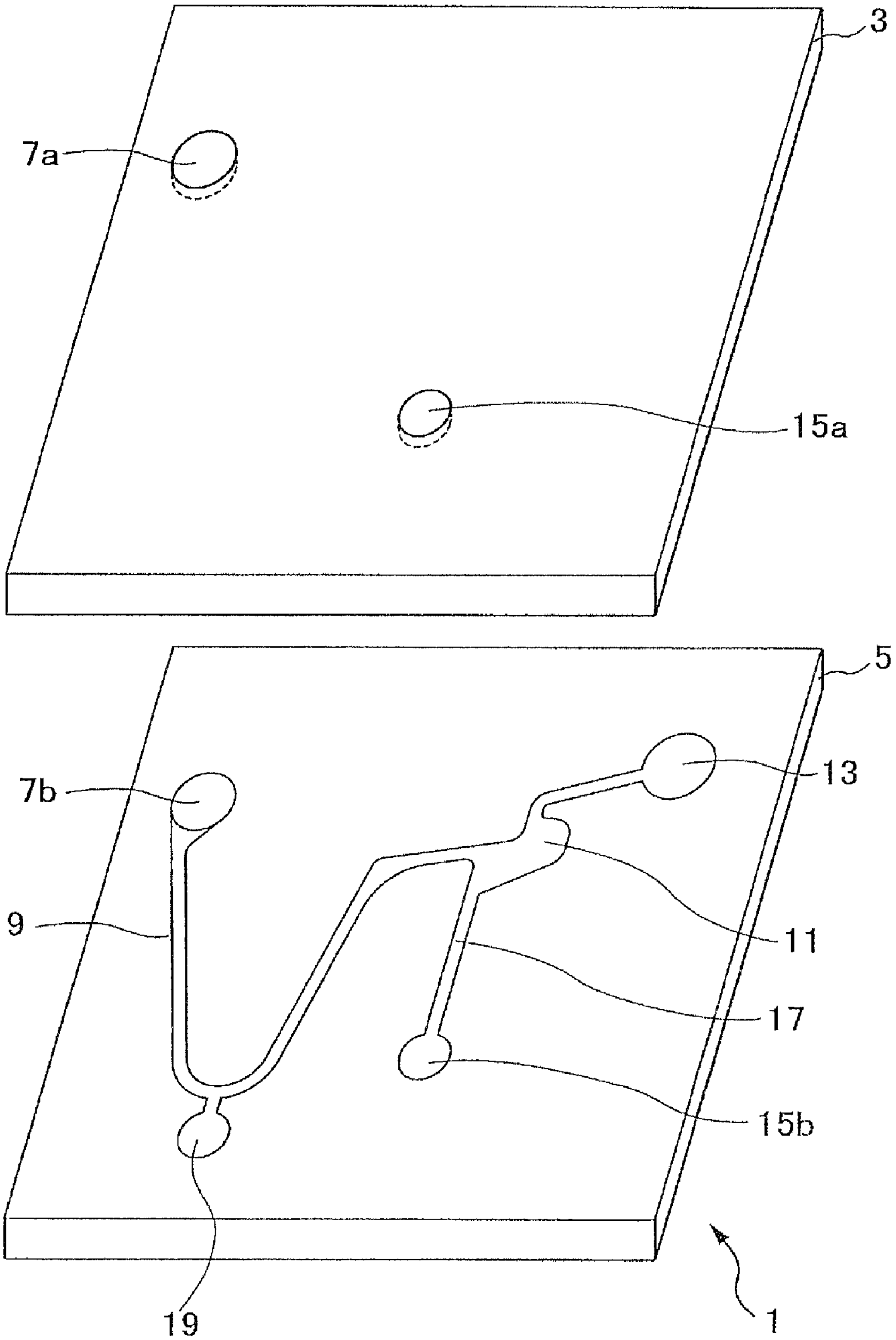
FIG. 1A is a perspective view of a test chip according to present invention.
Figure 1B:
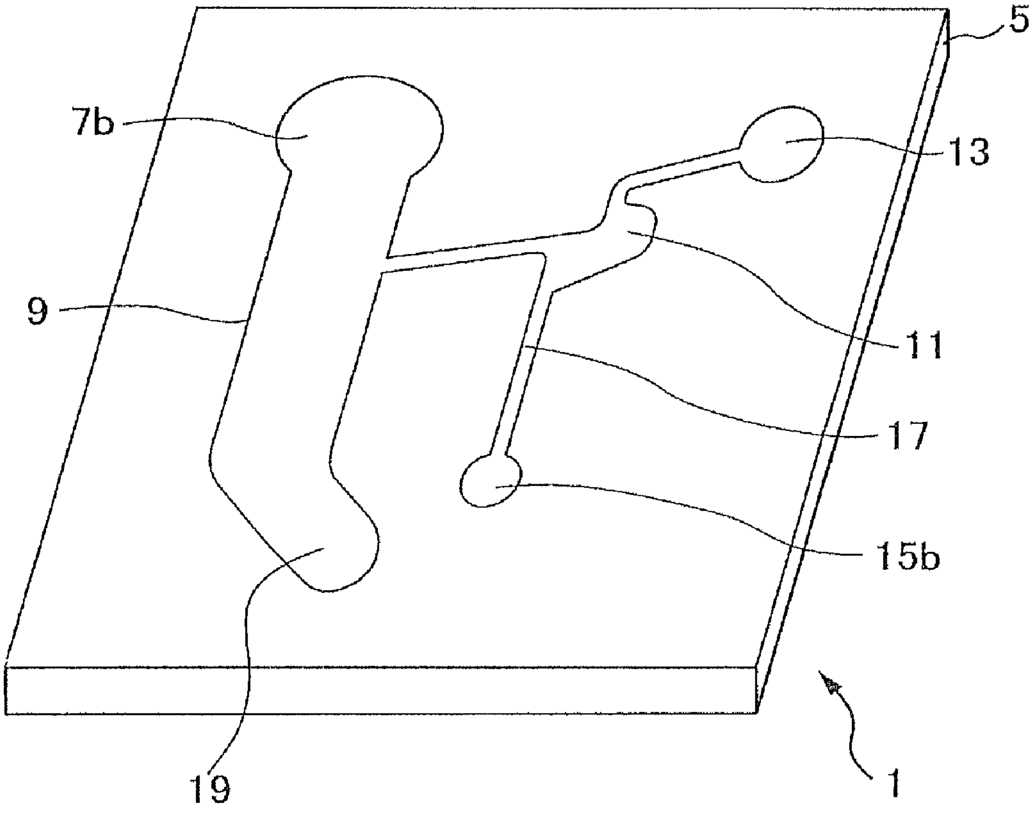
FIG. 1B is a perspective view of another test chip according to present invention.
Figure 2:
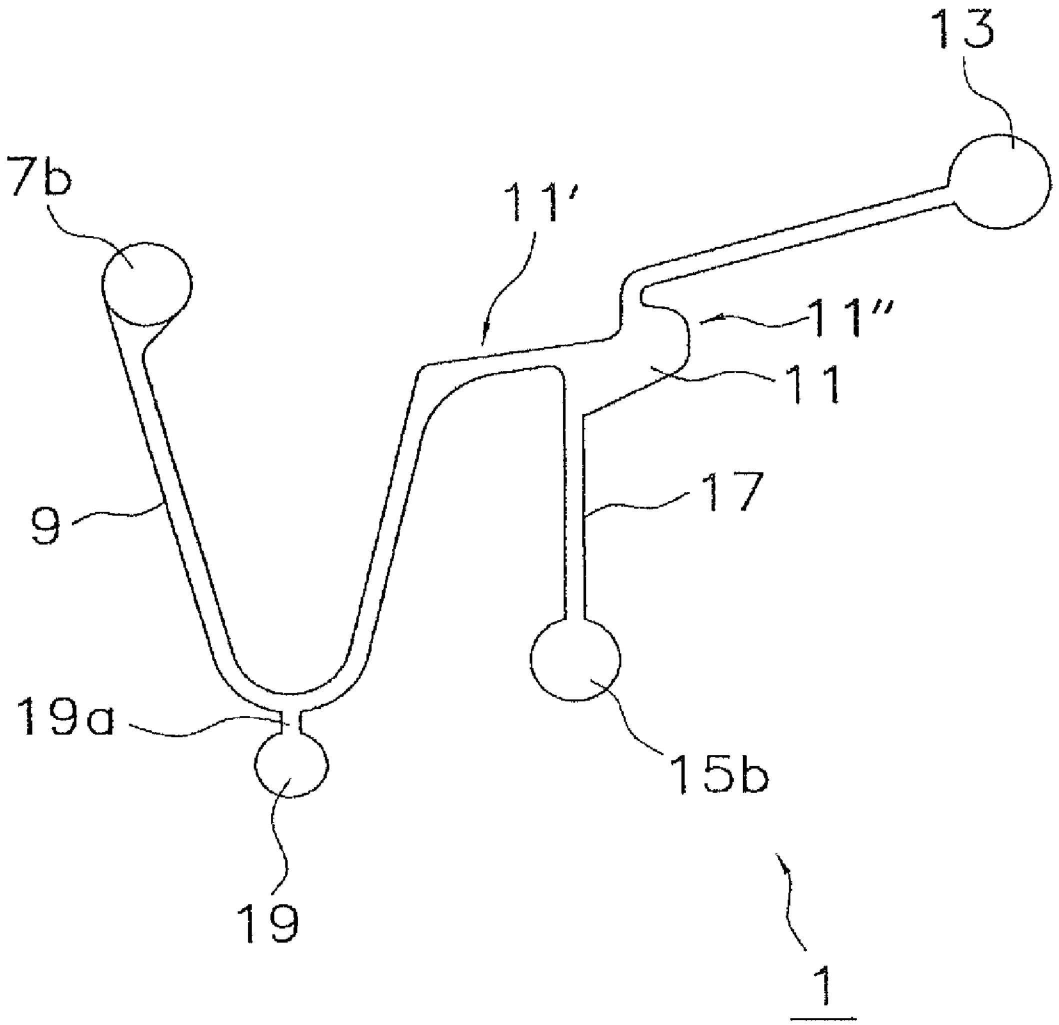
FIG. 2 is an enlarged plan view of FIG. 1A.

FIG. 1A and FIG. 1B are perspective views of a test chip according to the present invention, and FIG. 2 is an enlarged plan view of FIG. 1A.

Structure of Test Chip

The test chip 1 has a first substrate 3 and a second substrate 5, which are plate shaped substrates. An inlet 7*a* and an outlet 15*a* are formed in the first substrate 3. An inlet 7*b*, a centrifugal separation tube 9, a first measuring section 11, a waste fluid reservoir 13, and a removing tube 17 corresponding to the inlet 7*a*, an outlet 15*b* corresponding to the outlet 15*a*, and a first holding section 19 are formed in the second substrate 5. The test chip 1 has a first axis of rotation 21 and a second axis of rotation 22, described below.

A sample 40 that is the subject of testing is introduced into the test chip 1 via the inlet (7*a*, 7*b*) 7 of the test chip 1. A centrifugal separation tube 9 is connected to the inlet 7, and the sample 40 is introduced into the centrifugal separation tube 9 from the inlet 7. The centrifugal separation tube 9 has a substantially U-shape, with one open end portion thereof connected to the measuring section 11, and the other open end portion thereof connected to the inlet 7. The first holding section 19 is connected to the bottom of the U-shape, and an opening of the U-shape of the centrifugal separation tube 9 is placed so that it can substantially face the first axis of rotation 21 side. In addition, during the rotation of the test chip 1 around the first axis of rotation 21, a target component 41 is centrifugally separated from the sample 40, within the centrifugal separation tube 9. In this rotation around the first axis of rotation 21, non-target components 43 other than the target component 41 in the sample 40 are simultaneously introduced into the first holding section 19 in the bottom of the centrifugal separation tube 9.

The target components 41 are introduced into the first measuring section 11 by rotation around the second axis of rotation 22 from the centrifugal separation tube 9. More particularly, the target component 41 is introduced from a measuring section connecting tube 11', which is a connecting portion with the centrifugal separation tube 9 of the first measuring section 11, into the bottom 11" of the first measuring section 11 by centrifugal force generated by rotation around the second axis of rotation 22. Here, the non-target components 41 introduced into the first holding section 19 by rotation around the first axis of rotation 21 are held untreated within the first holding section 19 during the rotation around the second axis of rotation 22. That is, because the non-target components 43 introduced into the first holding section 19 will rarely be introduced into the centrifugal separation tube 9 from the first holding section 19, even by rotation around the second axis of rotation 22, only the target component 41 will be introduced into the first measuring section 11. Furthermore, the waste fluid reservoir 13 is connected to the first measuring section 11, and the target component 41 exceeding a predetermined volume of the first measuring section 11 will be introduced into the waste fluid reservoir 13. Therefore, a desired quantity of target component 41 may be measured. Furthermore, by rotation around the first axis of rotation 21, the target component 41 measured will be introduced from the first measuring section 11 into the outlet 15 via the removing tube 17 connected to the first measuring section 11.

Here, the centrifugal separation tube 9 is not limited to one having a U-shape, but for example, it is may be formed to have a cup shape, as shown in FIG. 1B. At this point, the first holding section 19 and the centrifugal separation tube 9 are integrally formed, and the first holding section 19 is formed so as to have an opening in the direction of the second axis of rotation in order to avoid the non-target components 43 being introduced into the first measuring section 11 by rotation around the second axis of rotation 22. In addition, the non-target components 43 in the sample 40 are introduced into the first holding section 19 by rotation around the first axis of rotation 21 in a sample 40 introduced into the centrifugal separation tube 9 and the first holding section 19 integrally formed with the centrifugal separation tube 9. Subsequently, the target component 41 as a supernatant fluid obtained in the centrifugal separation tube 9 is then introduced into the first measuring section 11 by rotation around the second axis of rotation 22 in order to be measured in the same manner as described above.

(2) Method for Using the Test Chip

Next, an example of a method for using the test chip 1 when a target component 41 is to be separated and measured will be described with reference to FIGS. 3 to 6.

A sample 40 comprising a target component 41 is introduced into a centrifugal separation tube 9 (the U-shaped tube shown with the solid line in FIG. 3) from an inlet 7 in a test chip 1, and then the test chip 1 is fixed to an rotation apparatus (not shown). Separation and measurement of the target component 41 is performed as follows.

Figure 3:
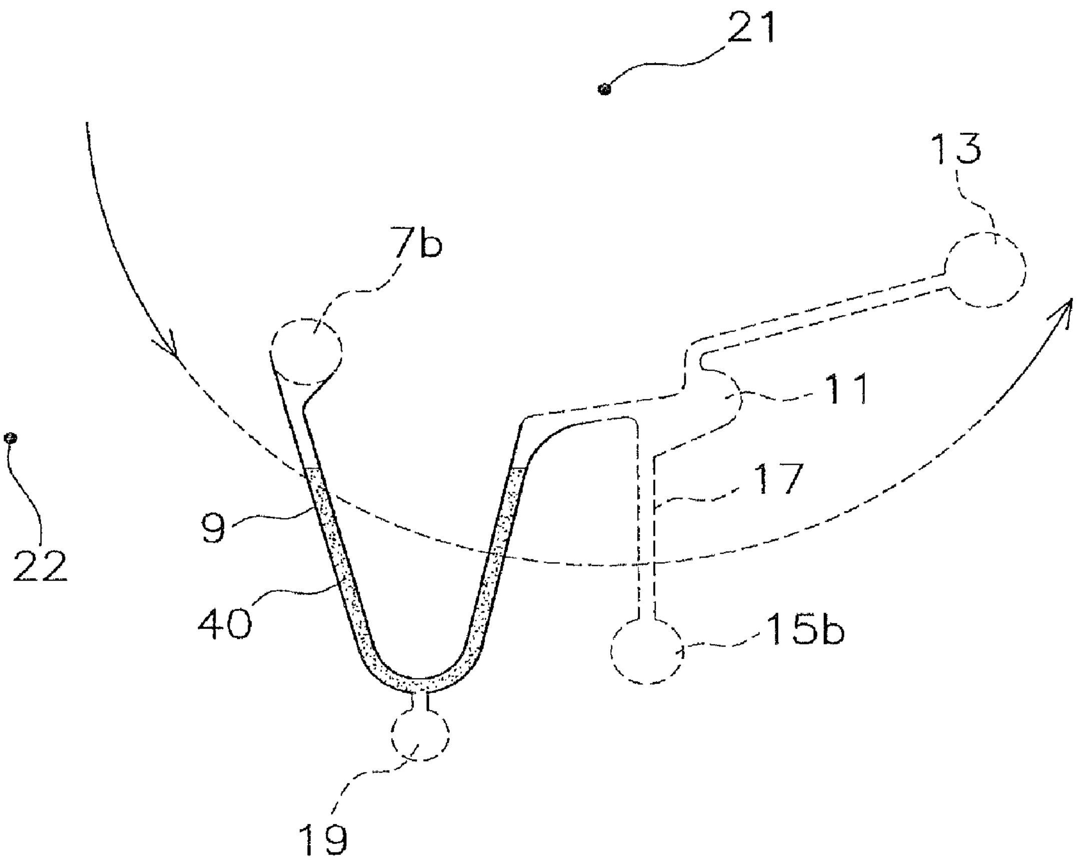
FIG. 3 is an example (1) of a method for using a test chip 1.
Figure 4:
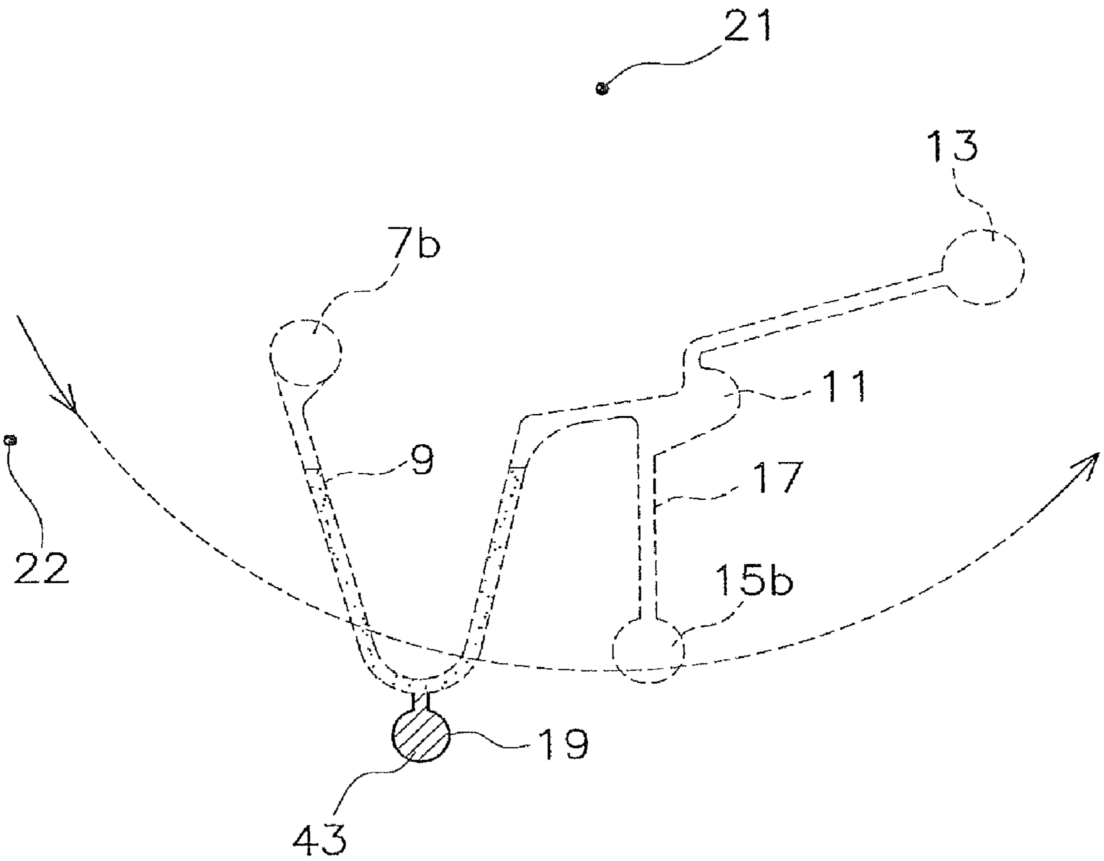
FIG. 4 is an example (2) of a method for using the test chip 1.

Step 1:

The test chip 1 is rotated around a predetermined first axis of rotation 21, and the centrifugal separation tube 9 is rotated in the direction of the arrow shown in FIG. 3. The target component 41 is centrifugally separated from the sample 40 introduced into the centrifugal separation tube 9 by means of this rotation. At this point, the centrifugal force works in the direction of the bottom of the U-shaped centrifugal separation tube 9 from the opening of the centrifugal separation tube 9 by rotation around the first axis of rotation 21. Accordingly, non-target components 43 other than the target component 41 in the sample 40 move to the first holding section 19 (the section shown with a solid line in FIG. 4) at the bottom of the centrifugal separation tube 9, and are held therein. Thus, the target component 41 is separated from the sample 40 (refer to FIG. 4).

Figure 5:
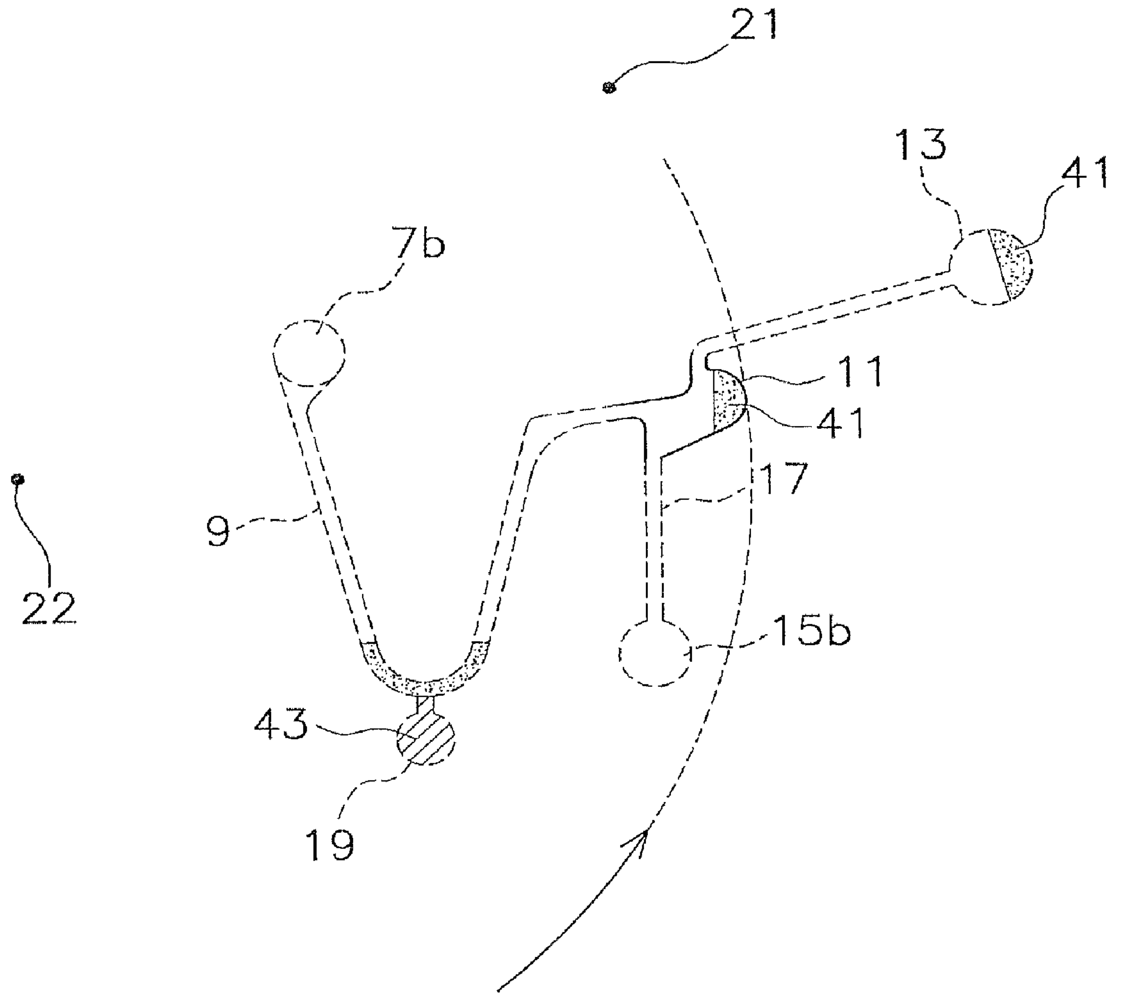
FIG. 5 is an example (3) of a method for using the test chip 1.

Step 2:

Next, the test chip 1 is rotated in the direction of FIG. 5 around the predetermined second axis of rotation 22. The centrifugally separated target component 41 is introduced into a first measuring section 11 (the section shown with the solid line in FIG. 5) from the centrifugal separation tube 9, and is measured. Since in this rotation around the second axis of rotation 22, the non-target components 43 introduced into the first holding section 19 are held untreated in the first holding section 19, only the target component 41 will be introduced into the first measuring section 11. At this point, the target component 41 exceeding a predetermined volume of the first measuring section 11 is introduced into a waste fluid reservoir 13 connected to the first measuring section 11 (refer to FIG. 5).

Figure 6:
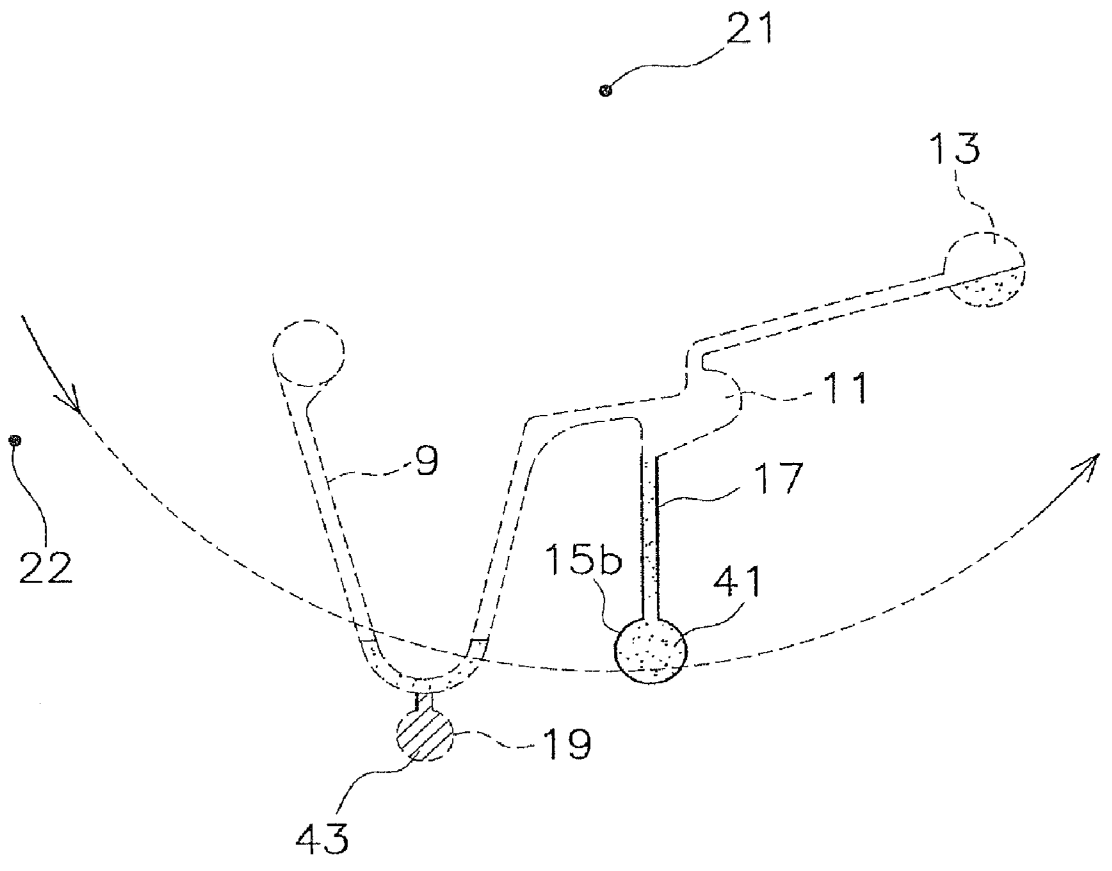
FIG. 6 is an example (4) of a method for using the test chip 1.

Step 3:

Furthermore, the test chip 1 is rotated around the first axis of rotation 21, and the target component 41 introduced into the first measuring section 11 is then removed via the removing tube 17 and the outlet 15 (the section shown with a solid line in FIG. 6) (refer to FIG. 6). At this point, at the first measuring section 11, the centrifugal force works in the direction of the removing tube 17 and the outlet 15 from the first measuring section 11 by rotation around the first axis of rotation 21. Accordingly, the target component 41 moves to the removing tube 17 and the outlet 15.

Test Chip Manufacturing Method

The test chip 1 may be prepared by an imprint method or an injection molding method. The substrate materials that can be used will depend on the method of manufacturing used, and include PET (polyethylene terephthalates), Si, Si oxide, quartz, glasses, PDMS (polydimethyl siloxanes), PMMA (poly methyl methacrylates), PC (polycarbonates), PP (polypropylenes), PS (polystyrenes), PVC (polyvinyl chlorides), polysiloxanes, allyl ester resins, cycloolefin polymers, silicone resins, etc.

Effects

Using the test chip 1, separation and measurement of the target component 41 in the sample 40 may collectively be performed, by use of two of the first axis of rotation 21 and the second axis of rotation 22. Since the non-target components are held in the first holding section, contamination with the non-target components to the target component may be suppressed when removing the target component to the first measuring section, and the target component separated in the centrifugal separation tube may be effectively removed into the first measuring section.

Accordingly, efficient separation of the target component and measuring can be realized. As described above, since the sample may be separated and measured by switching the first axis of rotation to the second axis of rotation, the separation and measurement process can be simplified.

At this point, the first measuring section 11 has a predetermined volume, and it can accurately measure the target component 41 introduced from the centrifugal separation tube 9. Furthermore, since the application of heat and the like is not needed for separation and measurement, the sample 40 will not be influenced by heat and the like. Accordingly, contamination and transformation of the sample 40 may be reduced, and therefore accurate measurement of the target component 41 contained in the sample 40 will be achieved. In addition, since the separation and measurement of the target component 41 are performed by simply rotating the test chip 1 as described above, the connection of the test chip 1 with an apparatus, such as a pump, will not be needed for separation and measurement, allowing the overall structure of the apparatus having the test chip 1 placed thereon to be simplified. Since separation and measurement can be performed in one chip, miniaturization of the test chip 1 will also be realized.

Furthermore, since the test chip 1 does not require the installation of a valve that is subsequently removed during separation and measurement, and has a simpler structure that allows separation and measurement of the target component 41, easier manufacturing of the chip will be enabled. This test chip 1, as shown in FIG. 1, is preferably formed so that it may extend in two dimensions, along the radial direction of a circle around the first axis of rotation 21 and the second axis of rotation 22. When the test chip 1 is formed to be a plate shaped substrate, the centrifugal separation tube 9, the first measuring section 11, and the like may easily be manufactured in the test chip 1 by using the above-described injection molding method or the imprint method. In addition, since the centrifugal separation tube 9, the first measuring section 11, and the like are manufactured on one substrate, and the test chip 1 can easily be manufactured by laminating another substrate thereto, the test chip 1 can be made thinner and smaller.

Figure 7:
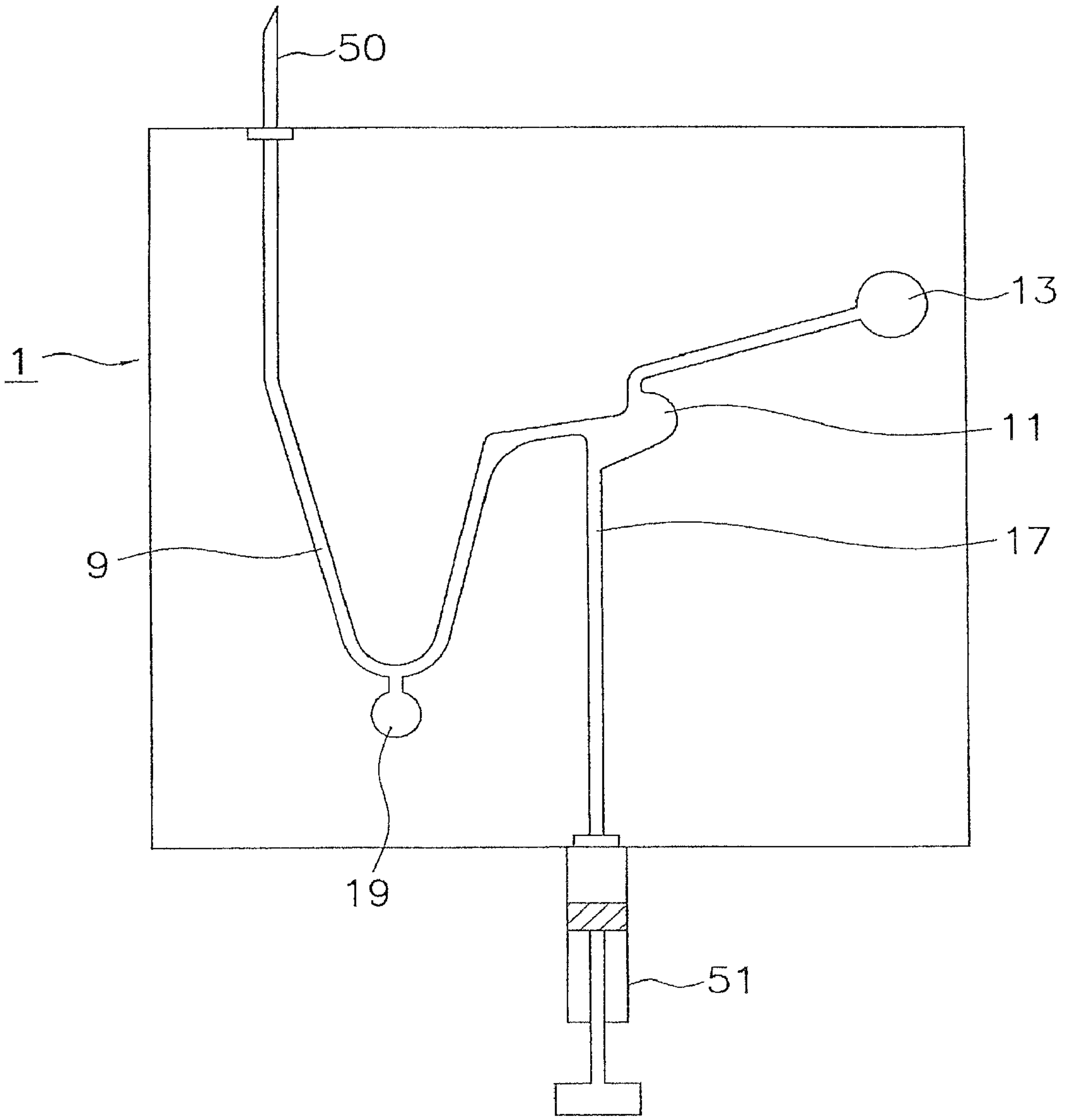
FIG. 7 is plan view of another test chip according to present invention.

As shown in FIG. 7, when a sampling needle 50 and a syringe 51 are provided in the test chip 1, collective and simpler extractuib, separation, and weighing of the sample 40 will be attained. Accordingly, the time and effort needed to introduce the sample 40 sampled by another means into the test chip 1 will be saved, allowing a reduction in contamination of the sample 40 when introducing the same into the test chip 1. Furthermore, since it is also possible to directly obtain a blood sample from a vein with the sampling needle 50, a substantially pure target component can be accurately measured. This sampling needle 50 and the syringe 51 may be removed when attaching the test chip 1 to the apparatus 20. Furthermore, a dropping pipette may be provided instead of the syringe 51, and the sample 40 may be obtained by using the dropping pipette.

First Embodiment

Figure 8A:
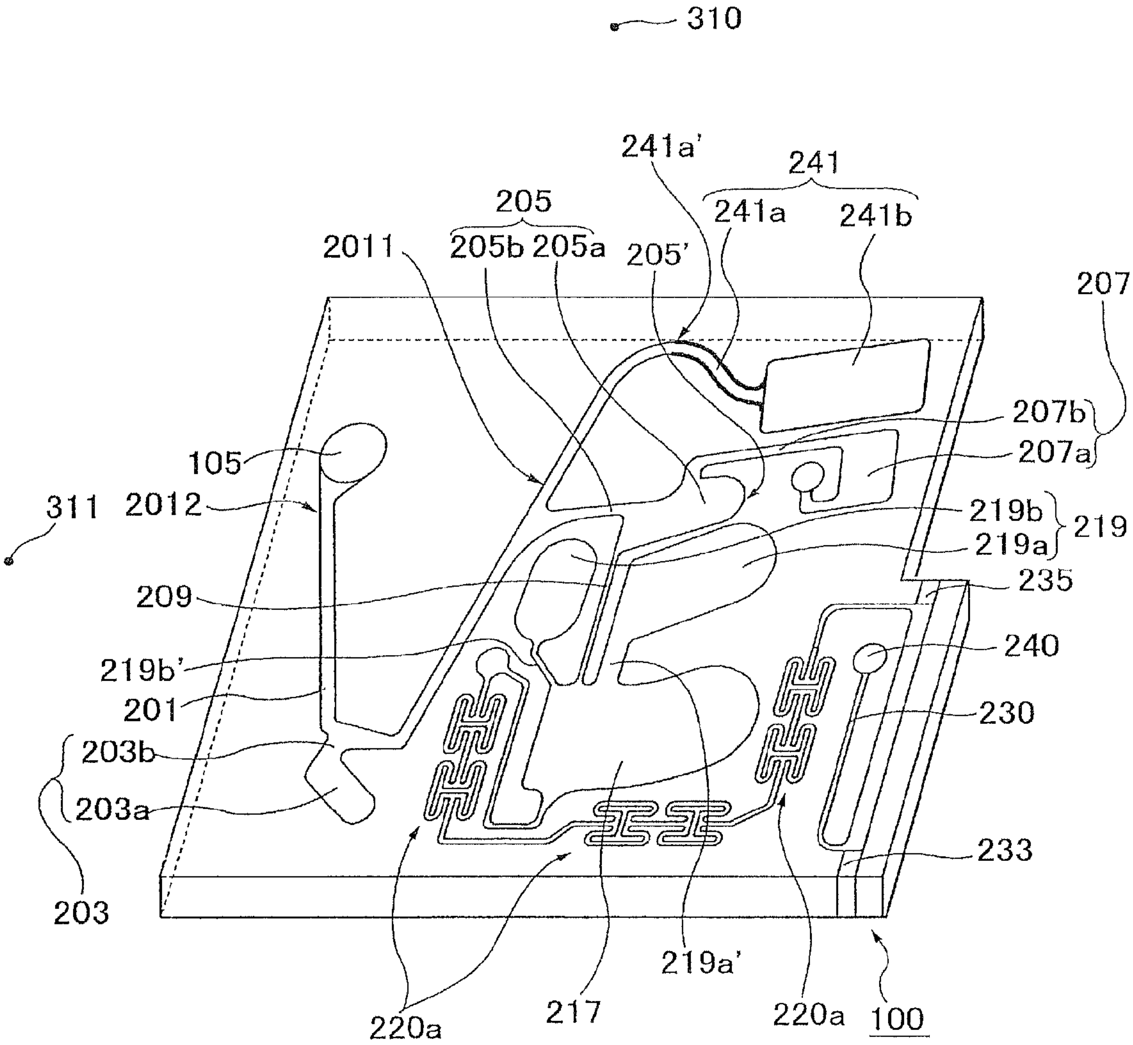
FIG. 8A is a perspective view of a test chip according to the first embodiment of the present invention.
Figure 8B:
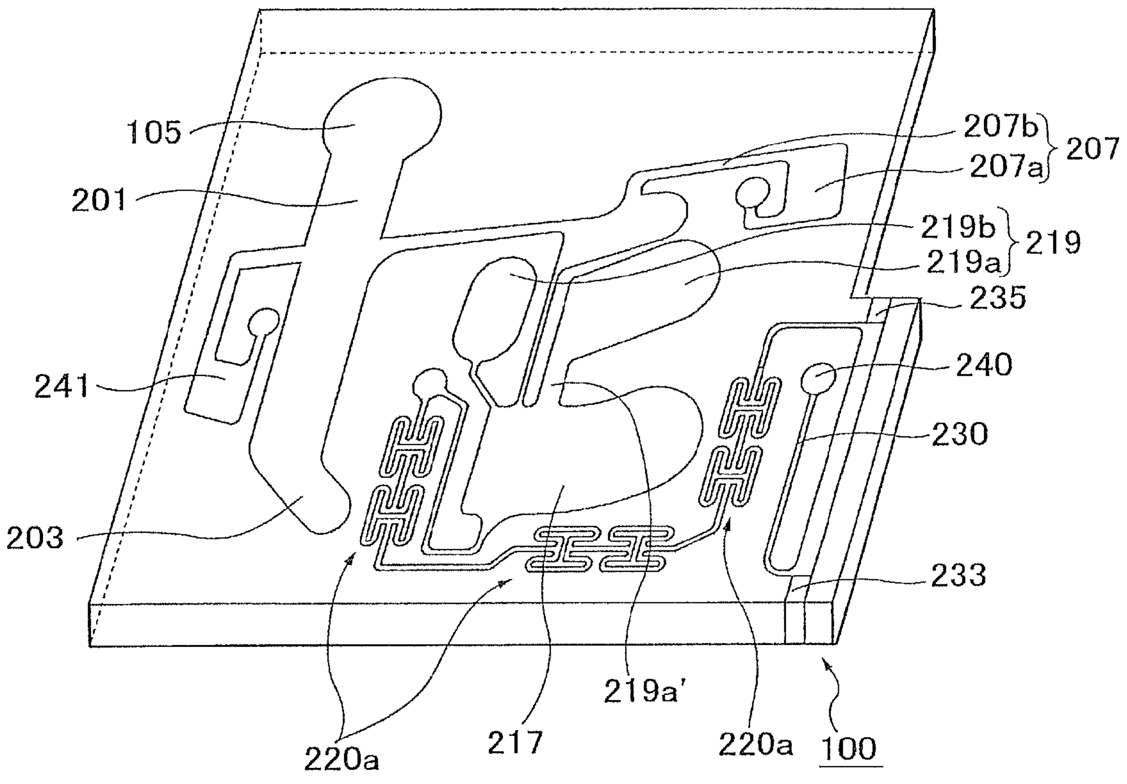
FIG. 8B is a perspective view of another test chip according to the first embodiment of the present invention.

FIG. 8A and FIG. 8B are perspective views of a test chip according to the first embodiment of the present invention.

Overall Configuration of the Test Chip

Figure 9A:
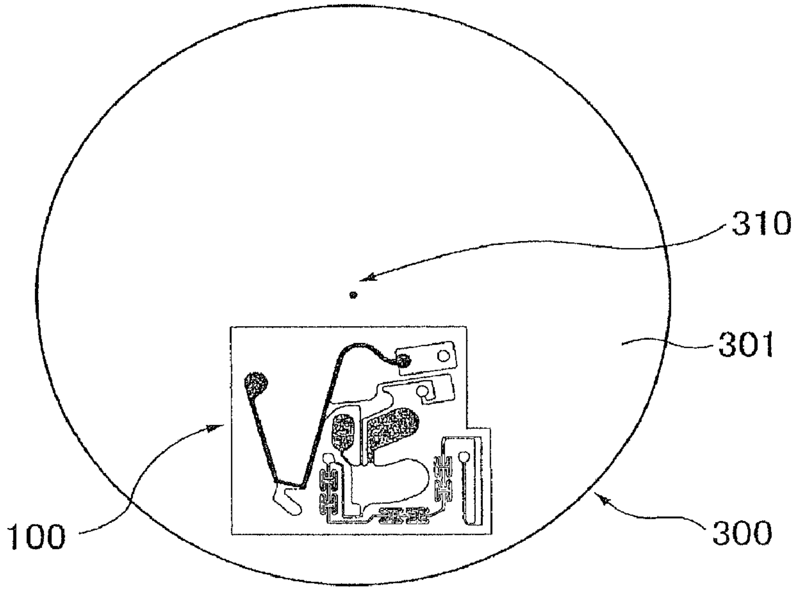
FIG. 9A is a related view of an rotation apparatus and a test chip with the test chip laid thereon.
Figure 9B:
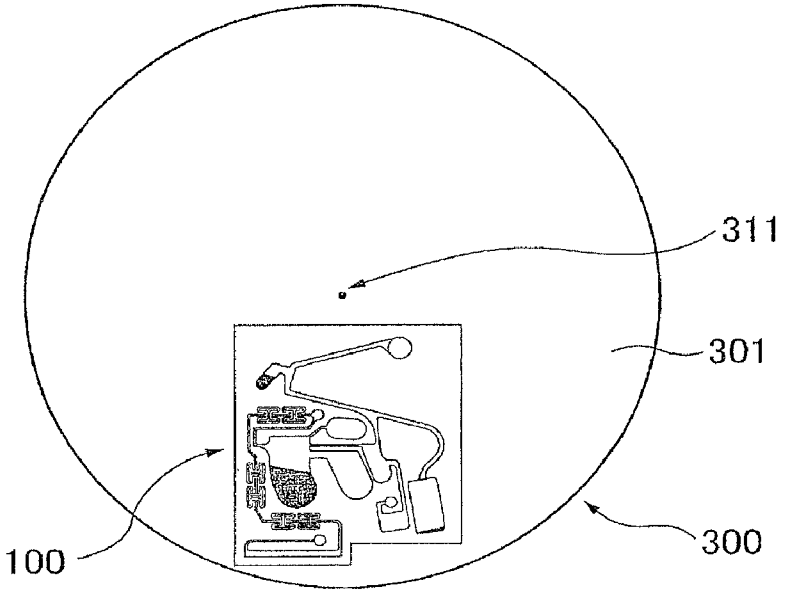
FIG. 9B is a related view of an rotation apparatus when rotating a test chip in the state shown in FIG. 9A, and the test chip.

A test chip 100 of the first embodiment comprises an inlet 105 for a sample containing a target component, a centrifugal separation tube 201, a holding section (203*a*, 203*b*) 203, a first measuring section (205*a*, 205*b*) 205, a waste fluid reservoir (207*a*, 207*b*) 207, a removing tube 209, a primary mixing section 217, a reagent reservoir (219*a*, 219*b*) 219 for storing a reagent, a secondary mixing section 220 comprising a mixer section 220*a*, a photodetection path 230, a light inlet 233, a light outlet 235, an outlet 240, and a regulation tube (241*a*, 241*b*) 241. As shown in FIGS. 9A and 9B, this test chip 1 separates and measures a target component, and mixes the target component and a reagent by rotation around the first axis of rotation 310 and the second axis of rotation 311 described below.

An inlet 105 incorporates a sample 500 as a subject for testing. A centrifugal separation tube 201 has a substantially U-shape, one open end portion thereof is connected to a first measuring section 205 and a regulation tube 241, and the other open end thereof is connected to the inlet 105. A first holding section 203 is connected to the bottom of the U-shape of the centrifugal separation tube 201. The first measuring section 205 into which a target component 510 is to be introduced is connected to a waste fluid reservoir 207 and a removing tube 209. A primary mixing section 217 is connected to the removing tube 209, into which the target component 510 is introduced from the first measuring section 205. Furthermore, the primary mixing section 217 is connected with a reagent reservoir 219 having a reagent 550 stored therein, into which the reagent 550 is introduced. Therefore, in the primary mixing section 217, the target component 510 and the reagent 550 are joined and mixed together. The target component 510 and the reagent 550 in the primary mixing section 217 are introduced into a secondary mixing section 220 connected to the primary mixing section 217, and are further mixed. A mixed substance 560 is introduced into a photodetection path 230 connected to the secondary mixing section 220.

Overall configuration of the rotation apparatus and detecting device

Figure 10:
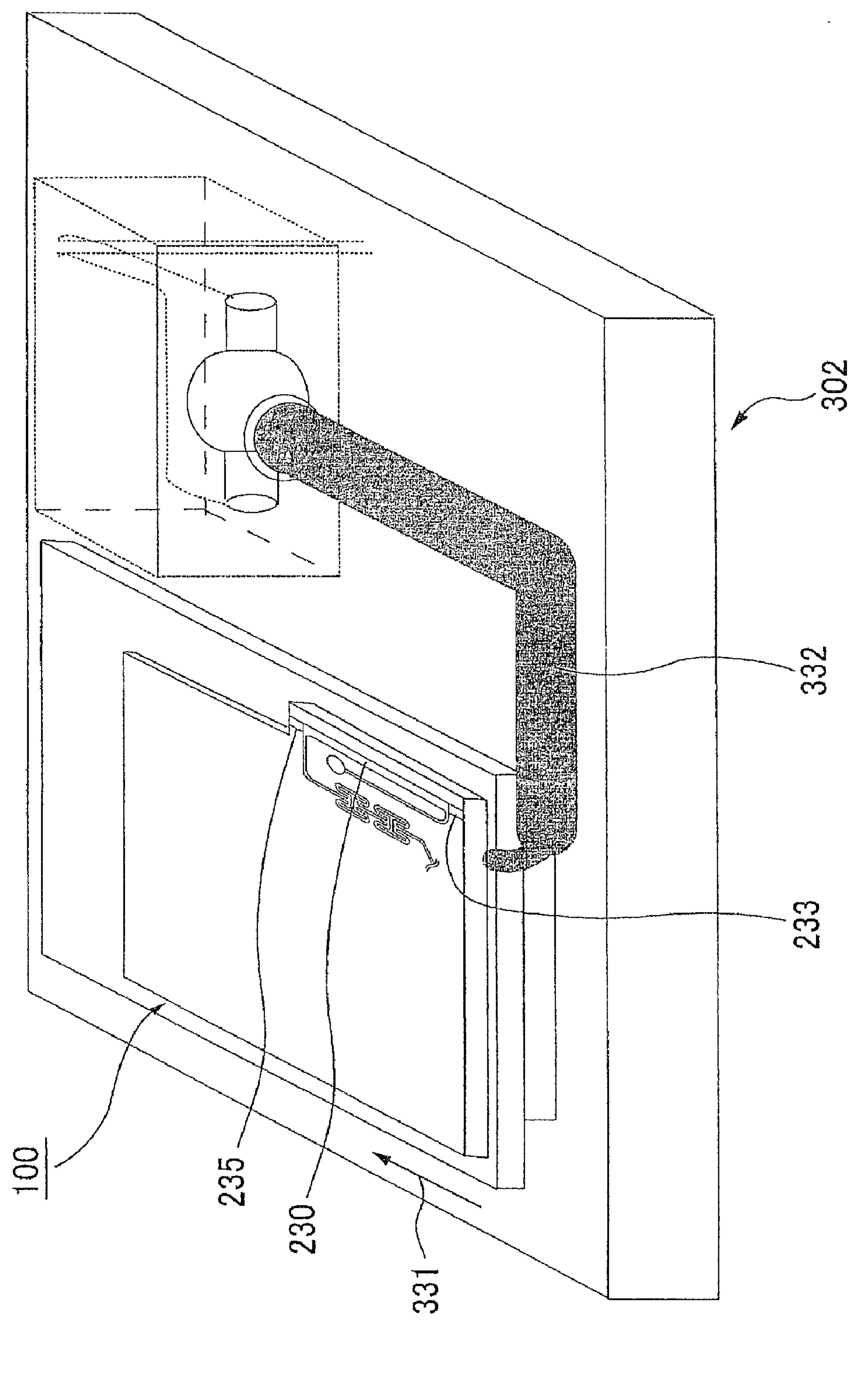
FIG. 10 is a schematic diagram of a detecting device.

An outline of the rotation apparatus 300 for rotating the test chip 100, and a detecting device 302 for irradiating light onto the test chip 100 and extracting the same will be described below. FIG. 9A and FIG. 9B are views showing the relationship between the rotation apparatus with a test chip placed thereon, and the test chip, and FIG. 10 is a schematic diagram of a detecting device.

The rotation apparatus 300 has a rotating platform 301 for fixing the test chip 100 with respect to the rotation apparatus 300 and for rotating the chip, and a first axis of rotation 310 and a second axis of rotation 311 for rotating the rotating platform 301. Here, in the rotation apparatus 300 shown in FIG. 9A and FIG. 9B, the first axis of rotation 310 and the second axis of rotation 311 are coincident with a central location of the rotating platform 301. This is because a configuration is adopted wherein the first axis of rotation 310 and the second axis of rotation 311 may be coincident with the center of rotation of the rotating platform 301 by changing the direction in which the test chip 100 to be placed. The rotation apparatus 300 may further have a pump section 333 (not shown) for feeding a reagent to a reagent reservoir 219, and for transporting the liquids of the sample 500 and target component 510 within the test chip 100.

The test chip 100 is fixed so that the first axis of rotation 310 or the second axis of rotation 311 may be coincident with the center of rotation of the rotating platform 301. That is, on the one hand, when the test chip 100 rotates around the first axis of rotation 310, the test chip 100 is fixed so that the center of rotation of the rotating platform 301 and the first axis of rotation 310 may be coincident with each other, as shown in FIG. 9A. On the other hand, when the test chip 100 rotates around the second axis of rotation 311, the test chip 100 is rotated in the state shown in FIG. 9A, and as shown in FIG. 9B, it is fixed so that the center of rotation of the rotating platform 301 and the second axis of rotation 311 may be coincident. Although the test chip 100 is rotated here so that the first axis of rotation 310 or the second axis of rotation 311 might be coincident with the center of rotation of the rotating platform 301, the test chip 100 can be fixed to a rotating platform 301 having two centers of rotation. In this case, the rotation of the test chip 100 itself is not necessary in order to change the center of rotation of the rotating platform 301.

Furthermore, in the rotation apparatus 300, in order to determine the target component 510 mixed with the reagent 550, the test chip 100 is then fixed to the detecting device 302. This detecting device 302 has a supporting member 331 comprising a Peltier device thermocouple for performing temperature regulation, an optical fiber 332, and a control section 320 (not shown). This control section 320 has, for example, a centrifuge control section 321, a pump control section 323, a temperature control section 325, a light controlling section 327, and a current electric potential amplifier 329 and the like, and they control each part of the apparatus 302.

Configuration of Each Portion of the Test Chip

Figure 11:
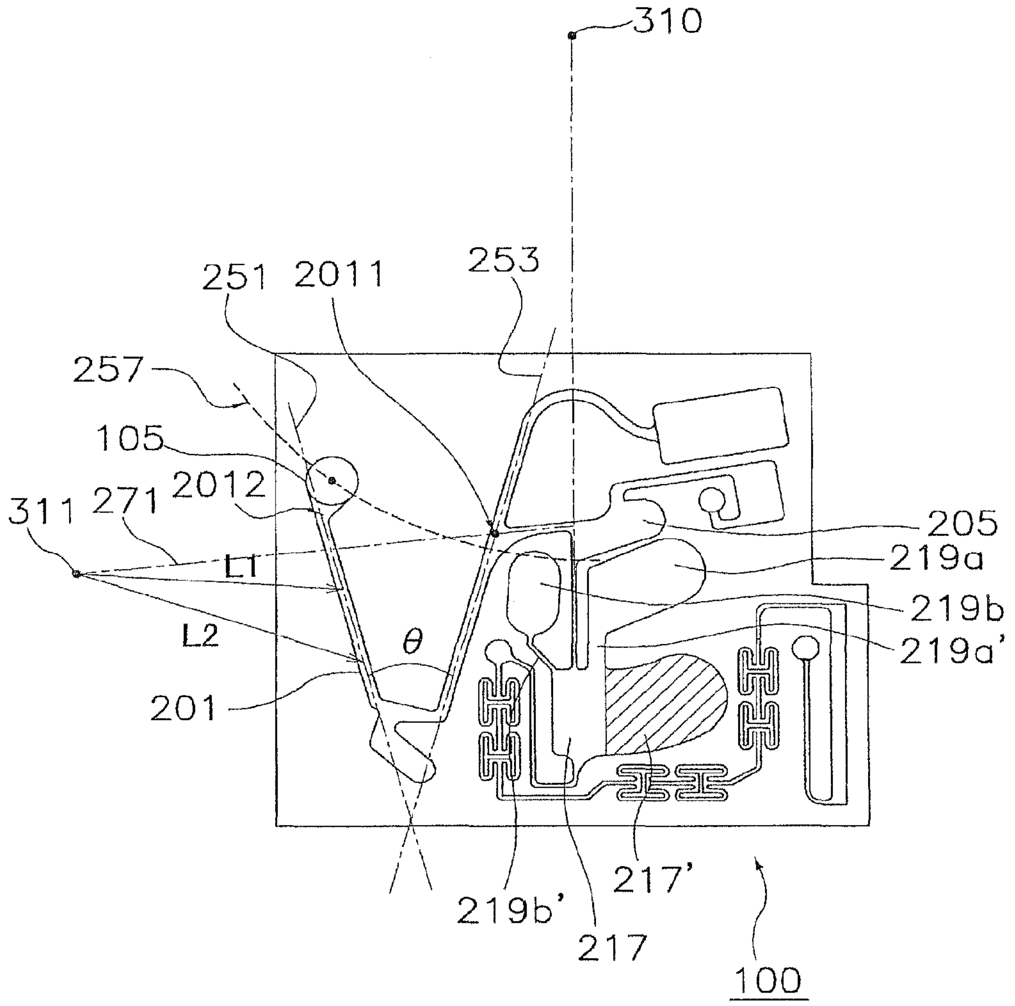
FIG. 11 is a related view of each portion of the test chip of FIG. 8A, and two axes of rotation.
Figure 12:
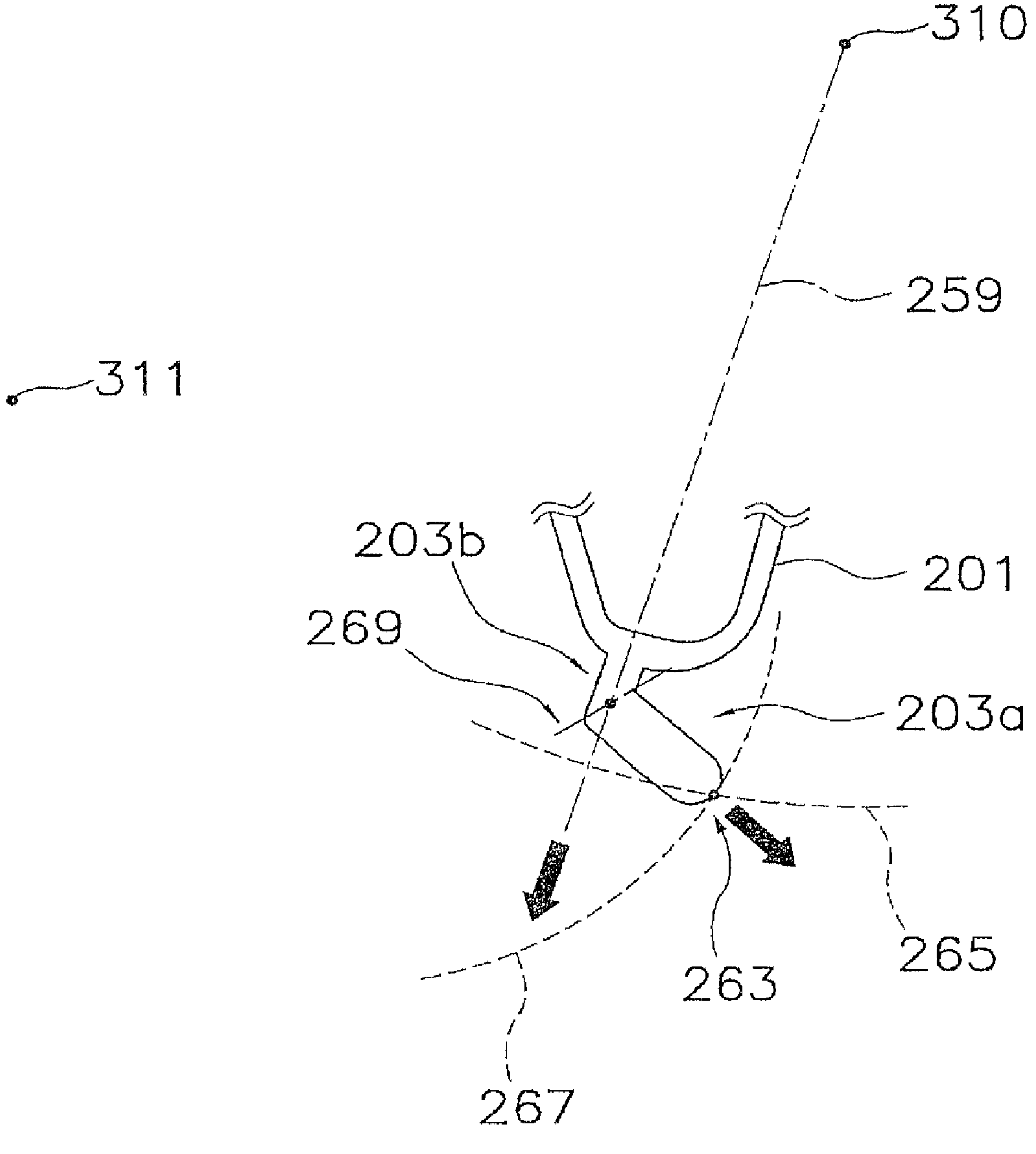
FIG. 12 is a related view of a first holding section and two axes of rotation.
Figure 15A:
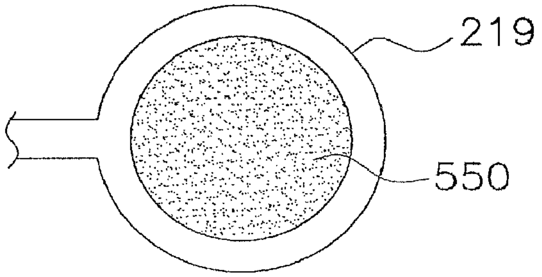
FIG. 15A is a view in which a reagent enclosed in a capsule has been placed in a reagent reservoir.
Figure 15B:
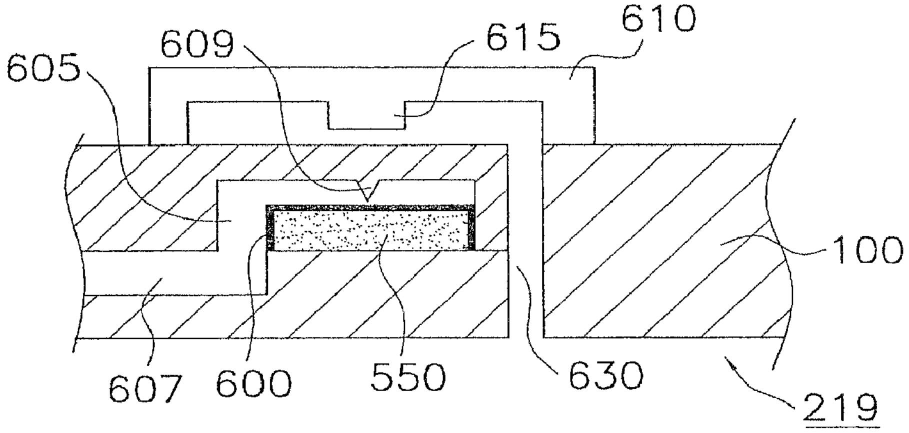
FIG. 15B is a schematic diagram (1) showing the reagent flowing out of the reagent reservoir.
Figure 15C:
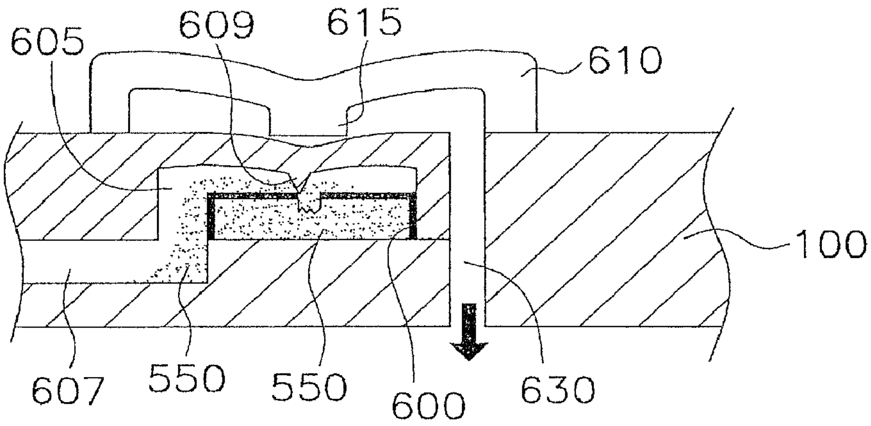
FIG. 15C is a schematic diagram (2) showing the reagent flowing out of the reagent reservoir.
Figure 16A:
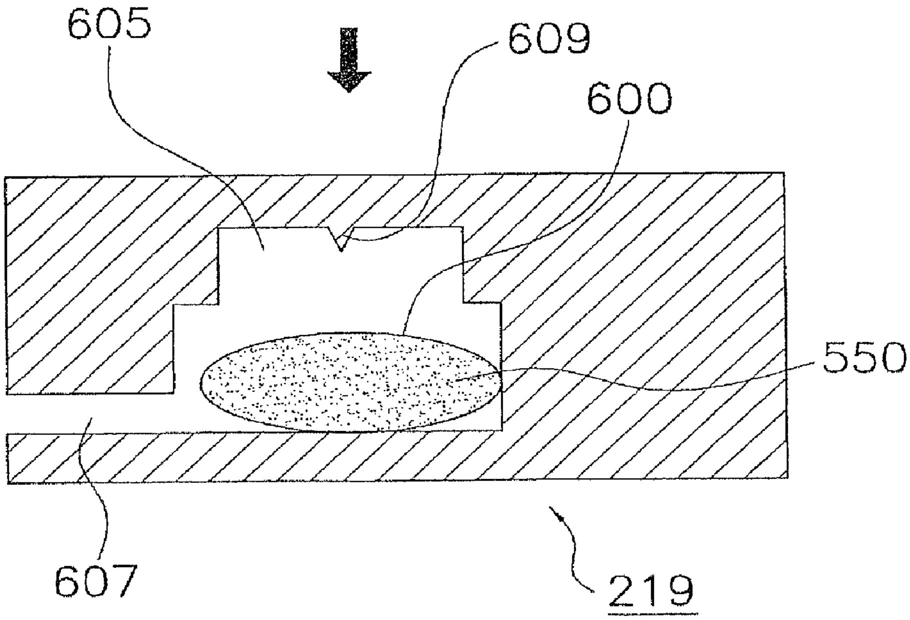
FIG. 16A shows an example (1) of a sectional view of a reagent reservoir.
Figure 16B:
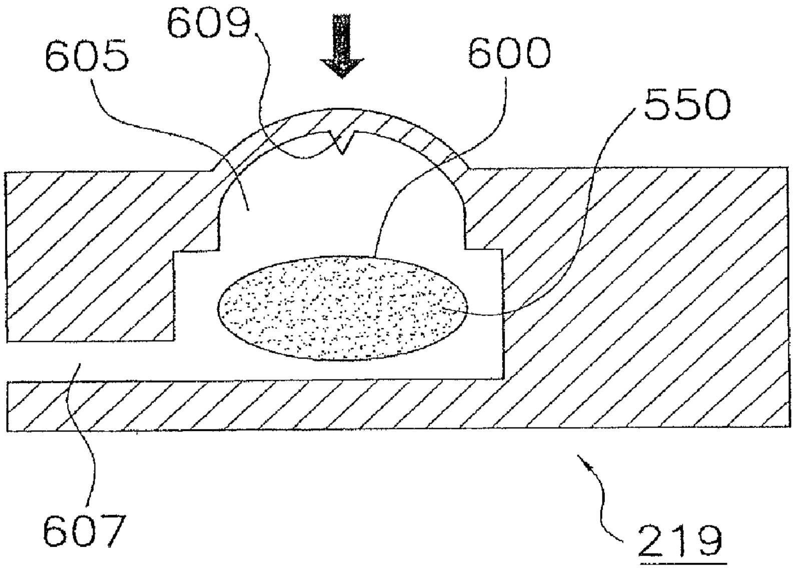
FIG. 16B shows an example (2) of a sectional view of a reagent reservoir.
Figure 17:
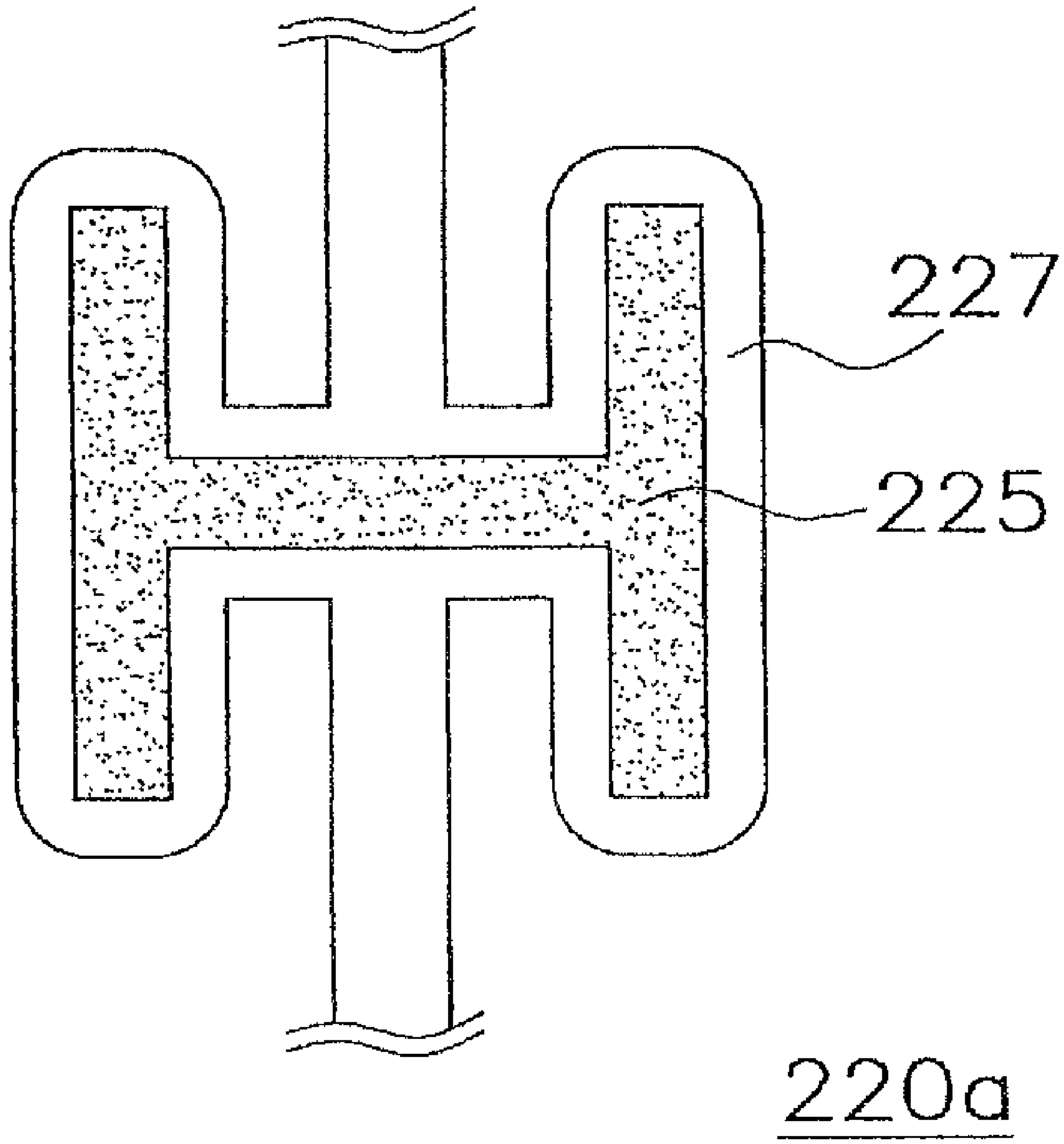
FIG. 17 is an enlarged drawing of a mixer section.
Figure 18A:
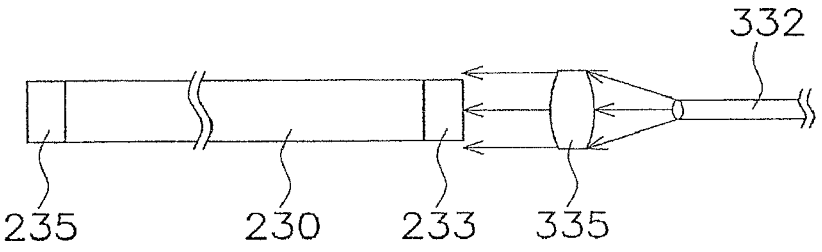
FIG. 18A shows an example (1) of a method of irradiating light in a photodetection path.
Figure 18B:
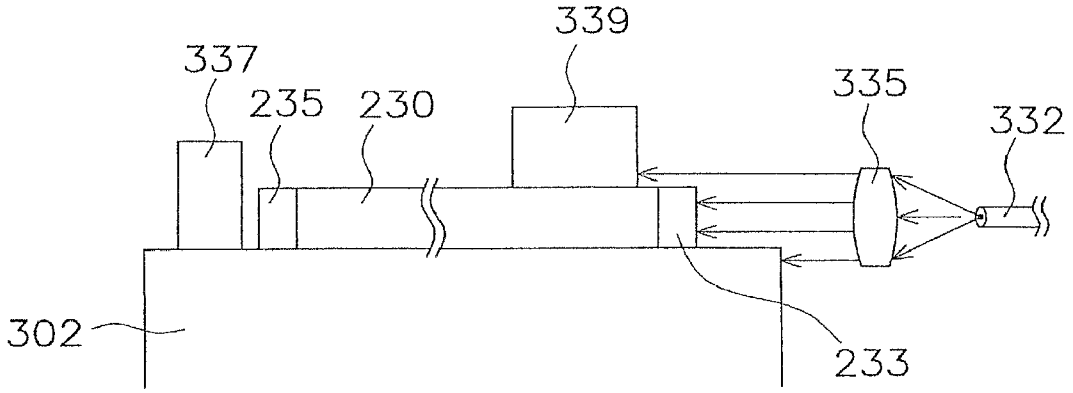
FIG. 18B shows an example (2) of a method of irradiating light in a detection path.

Next, the configuration of each portion of the test chip will be described in detail. FIG. 11 is view showing the relationship between each portion of the test chip of FIG. 8A and the two axes of rotation, FIG. 12 is a view showing the relationship between the first holding section 203 and the two axes of rotation, FIG. 13A and FIG. 13B are sectional views of an inlet, FIG. 14A to FIG. 14E are schematic diagrams of the structure of the first measuring section, FIG. 15A to FIG. 15C, and FIG. 16A and FIG. 16B, are sectional views of the reagent reservoir, FIG. 17 is an enlarged view of the mixer section, and FIG. 18A and FIG. 18B are examples of a light irradiation method in the photodetection path.

(3-1) Inlet

Figure 13A:
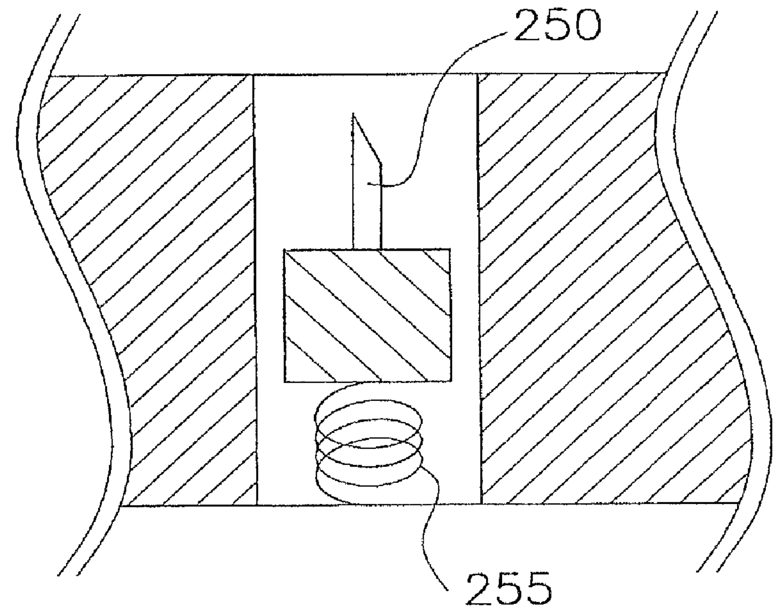
FIG. 13A is a sectional view of an inlet in an unused state.
Figure 13B:
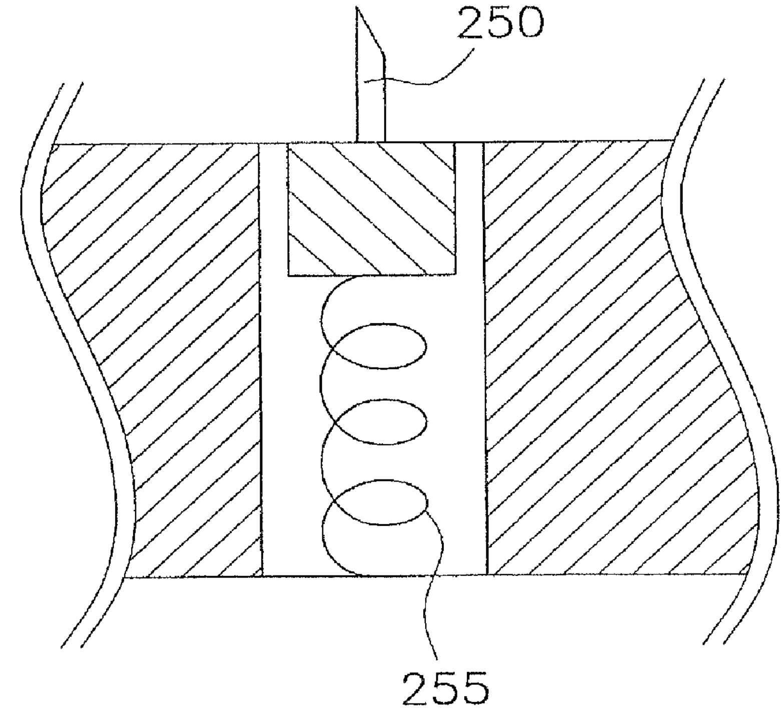
FIG. 13B is a sectional view of an inlet during use.

As shown in FIG. 13A and FIG. 13B, a sampling needle 250 for extracting a sample is connected with a spring 255 in the inlet 105, for example. With this sampling needle 250, the sample 500 that is the subject of testing will be introduced into the test chip 100. Sampling of the sample 500 into the inlet 105 with the sampling needle 250 is performed as follows. Here, except when sampling the sample 500, as shown in FIG. 13A, the spring 255 retracts so that the sampling needle 250 may be stored inside the inlet 105. When sampling the sample 500, as shown in FIG. 13B, the spring 255 extends and the sampling needle 250 projects from the inlet 105 to the sample 500 via the sampling needle 250. When the sampling of the sample 500 is performed with the sampling needle 250 in such a manner, the time and effort needed to introduce the sample 500 into the test chip 100 can be reduced. Contamination of the sample 500 at the time of introduction into the test chip 100 can also be eliminated. The inlet 105 may be connected with a hypodermic needle. Furthermore, a reservoir 241*b* of a regulation tube 241 described below may be provided with the ability to pump, and the sample 500 may be introduced into a centrifugal separation tube 201 and the regulation tube 241 via the inlet 105.

(3-2) Regulation Tube

The regulation tube 241 is connected to one open end portion of the substantially U-shaped centrifugal separation tube 201 together with the first measuring section 205. The inlet 105 is connected to the other open end portion of the centrifugal separation tube 201. Here, the regulation tube 241 has a first point and a second point in the regulation tube 241, and is formed so that the distance between the first point and the first axis of rotation 310 can be smaller than the distance between the second point and the first axis of rotation 310. At this point, in order to obtain the target component 510 first, the sample 500 is introduced into the centrifugal separation tube 201 and the regulation tube 241 connected to the centrifugal separation tube 201, and the centrifugal separation tube 201 and the regulation tube 241 are filled with the sample 500. When the chip is rotated around the first axis of rotation 310 in this condition, a larger centrifugal force than that at the first point of the regulation tube 241 is applied because the second point in the regulation tube 241 has a larger distance to the first axis of rotation 310. Accordingly, the sample 500 is separated bordering on the first point. That is, a sample on one side of the centrifugal separation tube 201 with respect to the first point is introduced into the centrifugal separation tube 201, and is centrifugally separated. On the other hand, a sample on one side of the regulation tube 241 with respect to the first point is introduced into the regulation tube 241. Accordingly, a substantially fixed amount of the target component 510 may be obtained from the fixed amount of the sample 500 filling the interior of the centrifugal separation tube 201.

The following design will be more preferable. The regulation tube 241 comprises a regulation tube connecting portion 241*a* (241*a* shown with a heavy line in FIG. 8A) for connecting the regulation tube 241 and the centrifugal separation tube 201, and a reservoir 241*b*. An end 241*a*, of the regulation tube connecting portion 241*a* (refer to FIG. 8A), that is, the connecting portion of the centrifugal separation tube 201 and the regulation tube connecting portion 241*a*, is designed so as to be located on the first axis of rotation 310 side with respect to the reservoir 241*b* (refer to FIG. 8A).

Figure 20:
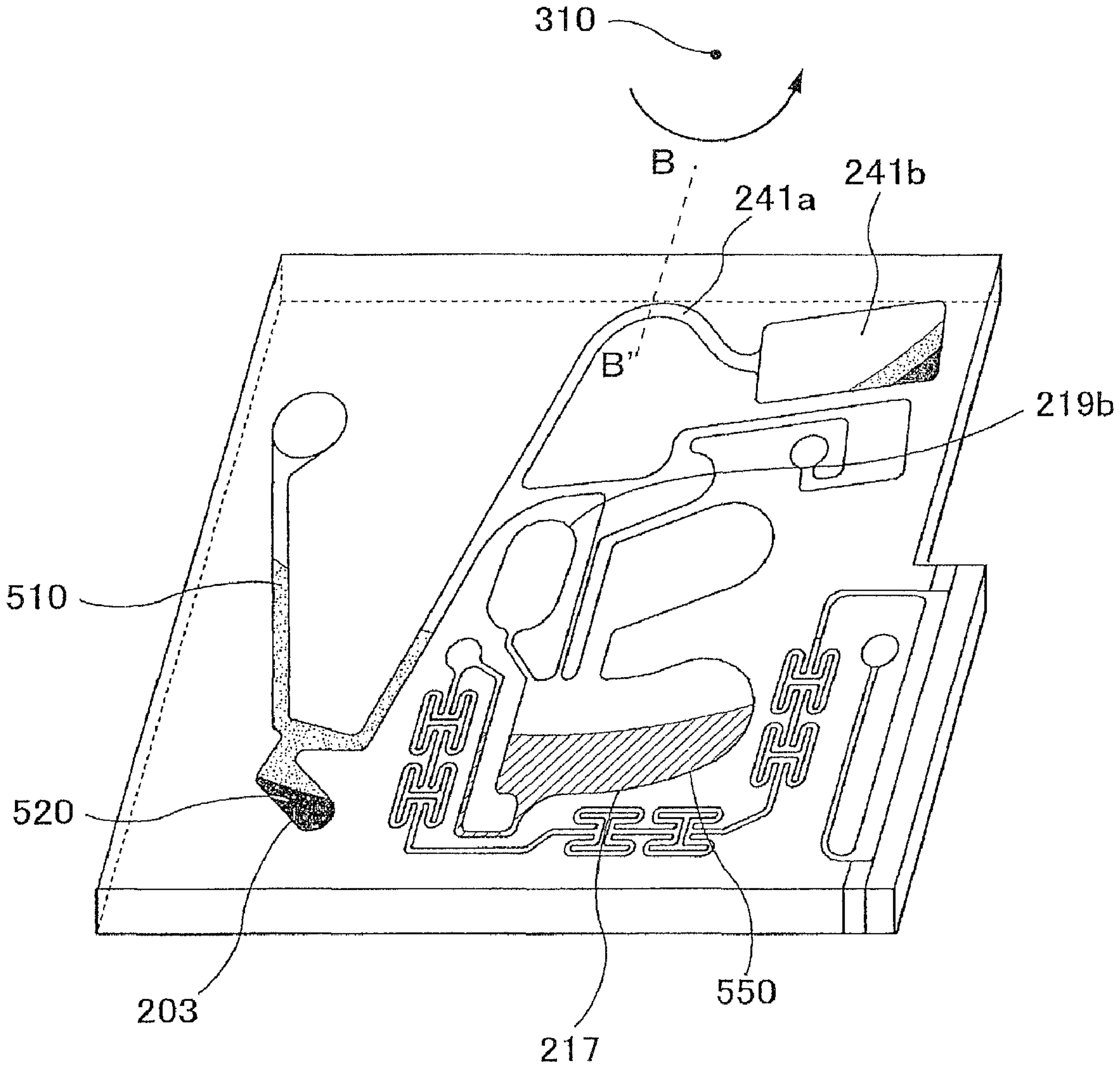
FIG. 20 shows an example (2) of a method for use of a test chip.
Figure 21:
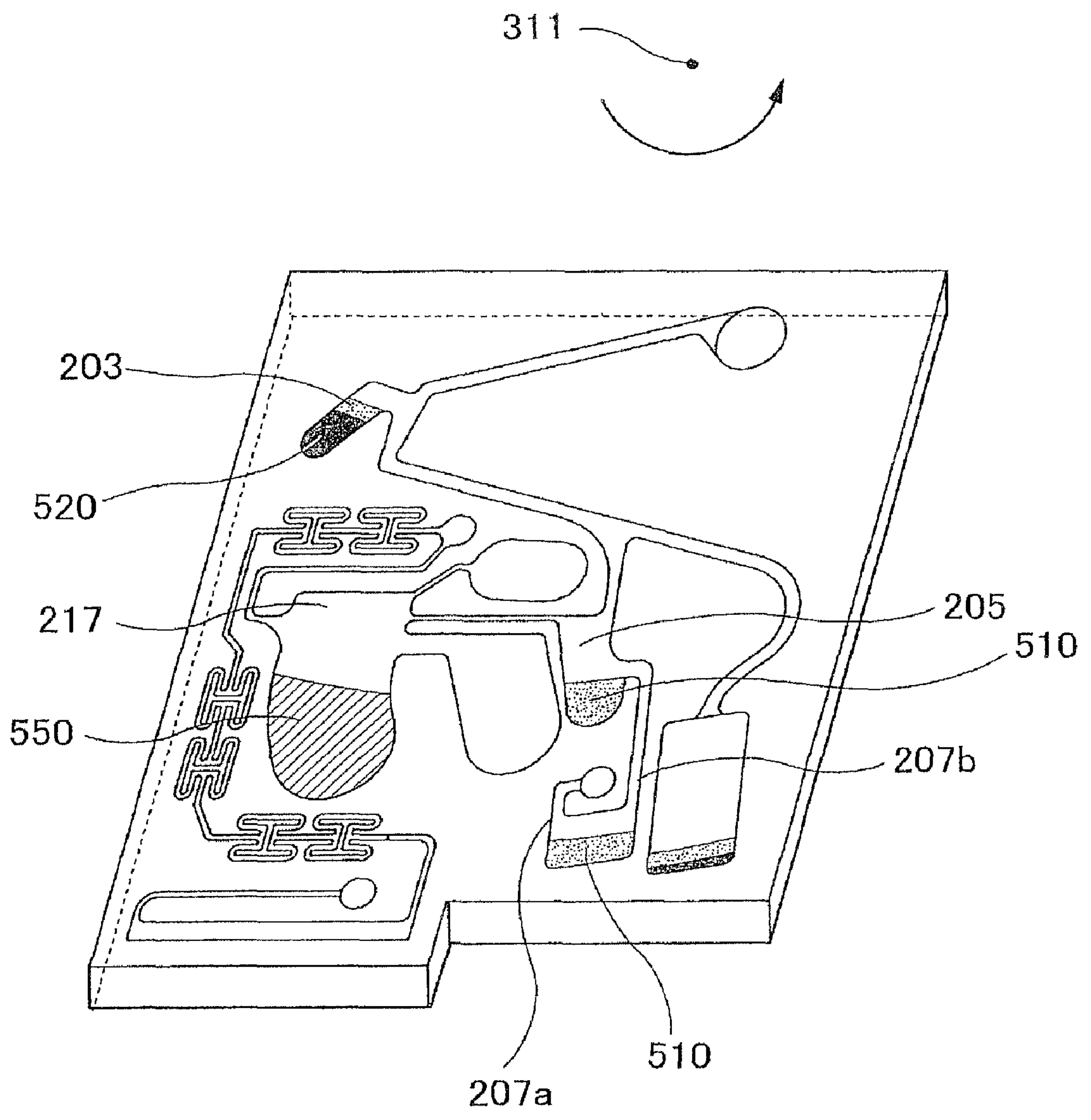
FIG. 21 is an example (3) of a method for use of a test chip.
Figure 22:
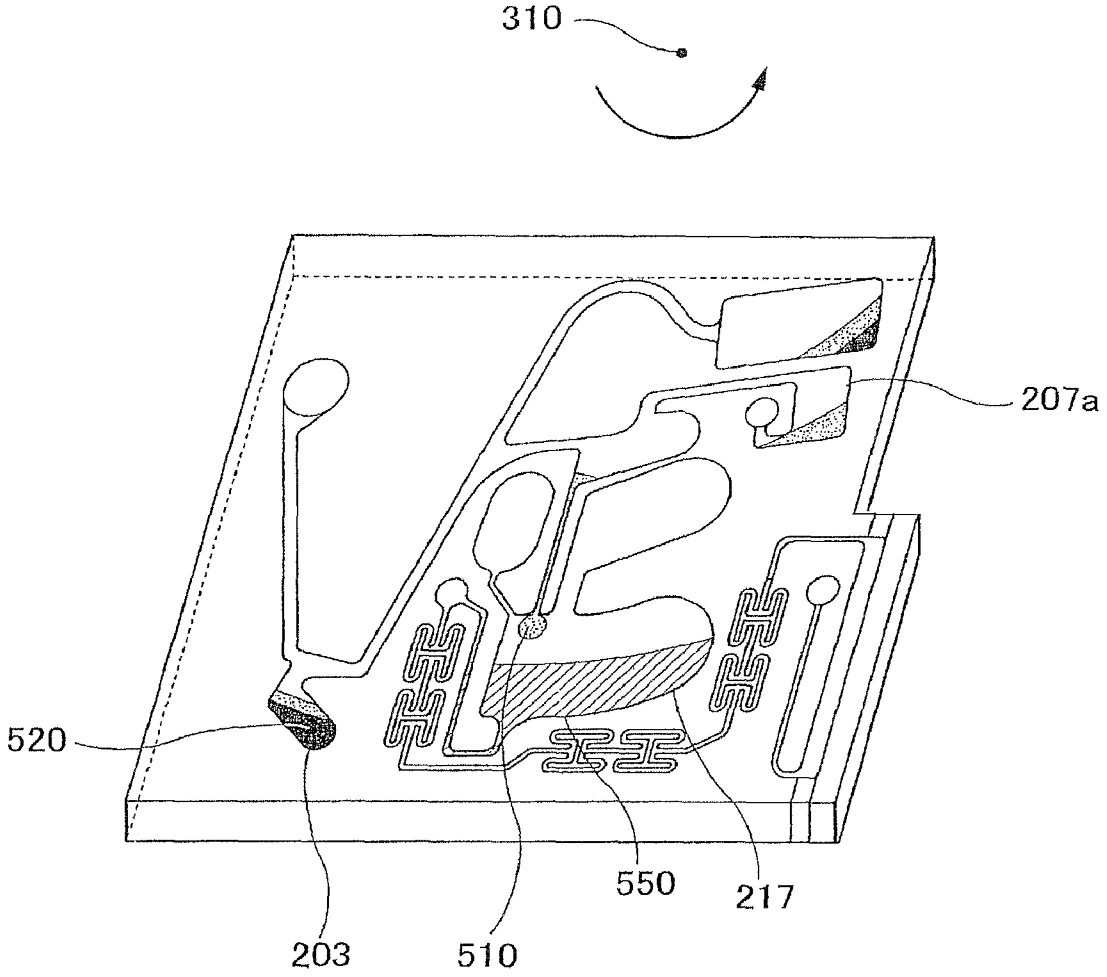
FIG. 22 is an example (4) of a method for use of a test chip.

Before performing centrifugal separation here, the sample 500 is introduced into the regulation tube 241 so as to fill the centrifugal separation tube 201 and the regulation tube connecting portion 241*a*. When the chip is rotated around the first axis of rotation 310 in this condition, the sample will be separated bordering on the end 241*a*' of the regulation tube connecting portion 241*a*. That is, as shown in FIG. 20 described below, on the one hand, the sample 500 on the centrifugal separation tube 201 side with respect to the end 241*a*' of the regulation tube connecting portion 241*a*' will be introduced into the centrifugal separation tube 201, and will be centrifugally separated. On the other hand, the sample on one side of the regulation tube 241 with respect to the end 241*a*' will be introduced into the reservoir 241*b*, and will be centrifugally separated. Accordingly, since the sample 500 may be introduced so as to fill the interior of the centrifugal separation tube 201 using the regulation tube 241, the amount of the sample 500 introduced may be adjusted to a fixed amount each time the sample 500 is introduced. Therefore, a fixed amount of the sample 500 may be centrifugally separated in the centrifugal separation tube 201. As described above, a substantially fixed amount of the target component 510 may be obtained from a fixed amount of the sample 500.

When the regulation tube connecting portion 241*a* is formed in a U-shape and has an opening in the side opposite the first axis of rotation 310, separation between the sample 500 in the regulation tube 241 and the sample 500 in the centrifugal separation tube 201 will be made easier.

(3-3) Centrifugal Separation Tube

A centrifugal separation tube 201 is connected to the inlet 105, and a sample 500 will be introduced from the inlet 105. The centrifugal separation tube 201 has a substantially U-shape, a first open end portion 2011 is connected to the first measuring section 205 having a predetermined volume, and a second open end portion 2012 is connected to the inlet 105.

When the centrifugal separation tube 201 is formed in a U-shape in this way, non-target components 520 are held in the first holding section 203 in the bottom of the U-shaped tube during the rotation around the first axis of rotation 310, and a target component 510 is located within the U-shaped tube, and therefore the target component 510 and the non-target components 520 may be separated. Next, since the non-target components 520 are held untreated in the first holding section 203 during rotation around the second axis of rotation 311, the target component located within the U-shaped tube extending to the first end portion 2011 in the first measuring section 205 side with respect to the bottom of the U-shaped tube and to another second end portion 2012 will be effectively introduced into the first measuring section 205. Accordingly, the target component in the sample 510 may be efficiently segregated.

Here, as shown in FIG. 11, a line 253 passing through the tube axis of the U-shaped centrifugal separation tube 201, and a line 251 passing through another tube axis, are set in the following manner. The section having the tube axis of centrifugal separation tube 201 coincident with the line 253 is connected to the first measuring section 205, and the section having the tube axis coincident with the line 251 is connected with inlet 105.

The distance of the line 251 from the second axis of rotation 311 becomes smaller as the line 251 extends from the bottom of the centrifugal separation tube 201 to the opening of the U-shape. For example, in FIG. 11, in L1 and L2 showing the distance between the line 251 and the second axis of rotation 311, the distance L1 between a distant point on the line 251 from the bottom of the centrifugal separation tube 201 and the second axis of rotation 311 is set to be smaller than L2. In contrast, the distance of the line 253 to the second axis of rotation 311 becomes larger as the line 253 extends to the opening from the bottom of the U-shaped centrifugal separation tube 201. That is, the centrifugal separation tube 201 is formed so that the distance to the second axis of rotation 311 may become narrower as it extends to the second end portion 2012 from the bottom. Accordingly, on the one hand, the target component 510 is sent in the direction extending to the bottom from the second end portion 2012 of the centrifugal separation tube 201 by rotation around the second axis of rotation 311. On the other hand, the centrifugal separation tube 201 is formed so that the distance to the second axis of rotation 311 may become larger as it extends from the bottom to the first end portion 2011 connected to the first measuring section 205. Accordingly, the target component 510 is sent in the direction extending to the first end portion 2011 from the bottom of the centrifugal separation tube 201 by rotation around the second axis of rotation 311, and thus the target component 510 is sent into the first measuring section 205. When the centrifugal separation tube 201 is formed as described above, the target component 510 is efficiently centrifugally separated by rotation around the first axis of rotation 310, and the separated target component 510 may be efficiently moved to the first measuring section 205 by rotation around the second axis of rotation 311.

Furthermore, the opening of the centrifugal separation tube 201 formed by the line 251 and the line 253 preferably has a larger dimension as it extends to the first axis of rotation 310 side. Since the opening of the centrifugal separation tube 201 is on one side of the first axis of rotation 310, the bottom is located in the peripheral side in the radial direction of a circle around the first axis of rotation 310. That is, the distance between a portion of the opening and the first axis of rotation

310 of the centrifugal separation tube 201 is smaller than the distance between the bottom of the centrifugal separation tube 201 and the first axis of rotation 310. At this point, the direction of the centrifugal force of the rotation around the first axis of rotation 310 is almost coincident with the direction from the opening of the U-shaped centrifugal separation tube 201 to the bottom. Accordingly, by rotation around the first axis of rotation 310, the largest centrifugal force will be applied at the bottom of the centrifugal separation tube 201. Therefore, the non-target components 520 other than the target component 510 efficiently move to the bottom of the centrifugal separation tube 201 from the sample 500, and thus the target component 510 may be efficiently separated from the sample 500.

When an angle θ made by the line 251 and the line 253 is designed so as to be no more than 90 degrees, as shown in FIG. 11, the opening of the U-shaped centrifugal separation tube 201 will be no more than 90 degrees, and therefore the area occupied by the centrifugal separation tube 201 on the measuring chip 100 may be made smaller, advantageously enabling miniaturization of the measuring chip.

And as shown in FIG. 11, the distance between the first end portion 2011, as a connecting portion of the centrifugal separation tube 201, to the first measuring section 205 and the first axis of rotation 310 is preferably smaller than the distance between the second end portion 2012 of the centrifugal separation tube 201 and the first axis of rotation 310. Then, the first end portion 2011 will be nearer to the first axis of rotation 310 than the second end portion 2012, and the introduction of the sample 500 to the first measuring section 205 may be prevented during rotation around the first axis of rotation 310. For the same reason, with the relationship with the inlet 105, the distance between the first end portion 2011 and the first axis of rotation 310 is preferably smaller than the distance between the central portion of the inlet 105 and the first axis of rotation 310. Here, in FIG. 11, an arc 257 is the radius around the first axis of rotation 310, and is the distance from the first axis of rotation 310 to the central part of inlet 105. At this point, the first end portion 2011 is located inside the arc 257 with respect to the first axis of rotation 310. That is, since the first end portion 2011 is closer to the first axis of rotation 310 than the inlet 105, introduction of the sample 500 to the first measuring section 205 may be prevented during the rotation around the first axis of rotation 310.

Here, each tangent to right and left tubes constituting the centrifugal separation tube 201 may be set so as to satisfy the same relationship as that between lines 251 and 253.

Furthermore, the centrifugal separation tube 201 is not limited to a U-shape, but it may simply be formed, for example, to have a cup shape as shown in FIG. 8B. At this point, the first holding section 203 and the centrifugal separation tube 201 are integrally formed, and more particularly, a holding section main unit 203*a*, and a holding section connecting tube 203*b* and centrifugal separation tube 201 to be described later are integrally formed. The first holding section 203 is formed so as to have an opening in the direction of the second axis of rotation 311, in order to avoid introduction of the non-target components 520 into the first measuring section 205 by rotation around the second axis of rotation 311. With the sample 500 introduced into the centrifugal separation tube 201 and the first holding section 203 that is integral with the centrifugal separation tube 201, the non-target components 520 in the sample 500 are introduced into the first holding section 203 by rotation around the first axis of rotation 311. The target component 510 in the supernatant fluid in the centrifugal separation tube 201 is then introduced into the first measuring section 11 by rotation around the second axis of rotation 311, and the same measurement as described above is performed. In addition, a regulation tube 241 may also be provided on the left side of the centrifugal separation tube 201, as shown in FIG. 8B.

(3-4) First Holding Section

Since the first holding section 203 is provided in the bottom of the U-shaped centrifugal separation tube 201, the non-target components 520 that moved to the bottom of the U-shape by means of centrifugal separation in the centrifugal separation tube 201 are introduced into the first holding section 203. Here, FIG. 12 is an enlarged view of the first holding section, and the first holding section 203 is, for example, formed from a holding section main unit 203*a* bordering on a broken line 269, and a holding section connecting tube 203*b* for connecting the holding section main unit 203*a* to the centrifugal separation tube 201. Each part of the first holding section 203 is designed in the following manner.

The tubular holding section connecting tube 203*b* is designed so that an extension line of a tube axis 259 of the holding section connecting tube 203*b* may intersect the first axis of rotation 310. Such a design makes the direction (the thick arrow along the tube axis 259 in FIG. 12) of the centrifugal force by rotation around first axis of rotation 310 almost coincident with the direction of the tube axis of the holding section connecting tube 203*b*. Accordingly, the non-target components 520 are efficiently introduced from the centrifugal separation tube 201 to the first holding section 203. Therefore, separation of the target component 510 and the non-target components 520 may be efficiently performed.

Preferably, the cross-sectional area of the holding section connecting tube 203*b*, that is the connecting portion of the first holding section 203 and the centrifugal separation tube 201, is formed so that it is larger than the cross-sectional area of the centrifugal separation tube 201. The cross-sectional area, as used herein, includes not only the cross-sectional area in the plane direction of the test chip 100, but also includes all directions. If the cross-sectional area of the holding section connecting tube 203*b* is formed to be large enough, air in the first holding section 203 will be efficiently removed from the first holding section 203 to the centrifugal separation tube 201 when the sample 500 and the non-target components 520 are introduced into the first holding section 203.

Furthermore, the holding section main unit 203*a* is preferably formed in the peripheral side of the radial direction of a circle around the first axis of rotation 310, and a circle around the second axis of rotation 311 with respect to the holding section connecting tube 203*b*. That is, the configuration is preferably designed in the following manner. In FIG. 12, an arc 265 is the radius around the first axis of rotation 310, and is defined by the distance from the bottom 263 of the holding section main unit 203*a* to the first axis of rotation 310. In addition, an arc 267 is the radius around the second axis of rotation 311, and defined by the distance from the bottom 263 to the second axis of rotation 311. At this point, the holding section main unit 203*a* is located on the peripheral side in the radial direction of the circles around the first axis of rotation 310 and around the second axis of rotation 311 with respect to the holding section connecting tube 203*b*. In other words, the distance between the holding section main unit 203*a* and the first axis of rotation 310 is longer than the distance between the holding section connecting tube 203*b* and the first axis of rotation 310, and the distance between the holding section main unit 203*a* and the second axis of rotation 311 is longer than the distance between the holding section connecting tube 203*b* and the second axis of rotation 311. Such a design makes the centrifugal force work in the direction of the holding section main unit 203*a* having a larger distance from the first axis of rotation 310 than the distance from the holding section connecting tube 203*b* (refer to the thick arrow extending in the direction of the tube axis 259 in FIG. 12) by rotation around the first axis of rotation 310. Accordingly, the non-target components 520 will be efficiently introduced into the holding section main unit. In addition, by means of the rotation around the second axis of rotation 311, the centrifugal force works in the direction of the holding section main unit 203*a* having a larger distance from the second axis of rotation 311 than the distance from the holding section connecting tube 203*b* (refer to the thick arrow extending in the direction of the bottom 263 from the second axis of rotation 311 in FIG. 12). Accordingly, the non-target components 520 that were introduced therein are held untreated in the holding section main unit 203*a*, and it will be difficult for the non-target components 520 to backflow from the holding section connecting tube 203*b* to the centrifugal separation tube 201. Therefore, reliable separation between the target component 510 and the non-target components 520, and efficient introduction of only the target component 510 to the first measuring section 205 may be ensured.

Here, when the sample 500 introduced into the test chip 100 is blood and the target component 510 is plasma, the centrifugal separation tube 201 and the first holding section 203 are preferably designed in the following manner in order to obtain a fixed amount of the plasma. Since hemocytes make up approximately 30 to 40% of blood, the centrifugal separation tube 201 and the first holding section 203 are designed so that the ratio of the volume of the first holding section 203 to the centrifugal separation tube 201 provides the relationship: centrifugal separation tube 201: first holding section 203=50%:50%, when the total volume of the centrifugal separation tube 201 and the first holding section 203 is defined as 100%. When the volume ratio satisfies the relationship: centrifugal separation tube 201: first holding section 203=60%:40%, substantially only the hemocyte component will be introduced in the first holding section 203, and therefore the plasma can preferably be centrifugally separated without any waste. For example, on the one hand, when the volume of the first holding section 203 is 50% or greater, more plasma in the blood will be introduced into the first holding section 203, leading to loss of the plasma component. On the other hand, when the volume of the first holding section 203 is 40% or greater, the corpuscle component will overflow from the first holding section 203, resulting in difficult separation of the plasma component.

(3-5) First Measuring Section, Waste Fluid Reservoir

The first measuring section 205 is connected to the centrifugal separation tube 201, a waste fluid reservoir 207, and a removing tube 209. The first measuring section 205 connected to one of the open end portions of the U-shaped centrifugal separation tube 201 is constituted of a measuring section connecting tube 205*b* as a connecting portion between the first measuring section 205 and the centrifugal separation tube 201, and a measuring section main unit 205*a* connected to the measuring section connecting tube 205*b*. In addition, a waste fluid reservoir 207 is constituted of a waste fluid reservoir connecting section 207*b* connecting the waste fluid reservoir 207 to the first measuring sections 205, and a waste fluid reservoir main unit 207*a* connected to the waste fluid reservoir connecting section 207*b*. Here, in the first measuring section 205, the measuring section connecting tube 205*b* is disposed on one side of the second axis of rotation 311, and the measuring section main unit 205*a* is disposed so that it is almost located on the peripheral side in the radial direction of a circle of a second axis of rotation 311 with respect to the measuring section connecting tube 205*b*.

Furthermore, the waste fluid reservoir connecting section 207*b* of the waste fluid reservoir 207 is connected so that a branch is formed from the side of the measuring section main unit 205*a* with respect to the bottom 205*a*' of the first measuring section 205 (refer to FIG. 8A) of the second axis of rotation 311. The waste fluid reservoir main unit 207*a* is connected so that it is located on the peripheral side in the radial direction of a circle around the second axis of rotation 311 with respect to the waste fluid reservoir connecting section 207*b*. Furthermore, this waste fluid reservoir main unit 207*a* is disposed so that it is located on the peripheral side in the radial direction of a circle around the first axis of rotation 310 with respect to the waste fluid reservoir connecting section 207*b*.

A target component 510 centrifugally separated in the centrifugal separation tube 201 is introduced into the first measuring section 205 by rotating the test chip 100 around the second axis of rotation 311. Since the waste fluid reservoir 207 is connected to the first measuring section 205 at this point, the target component 510 exceeding a predetermined volume of the first measuring section 205 will be introduced into the waste fluid reservoir 207. Therefore, introduction of the target component 510 into the first measuring section 205 can guarantee accurate measurement of the desired target component 510. In addition, the target component 510 introduced into the waste fluid reservoir main unit 207*a* by rotation around the second axis of rotation 311 is located in the peripheral side in the radial direction of a circle around the first axis of rotation 310 with respect to the waste fluid reservoir connecting section 207*b*, and therefore the target component 510 will not backflow to the first measuring section 205 by rotation around first axis of rotation 310. Accordingly, by rotation around the first axis of rotation 310, the target component 510 that was accurately measured from the first measuring section 205 may be introduced into the primary mixing section 217.

Furthermore, as shown in FIG. 11, when an extension line 271 that passes through the tube axis of the measuring section connecting tube 205*b* intersects the second axis of rotation 311, the rotation around the second axis of rotation 311 is almost coincident with the direction of the tube axis of the measuring section connecting tube 205*b*, and therefore the target component 510 can be efficiently introduced from the centrifugal separation tube 201 to the first measuring section 205 by rotation around the second axis of rotation 311.

Figure 14A:
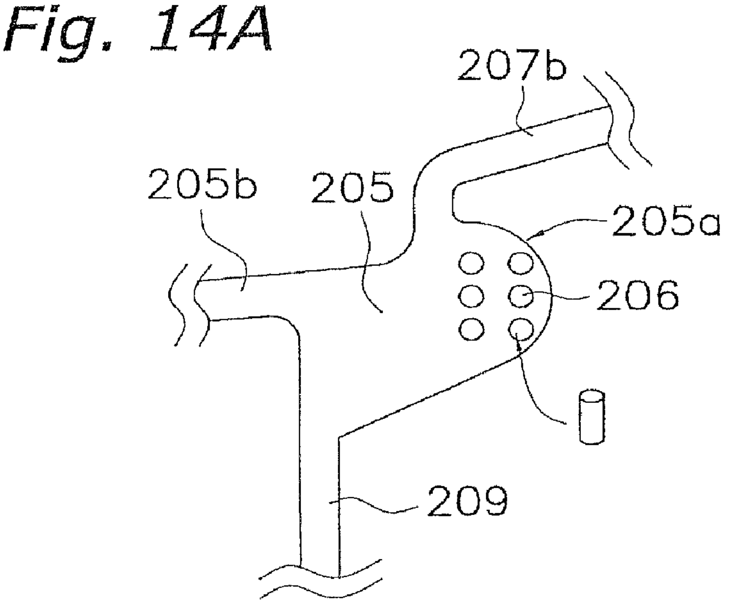
FIG. 14A is a schematic diagram (1) of the structure in a first measuring section.
Figure 14B:
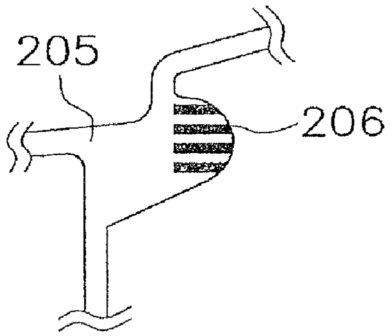
FIG. 14B is a schematic diagram (2) of the structure in a first measuring section.
Figure 14C:
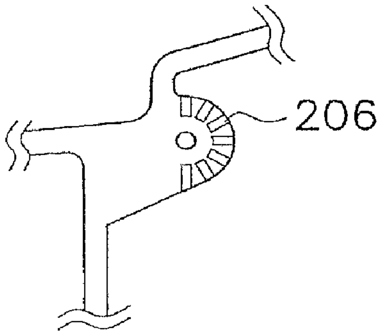
FIG. 14C is a schematic diagram (3) of the structure in a first measuring section.
Figure 14D:
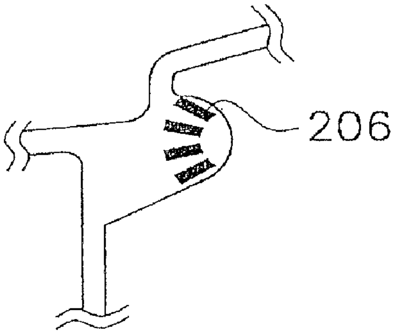
FIG. 14D is a schematic diagram (4) of the structure in a first measuring section.
Figure 14E:
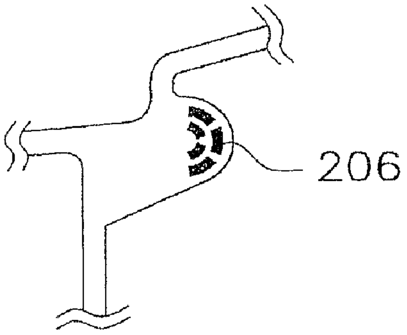
FIG. 14E is a schematic diagram (5) of the structure in a first measuring section.

In addition, when a passage wall contacting the target component 510, and the substrate of each portion, have an angle of contact smaller than 90 degrees with respect to the target component 510, a structure 206 is preferably provided in the measuring section main unit 205*a* of the first measuring section 205, as shown in FIG. 14A. When the structure 206 is thus provided, backflow of the target component 510 introduced from the centrifugal separation tube 201 into the centrifugal separation tube 201 may be prevented. The reason is that surface tension works between the target component 510 introduced into the measuring section main unit 205*a* having the structure 206 provided therein, and a surface of the structure 206. The structure 206 in the first measuring section 205 is not limited to a cylindrical pole 206 as shown in FIG. 14A, but structures as shown in FIG. 14B to FIG. 14E may be used. At this point, a design is provided in which the distance between adjoining structures 206 is smaller than the width of the channel in the test chip 100. That is, a design is provided in which the distance between adjoining structures 206 will be smaller than the width of the channel of the measuring section connecting tube 205*b*, the waste fluid reservoir connecting section 207*b*, and the removing tube 209 connected to the first measuring section 205.

In addition, as shown in FIG. 8A and FIG. 8B, the main unit 207*a* of the waste fluid reservoir of the waste fluid reservoir 207 is preferably formed in a U-shape having an opening in the side of the first axis of rotation 310. At this point, in the introduction of the target component 510 from the centrifugal separation tube 201 to the first measuring section 205, excessive target component 510 that has overflowed from the first measuring section 205 is introduced into the waste fluid reservoir main unit 207*a* from the first measuring section 205 by rotation around the second axis of rotation 311. Next, in removing the target component 510 from the first measuring section 205 by rotation around the first axis of rotation 310, the target component 510 introduced into the waste fluid reservoir main unit 207*a* is held untreated in the U-shaped main unit 207*a* of the waste fluid reservoir. The reason is that the waste fluid reservoir main unit 207*a* is formed in an approximate cup shape with respect to the first axis of rotation 310, and therefore backflow of the target component 510 from the waste fluid reservoir main unit 207*a* to the first measuring section 205 is prevented. Accordingly, the target component 510 that has been accurately measured may be removed from the first measuring section 205 via the removing tube 209.

(3-6) Removing Tube, Reagent Reservoir, Primary Mixing Section

The removing tube 209 is connected to first measuring section 205. The primary mixing section 217 is connected to the removing tube 209, and reagent reservoirs 219*a* and 219*b*. In addition, the first measuring section 205, the removing tube 209, and the primary mixing section 217 are located in this sequential order on the peripheral side in the radial direction of a circle around the first axis of rotation 310. Here, the removing tube 209 connected to the first measuring section 205 is disposed almost in the radial direction of a circle around the first axis of rotation 310 (refer to FIG. 11). Accordingly, the target component 510 introduced into the first measuring section 205 may be introduced into the primary mixing section 217 via the removing tube 209 by rotation around the first axis of rotation 310.

In addition, the reagent reservoir (219*a*, 219*b*) 219 is connected to the primary mixing section 217, and a reagent 550 is stored therein. The reagent 550 in the reagent reservoir 219 is introduced into the primary mixing section 217 by rotation around the first axis of rotation 310. A process will be advantageously simplified and accelerated when introduction of the reagent 550 from the reagent reservoir 219 to the primary mixing section 217 is concurrently performed with rotation during centrifugal separation, or rotation during introduction of the target component 510 from the first measuring section 205 to the primary mixing section 217. Here, the number of reagent reservoirs 219 need not be limited to one, and two or more reagent reservoirs may be provided in accordance with the items to be inspected.

In addition, when introduction of the reagent from the reagent reservoir 219 to the primary mixing section 217 is mainly performed by rotation around the first axis of rotation 310, the reagent reservoir 219 is preferably designed in the following manner. As shown in FIG. 8A, FIG. 8B, and FIG. 11 etc., the reagent reservoirs, connecting tubes 219*a*' and 219*b*' that are connecting portions of each of the reagent reservoirs 219*a* and 219*b*, and the primary mixing section 217, are disposed so as to be substantially along the radial direction of a circle around the first axis of rotation 310. Furthermore, a section having the reagent 550 to be introduced is formed on the side of the first axis of rotation 310 with respect to the reagent reservoir connecting tubes 219*a*' and 219*b*'. Thus, since the centrifugal force from the reagent reservoir 219 to the direction of the primary mixing section 217 works by rotation around the first axis of rotation 310 in this design, the reagent 550 may be efficiently introduced via the reagent reservoir connecting tube 219*a*', and 219*b*' to the primary mixing section 217. Furthermore, the reagent reservoir connecting tube 219*a*', and 219*b*' are located on the side of the second axis of rotation 311 with respect to the bottom 217' (shadow area of the primary mixing section 217 in FIG. 11) for the second axis of rotation 311 of the primary mixing section 217. At this point, the volume of the bottom 217' of the primary mixing section 217 is preferably formed to be larger than the total amount of the volume of 219*a* and 219*b* reagent reservoirs. In this design, the reagent introduced into the primary mixing section 217 by rotation around the first axis of rotation 310 from the reagent reservoir 219 does not backflow from the primary mixing section 217 to the reagent reservoir 219 by rotation around the second axis of rotation 311. At this point, if the volume of the bottom 217' of the primary mixing section 217 is preferably not less than 1.5 times of the total amount of the volume of the reagent reservoirs 219*a* and 219*b*, a backflow may be effectively prevented.

In addition, in the reagent reservoir 219, the reagent 550 may also be in a capsule as in the following manner. FIG. 15A is a plan view showing a condition in which the reagent enclosed in the capsule is disposed in the reagent reservoir, and FIG. 15B and FIG. 15C are schematic diagrams showing conditions in which the reagent flows out of the reagent reservoir.

Provided in the reagent reservoir 219 section of the test chip 100 are a space 605 for placing a capsule 600 with the reagent 550 enclosed therein, a reagent introductory section 607 for introducing the reagent 550 to the primary mixing section 217, a lid part 610, and a suction opening 630 for applying pressure to the lid part 610. In addition, a projection 609 is provided in a position facing the reagent 550 in the test chip 100 forming the space 605. The lid part 610 for covering the reagent reservoir 219 is provided in an upper part of the space 605. The lid part 610 has a pressing section 615 in a position facing the projection 609. When pressure in the direction in which the capsule 600 is pushed on the lid part 610 is not applied, the capsule 600 is not yet broken by the projection 609, as shown in FIG. 15B. On the other hand, for example, the projection 609 will be pushed by the pressing section 615 when a air suction between the lid part 610 and the test chip 100 works via the suction opening 630 to apply pressure to the reagent reservoir 219 in the direction of the capsule 600. And as shown in FIG. 15C, the projection 609 breaks through the capsule 600 to force the reagent 550 to flow out of the capsule 600. The reagent 550 that has flowed out is then introduced into the primary mixing section 217 from a reagent introductory section 607 connected to the primary mixing section 217. Since such a configuration enables maintenance of the reagent 550 in the capsule 600, and contact of the reagent 550 with the exterior may be avoided. Accordingly, pH change due to the dissolution of carbon dioxide in air, and degradation of enzymes and coloring matter by means of light may be prevented. The lid part 610 may also be pressed from the outside to push and break the capsule 600. Furthermore, as shown in FIG. 16A and FIG. 16B, the capsule 600 may be pushed and broken by pressing from the upper side of the test chip 100 onto the reagent reservoir 219 having the projection 609 provided thereto. As shown in FIG. 16B, when a section having the projection 609 provided thereto has a projection on the test chip 100 surface, the area to be pressed will preferably be clear. As materials of the capsule 600, an aluminum-plastic composite is preferably used.

(3-7) Secondary Mixing Section

A secondary mixing section 220 is connected to the primary mixing section 217, and performs further mixing of a mixed substance 560 obtained by mixing the target component 510 and the reagent 550 in the primary mixing section 217. The secondary mixing section 220 has a mixer section 220*a* connected in a plurality of stages. The mixer section 220*a* is constituted as shown, for example, in FIG. 17. The mixer section 220*a* has an H-shaped wall 225, and a micro channel 227 is formed so as to encircle the H-shaped wall 225. Such a fine micro channel 227 can improve the degree of integration of the secondary mixing section 220, and therefore the size of the test chip 100 may be reduced.

(3-8) Photodetection Path, Light Inlet, Light Outlet, and Outlet

The mixed substance 560 obtained by mixing of the reagent 550 and the target component 510 in the secondary mixing section 220 is introduced into the photodetection path 230. A light is introduced into the photodetection path 230 from the light inlet 233, and after passing through the inside of the photodetection path 230, exits from the light outlet 235. Determination of the target component 510 is performed by measurement of the transmitted quantity of the light. The photodetection path 230 is preferably coated with materials having a high light reflectivity, such as Al. In addition, the light inlet 233 and the light outlet 235 make optical waveguides. Materials having a refractive index higher than that of an upper board and a lower board may be used, and will enable easier collection of light. In addition, in ultraviolet light measurement, materials having an ultraviolet light transmittance higher than that of the upper and lower board may be used. For example, after formation of each section other than the optical waveguide of the light inlet 233 and the light outlet 235 in the upper and lower board, the light inlet 233 and the light outlet 235 are prepared by molding of the upper and lower board by injection molding.

Although in the first embodiment, as is shown in FIG. 8A, FIG. 8B, and FIG. 10, light is irradiated from the side face of the substrate into the photodetection path 230, the light may also be irradiated from the upper and lower direction of the substrate. In addition, as shown in FIG. 18A, light from an optical fiber or an LED that has been converted into parallel light may also be introduced into the light inlet 233 as an optical waveguide. FIG. 18A is a view showing the relationship between the photodetection path 230 provided in the test chip 100, and incident light from the optical fiber 332. Light from the optical fiber 332 is converted into a parallel beam by a lens 335. Thus, by adjusting the travel direction of the light with respect to the direction along the photodetection path 230 using a parallel light beam to secure a fixed luminous flux, the light may be efficiently introduced into the entire light inlet 233.

Furthermore, as shown in FIG. 18B, a light shielding material 339 is preferably provided in the detecting device 302 in order to avoid entry of light from outside the test chip 100 to a light receiving element 337 for receiving light. The light shielding material 339 provided in the detecting device 302 is, for example, disposed on an upper surface of the test chip 100, and it works so that light from an optical fiber 332, and light from the optical fiber 332 converted into a parallel beam by a lens 335, may be irradiated only to the photodetection path 230.

Method for Use of the Test Chip

FIG. 19 to FIG. 25A, FIG. 25B, and FIG. 25C, will be hereinafter used to describe a method for use of the test chip 100 when a target component 510 is to be determined from a sample 500.

Figure 25A:
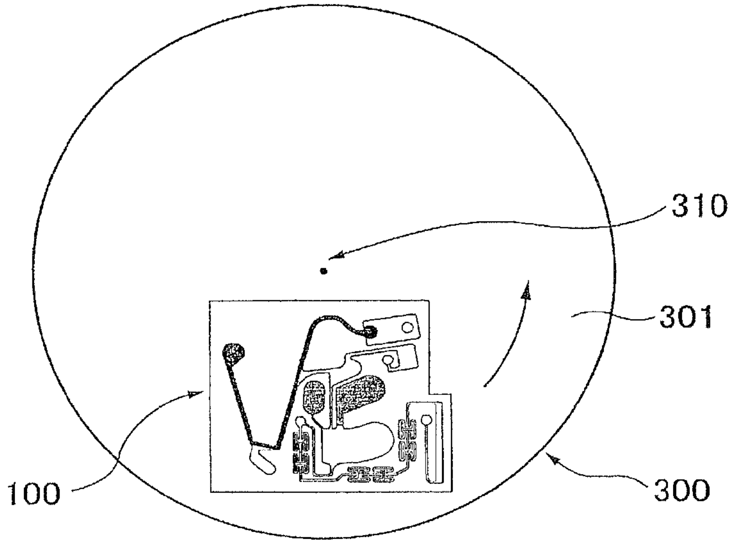
FIG. 25A is a related view of an rotation apparatus and a test chip with a test chip laid thereon.

Step 1:

First, as shown in FIG. 25A, a test chip 100 is fixed on a rotating platform 301 so that the center of rotation of the rotating platform 301 on an apparatus 300 is coincident with a first axis of rotation 310. A sample 500, such as a blood sample, is extracted using a sampling needle 250 with spring 255 loaded therein. Next, determination of the sample 500 is performed as follows.

Figure 19:
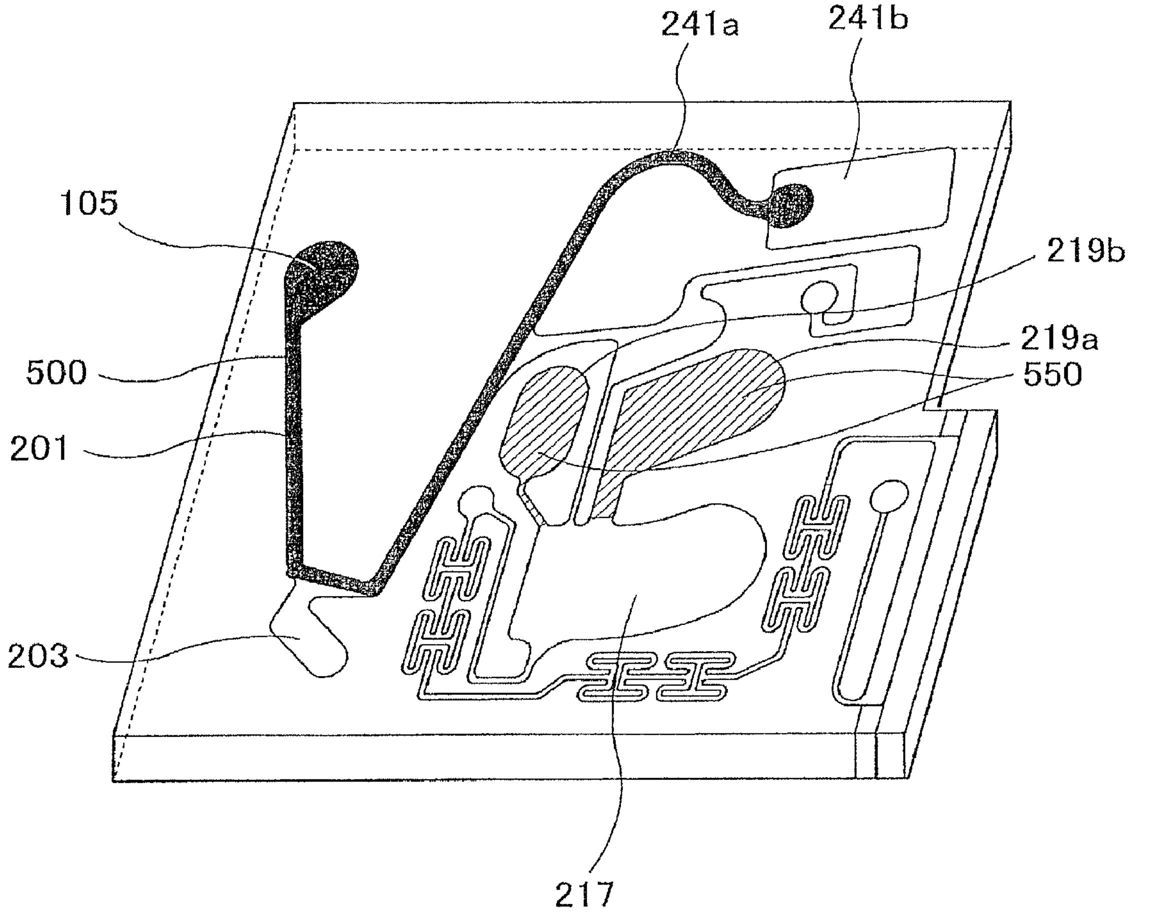
FIG. 19 shows an example (1) of a method for use of a test chip.

Step 2:

Next, the sample 500 is introduced so that a centrifugal separation tube 201 and a regulation tube connecting portion 241*a* of a regulation tube 241 may be filled (refer to FIG. 19).

Step 3:

Subsequently, the rotating platform 301 is rotated. At this point, as shown in FIG. 25(*a*), the test chip 100 is placed on the rotating platform 301 so that the center of rotation of the rotating platform 301 may be coincident with a first axis of rotation 310. Accordingly, when the rotating platform 301 is rotated in this condition, the test chip 100 will rotate around the first axis of rotation 310. By this rotation around the first axis of rotation 310, as shown in FIG. 20, centrifugal separation is performed bordering on a boundary B-B' of the regulation tube connecting portion 241*a* and the centrifugal separation tube 201, that is, the end portion 241'. In other words, on the one hand, the sample 500 on the side of the centrifugal separation tube 201 with respect to the boundary B-B' is introduced into the centrifugal separation tube 201 to be centrifugally separated. On the other hand, the sample on the side of the regulation tube 241 with respect to the boundary B-B' is introduced into the reservoir 241*b*. Here, by rotation around the first axis of rotation 310, the centrifugal force works in the direction of the bottom from the opening of the centrifugal separation tube 201. Accordingly, non-target components 520 other than the target component 510 in the sample 500 move to the bottom of the centrifugal separation tube 201, are introduced into the first holding section 203, and held there. Thus, the target component 510 is centrifugally separated from the sample 500 (refer to FIG. 20).

Step 4:

Furthermore, a reagent 550 is introduced into the primary mixing section 217 from a reagent reservoir 219 by rotation of the test chip 100 around the first axis of rotation 310 (refer to FIG. 20).

Figure 25B:
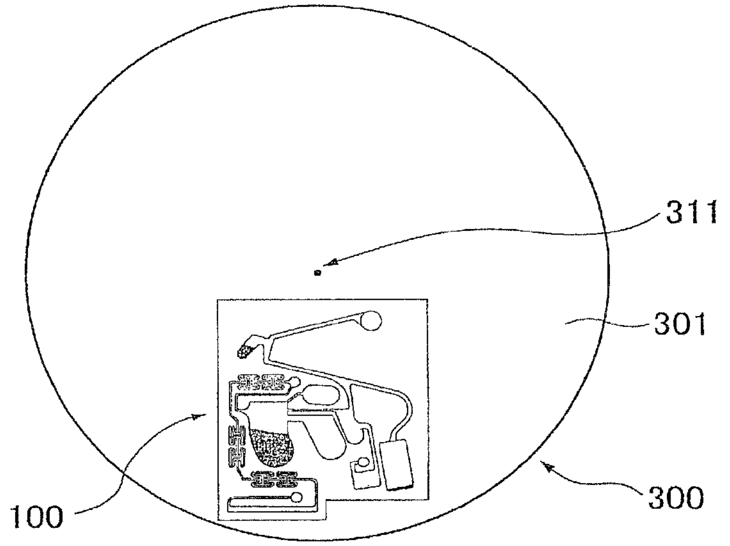
FIG. 25B is a related view of an rotation apparatus and a test chip when the test chip is rotated from a condition of FIG. 25A.

Step 5:

Next, as shown in FIG. 25B, the test chip 100 itself is rotated at a predetermined angle, and the center of rotation of the rotating platform 301 is made coincident with a second axis of rotation 311. The predetermined angle is an angle made by the first axis of rotation 310 and the second axis of rotation 311. The rotating platform 301 is rotated, and the test chip 100 is rotated around the second axis of rotation 311. The target component 510 centrifugally separated in step 3 is introduced into a first measuring section 205 from the centrifugal separation tube 201 by this rotation around the second axis of rotation 311 (refer to FIG. 21). Here, the target component 510 exceeding a predetermined volume of the first measuring section 205 is introduced into the waste fluid reservoir main unit 207*a* from the waste fluid reservoir connecting section 207*b* connected to the first measuring section 205. In addition, the non-target components 520 introduced into the first holding section 203 in step 3 are held untreated in the first holding section 203. Therefore, in removing the target component 510 to the first measuring section 205, contamination of the non-target components 520 into the target component 510 is inhibited. In this way, the target component separated in the centrifugal separation tube may be effectively removed into the first measuring section 205, and only the desired target component 510 will be accurately measured in the first measuring section 205.

Figure 25C:
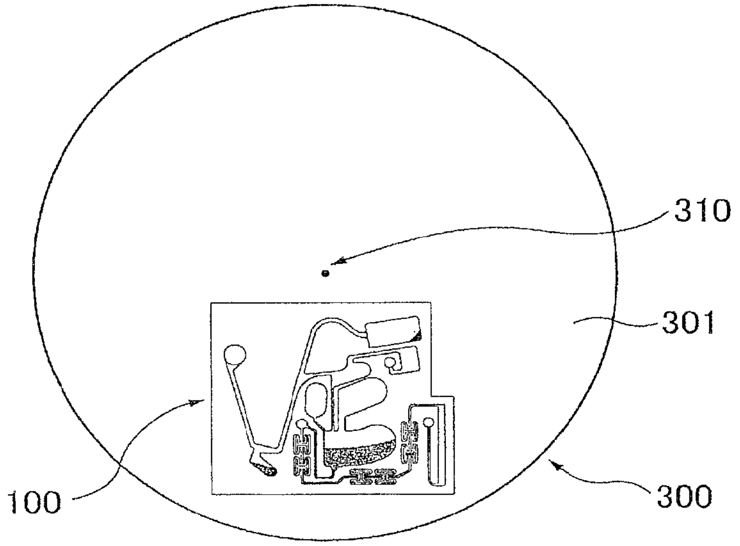
FIG. 25C is a related view of an rotation apparatus and a test chip when the test chip is rotated from the state shown in FIG. 25B.

Step 6:

Next, as shown in FIG. 25C, the test chip 100 itself is rotated by a predetermined angle, and the center of rotation of the rotating platform 301 is made coincident with a second axis of rotation 310. The test chip 100 is rotated around the first axis of rotation 310, and the target component 510 in the first measuring section 205 is introduced into the primary mixing section 217. Furthermore, in the primary mixing section 217, the target component 510 and the reagent 550 are mixed by rotation around first axis of rotation 310, to obtain a mixed substance 560 (refer to FIG. 22).

When introduction of the target component 510 to the primary mixing section 217 from the first measuring section 205, and mixing of the target component 510 and the reagent 550 in the primary mixing section 217, are simultaneously carried out in the same rotation, handling of the test chip 100 will be easier, and the mixed substance 560 will be quickly be obtained.

Figure 23:
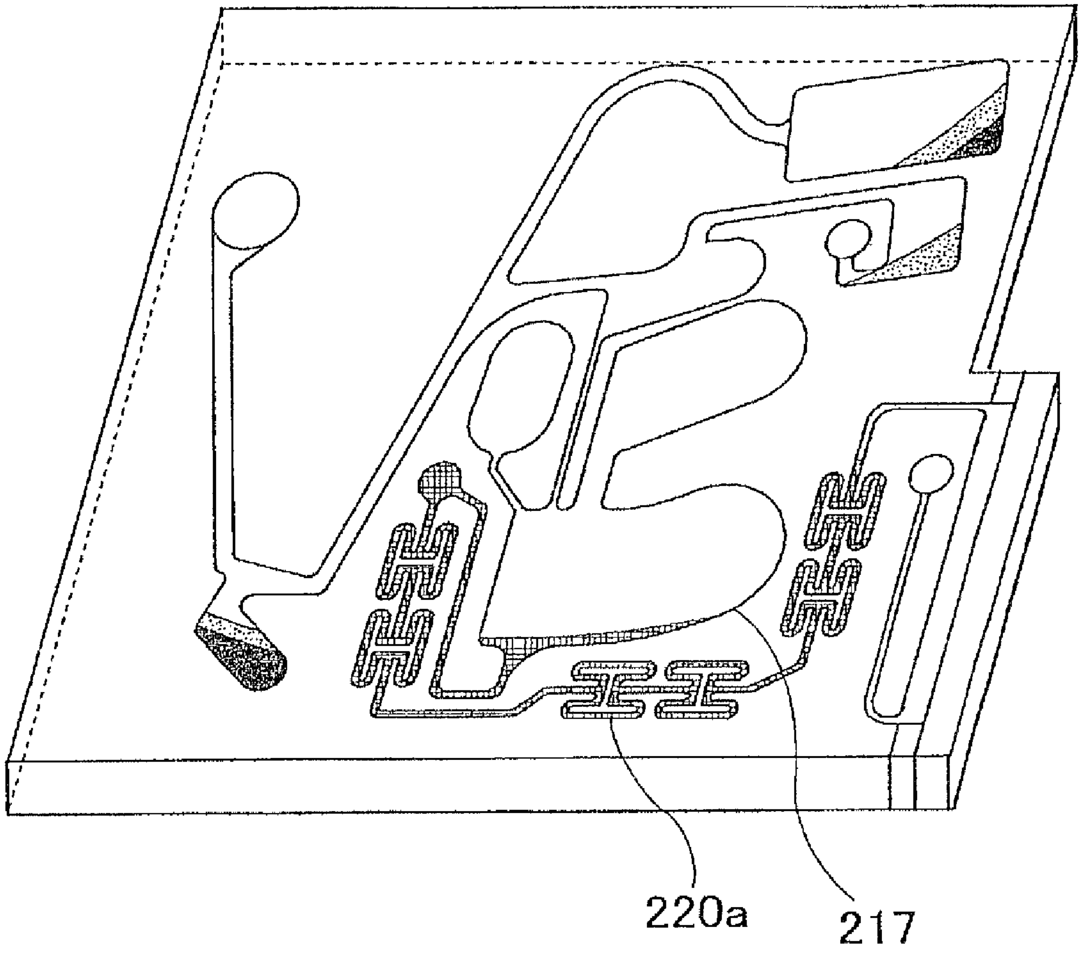
FIG. 23 shows an example (5) of a method for use of a test chip.
Figure 24:
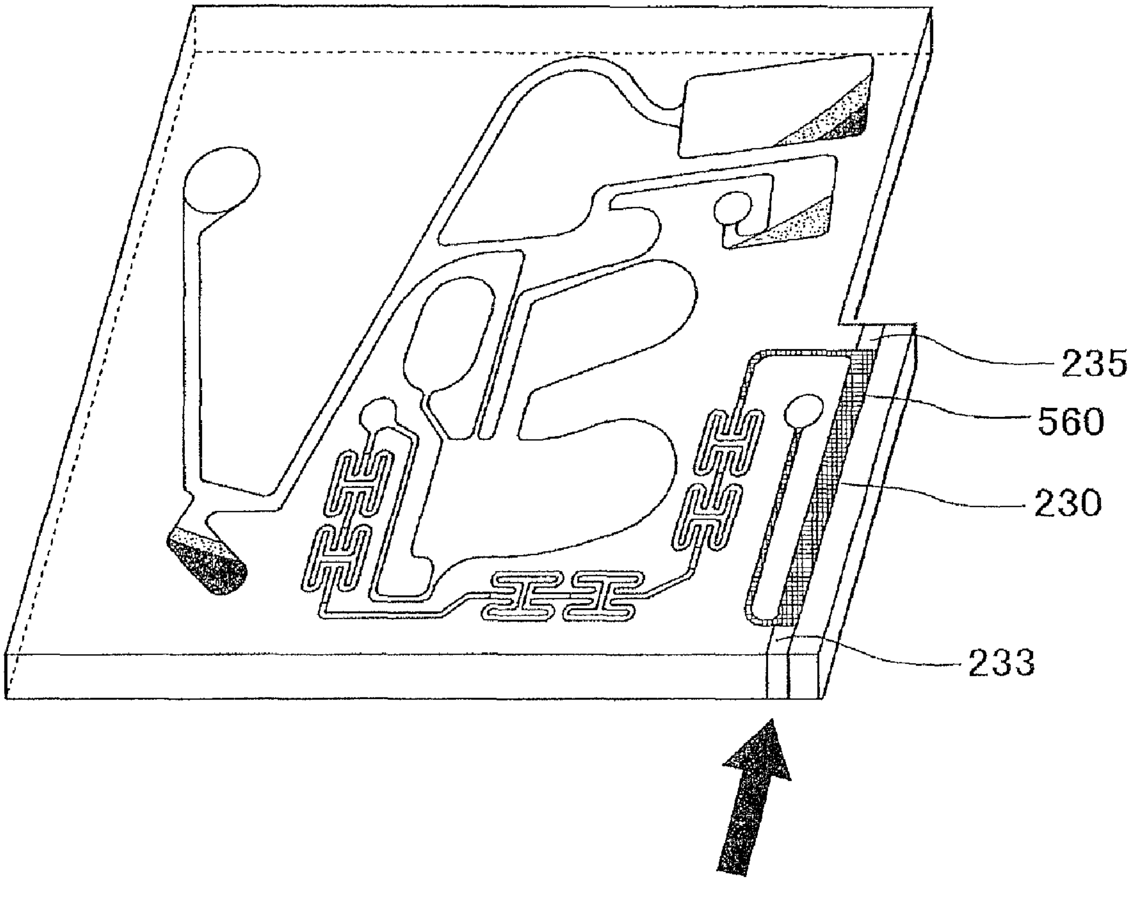
FIG. 24 shows an example (6) of a method for use of a test chip.

Step 7:

The mixed substance 560 obtained by mixing the target component 510 with the reagent 550 in the primary mixing section 217 is introduced into a secondary mixing section 220, and further mixing will be performed (refer to FIG. 23).

Step 8:

The mixed substance 560 is introduced into a photodetection path 230. Light is introduced into the photodetection path 230 from a light inlet 233, and after passing through the inside of the photodetection path 230, will exit via a light outlet 235. Determination of the target component 510 is performed by measuring the transmitted quantity of this light (refer to FIG. 24).

The step for introducing the reagent 550 in step 4 may be concurrently carried out at the time of separation of the target component 510 in the centrifugal separation tube 201 in step 3, at the time of introduction to the first measuring section 205 of the target component 510 in step 5, and at the time of introduction to the primary mixing section 217 of the target component 510 in step 6. By concurrently introducing the reagent 550, the mixed substance 560 will be quickly obtained.

Effects

The above-described handling of the test chip 100 having the introduced sample 500 enables collective processing of separation, measuring, mixing with the reagent, and determination of the target component 510 in the sample 500 using the first axis of rotation 310 and the second axis of rotation 311. In addition, since the non-target components 520 are held in the first holding section 230, contamination of the non-target components 520 in the target component 510 will be inhibited during the removal of the target component 510 to the first measuring section 205, and therefore the target component 510 separated in the centrifugal separation tube 201 may be effectively removed to the first measuring section 205. Accordingly, separation and measurement of the target component 510 can be efficiently performed. Furthermore, as described above, switching of the first axis of rotation 310 to the second axis of rotation 311, and the second axis of rotation 311 to the first axis of rotation 310, enables separation, measuring, and determination of the sample 500, leading to implementation of a simpler process.

At this point, the first measuring section 205 has a predetermined volume, and can measure accurately the target component 510 introduced from the centrifugal separation tube 201. Accordingly, the mixed substance 560 of the reagent 550 and the target component 510 having a desired mixing ratio may be obtained. Since separation and measurement of the target component are performed by only the rotation of the test chip 100 as described above, connection of the test chip 100 with an apparatus, such as a pump, will not be needed for separation and measurement, allowing simplification of the entire structure of the apparatus having the test chip 100 placed thereon. In addition, the sample 500 is not removed out of the test chip 100 until the target component 510 is determined, allowing a reduction in contamination of the target component 510 and accurate determination of the target component 510.

Figure 26:
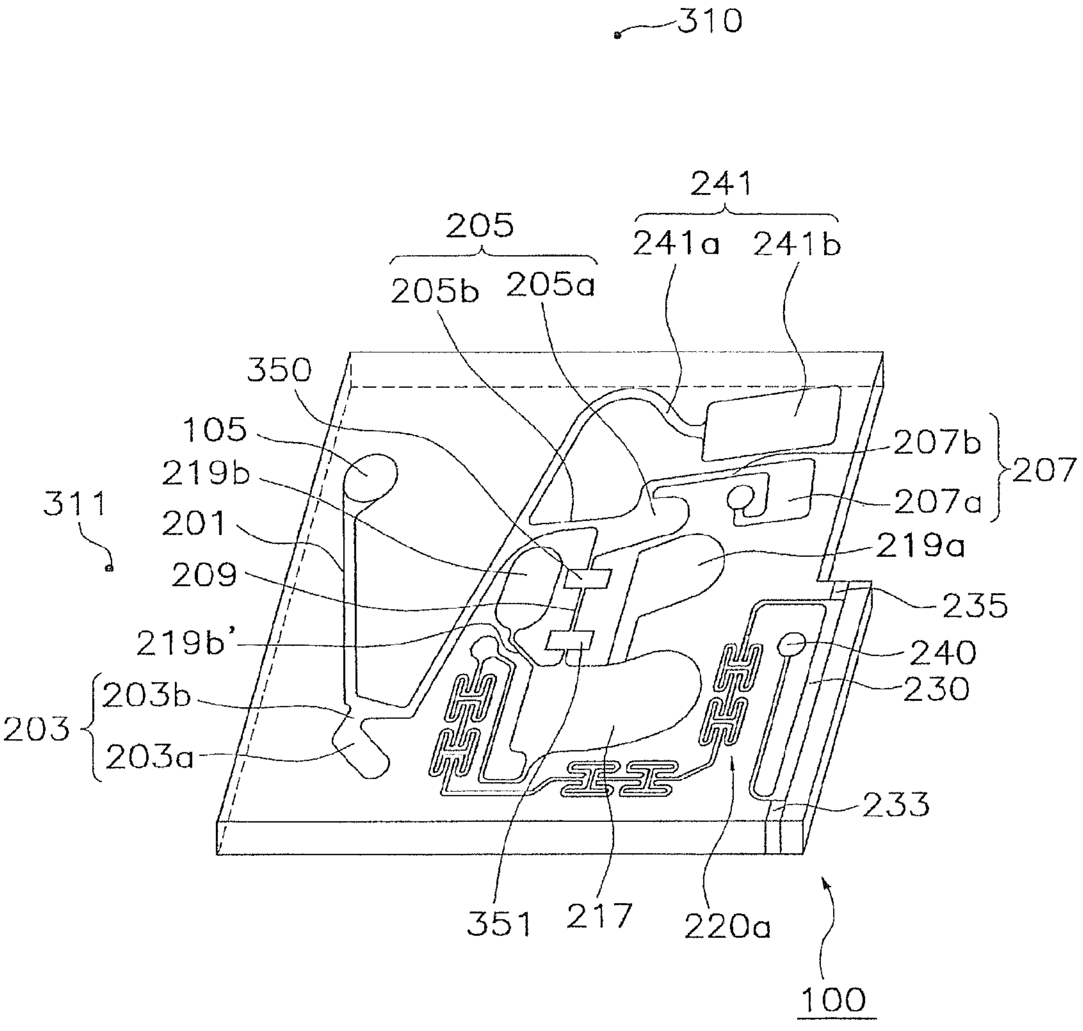
FIG. 26 is a perspective view of a test chip having an aluminum valve.

Furthermore, since separation, measuring, mixing, and determination may be performed in one chip, miniaturization of the test chip 100 may be achieved. Moreover, aluminum valves 350 and 351 are preferably provided in a removing tube 209, as shown in FIG. 26. Aluminum valves 350 and 351 are designed to have a channel width that is wider than that of the removing tube 209. The aluminum valve 350 is adjacent to the first measuring section 205, and the aluminum valve 351 is adjacent to the primary mixing section 217. The aluminum valve 350 prevents leakage of the target component 510 introduced into the first measuring section 205 from the first measuring section 205. The reason is that the surface area of the target component 510 becomes smaller, and the free energy is made smaller, when the target component 510 in the first measuring section 205 contacts the aluminum valve 350 having a larger channel width than that of the first measuring section 205. In addition, the aluminum valve 351 prevents backflow of the target component 510 from the primary mixing section 217 to the first measuring section 205 introduced into the primary mixing section 217 for the same reason as mentioned above. The position of this aluminum valve is not limited to the above mentioned position, but it may also be provided in order to prevent the capillary phenomenon between the primary mixing section 217 and the secondary mixing section 220, and between the secondary mixing section 220 and the photodetection path 230. This aluminum valve may be made in the same process as the Al coating in the photodetection path 230.

Second Embodiment

Figure 27:
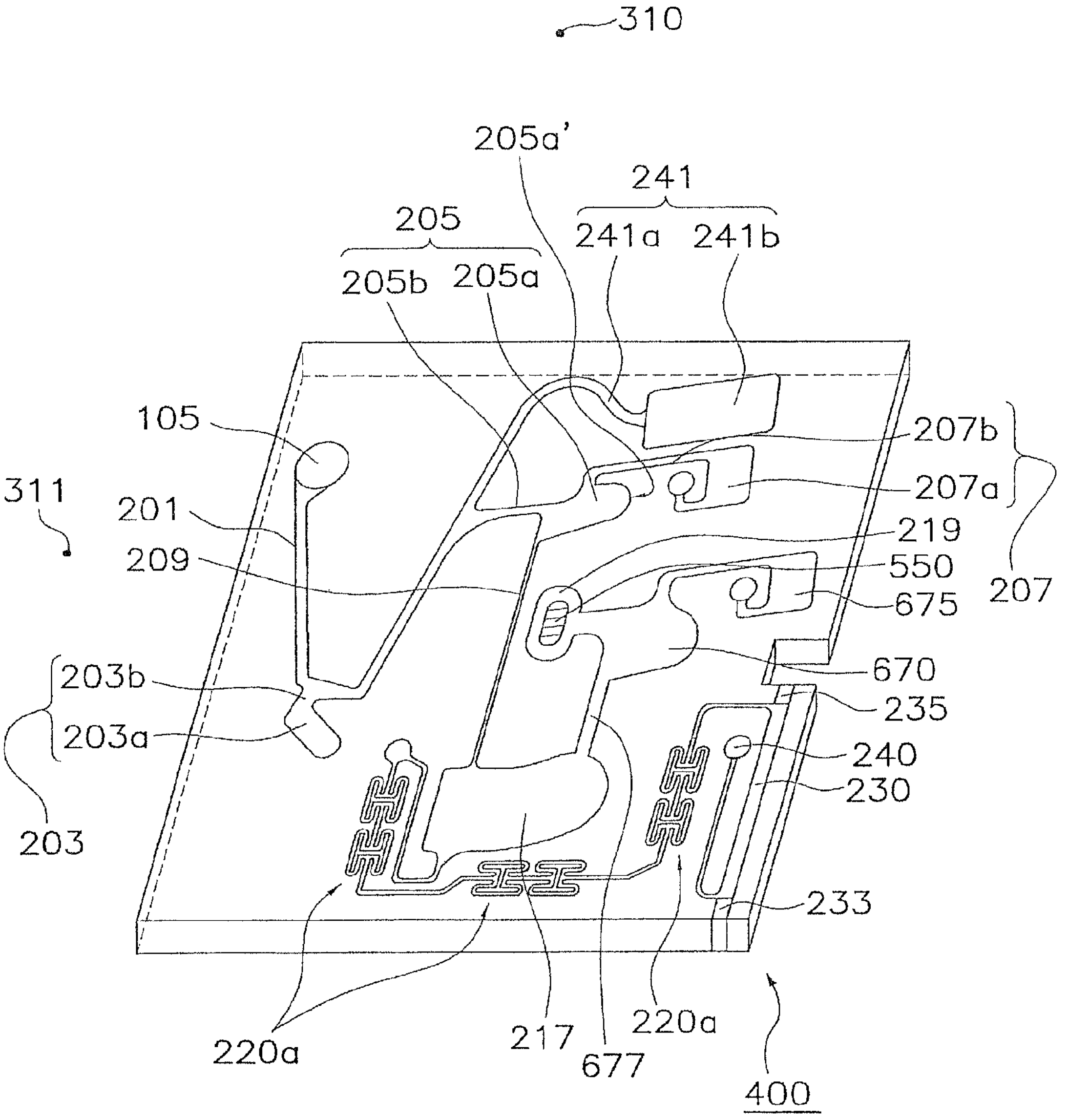
FIG. 27 is a perspective view of a test chip according to a second embodiment of the present invention.
Figure 28:
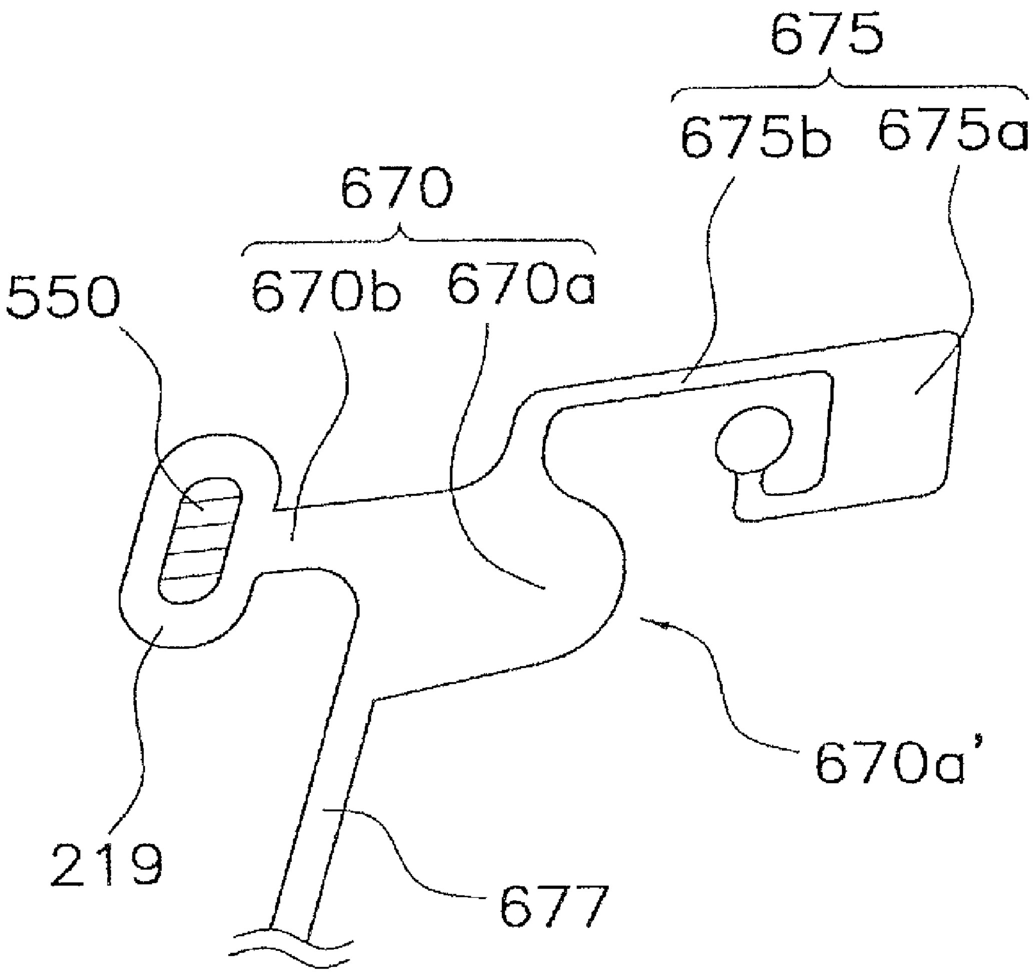
FIG. 28 is an explanatory diagram describing the principal portions of FIG. 27.
Figure 29:
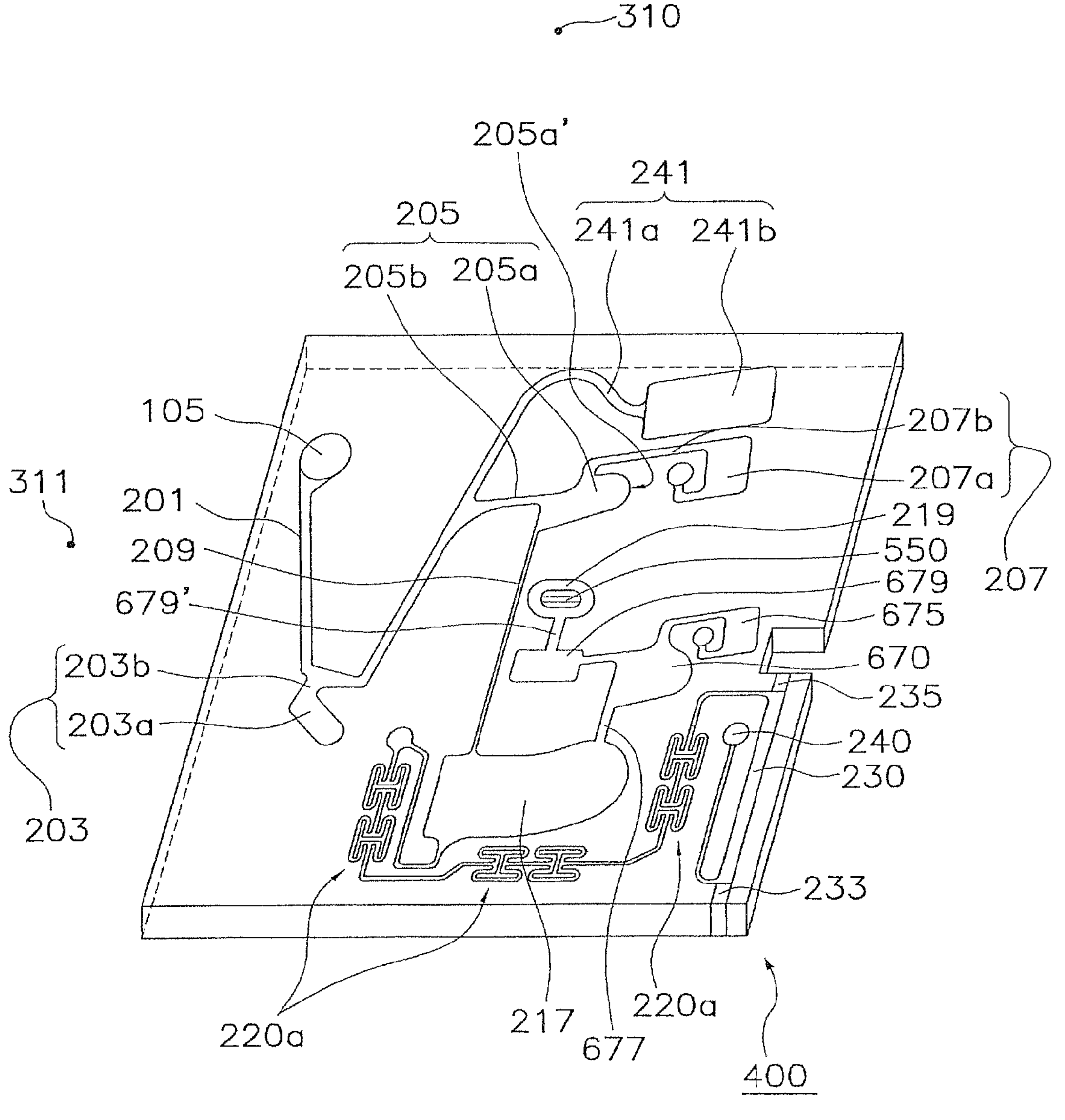
FIG. 29 is a perspective view of another test chip according to second embodiment.
Figure 30:
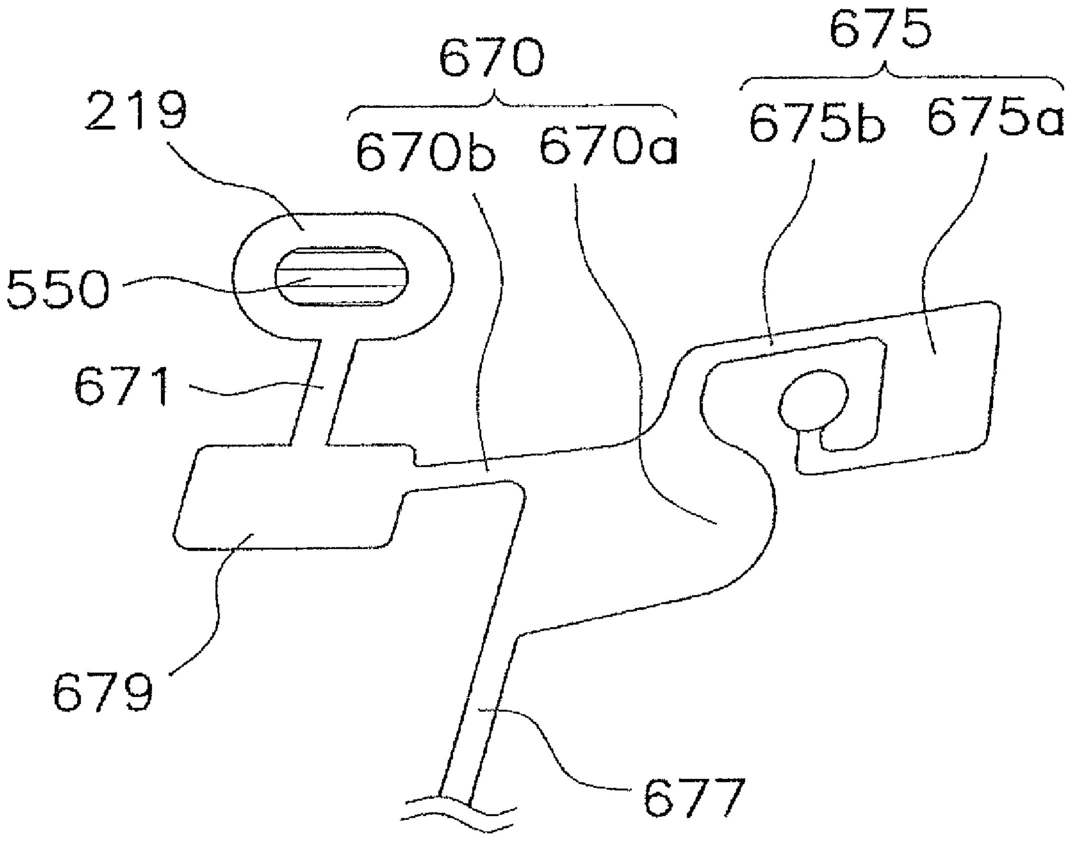
FIG. 30 is an explanatory diagram describing the principal portions of FIG. 29.

FIG. 27 is a perspective view of a test chip according to a second embodiment of the present invention, FIG. 28 is an explanatory diagram describing the principal portion of FIG. 27, FIG. 29 is a perspective view of another test chip according to the second embodiment, and FIG. 30 is an explanatory diagram describing the principal portion of FIG. 29. The second embodiment has the same configuration as that of the first embodiment except for being able to measure an introduced reagent using a reagent measuring section 670, a discarded reagent reservoir 675, a reagent removing tube 677, and a reagent introductory section 679. Identical reference notations and numerals represent identical structural elements.

A test chip 400 of FIG. 27 comprises an inlet 105 for a sample comprising a target component, a centrifugal separation tube 201, a first holding section (203*a*, 203*b*) 203, a first measuring section (205*a*, 205*b*) 205, a waste fluid reservoir (207*a*, 207*b*) 207, a removing tube 209, a primary mixing section 217, a reagent reservoir 219 for a reagent to be stored, a reagent measuring section 670, a discarded reagent reservoir 675, a reagent removing tube 677, a secondary mixing section 220 comprising mixer sections 220*a*, a photodetection path 230, a light inlet 233, a light outlet 235, an outlet 240, and a regulation tube (241*a*, 241*b*) 241.

The reagent measuring section 670 is connected to the reagent reservoir 219, the discarded reagent reservoir 675, and the reagent removing tube 677. The reagent measuring section 670 is constituted of a connecting portion **670*b* with the reagent measuring section 670 and the reagent reservoir 219, and of a reagent measuring section main unit 670*a* connected to the connecting portion 670*b*. In addition, in the reagent measuring section 670, the connecting portion 670*b* is disposed almost on the side of a second axis of rotation 311, and the reagent measuring section main unit 670*a* is disposed so that it is almost disposed on the side of the periphery in the radial direction of a circle around a second axis of rotation 311 with respect to the connecting portion 670*b*. Furthermore, a discarded reagent reservoir connecting section 675*b* of the discarded reagent reservoir 675 is branched so that the discarded reagent reservoir connecting section 675*b* branches from the reagent measuring section main unit 670*a* by the side of the second axis of rotation 311 with respect to the bottom 670*a*' of the reagent measuring section 670. In addition, a discarded reagent reservoir main unit 675*a* is connected so that the discarded reagent reservoir main unit 675*a* is located on the peripheral side in the radial direction of a circle around the second axis of rotation 311 with respect to the discarded reagent reservoir connecting section 675*b*. Furthermore, this discarded reagent reservoir main unit 675*a* is disposed so that it is located on the peripheral side in the radial direction of a circle around first axis of rotation 310 with respect to the discarded reagent reservoir connecting section 675*b***.

The test chip 400 is used by means of the following procedure. First, after a target component 510 was separated from a sample 500 by rotation around the first axis of rotation 310 in the centrifugal separation tube 201, for example, the reagent 550 is introduced into the reagent reservoir 219 by rupturing a capsule 600. Next, the test chip 100 is rotated around the second axis of rotation 311, the target component 510 is introduced into the first measuring section 205 from the centrifugal separation tube 201, and the reagent 550 in the reagent reservoir 219 is simultaneously introduced into the reagent measuring section 670. Since the discarded reagent reservoir 675 is connected to the reagent measuring section 670 at this point, the reagent 550 exceeding a predetermined volume of the reagent measuring section 670 is introduced into the discarded reagent reservoir 675. Therefore, a desired reagent 550 may be accurately measured by introducing the reagent 550 into the reagent measuring section 670. In addition, since the discarded reagent reservoir main unit **675*a* is located on the peripheral side in the radial direction of a circle around the first axis of rotation 310 with respect to the discarded reagent reservoir connecting section 675*b*, the reagent 550 introduced into the discarded reagent reservoir main unit 675*a* by rotation around the second axis of rotation 311 will not backflow to the reagent measuring section 670 by rotation around the first axis of rotation 310. Accordingly, in the reagent measuring section 670, the reagent 550 may be accurately measured. Finally, the accurately measured reagent 550 is introduced into the primary mixing section 217 from the reagent measuring section 670 via a reagent removing tube 677 by rotation around the first axis of rotation 310. At this point, the target component 510 is introduced into the primary mixing section 217 from the first measuring section 205. Thus, in the primary mixing section 217, the target component 510 and the reagent 550 are introduced to give a mixed substance 560** with a desired mixing ratio.

In addition to the test chip 400 in FIG. 27, a test chip 400 in FIG. 29 has a reagent introductory section 679 and a connecting tube 679' between the reagent reservoir 219 and the reagent measuring section 670.

First, a reagent 550 is introduced into the reagent reservoir 219 by, for example, rupturing a capsule 600. In the centrifugal separation tube 201, a target component 510 is separated from a sample 500 by rotation around the first axis of rotation 310, and simultaneously, a reagent 550 is introduced into the reagent introductory section 679 via the connecting tube 679' from the reagent reservoir 219. Next, the test chip 100 is rotated around the second axis of rotation 311, the target component 510 is introduced into the first measuring section 205 from the centrifugal separation tube 201, and simultaneously, the reagent 550 in the reagent reservoir 219 is introduced into the reagent measuring section 670. Furthermore, the target component 510 and the reagent 550 are introduced into the primary mixing section 217 by rotation around first axis of rotation 310 to give a mixed substance 560 having a desired mixing ratio. With the test chip 400 in FIG. 29, the reagent 550 may be introduced into the reagent reservoir 219 before the rotation of the test chip 400.

Third Embodiment

Figure 31:
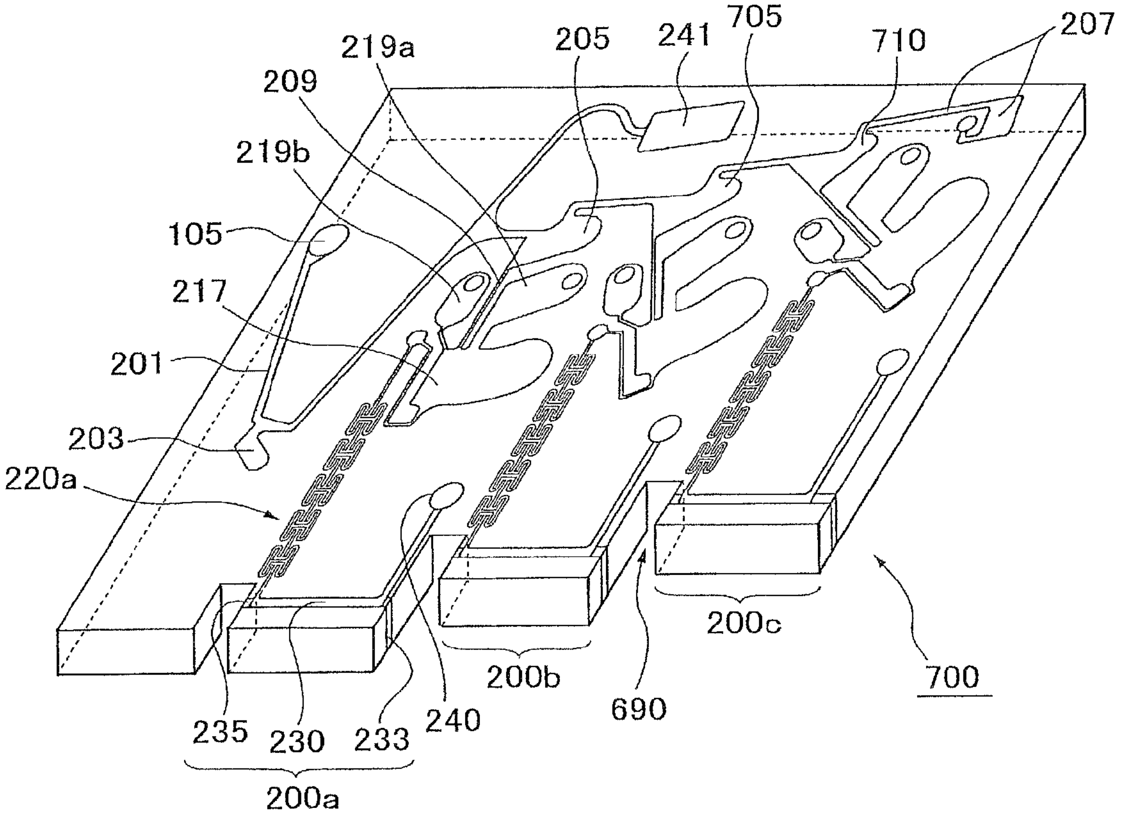
FIG. 31 is a perspective view of a test chip according to a third embodiment of the present invention.
Figure 32:
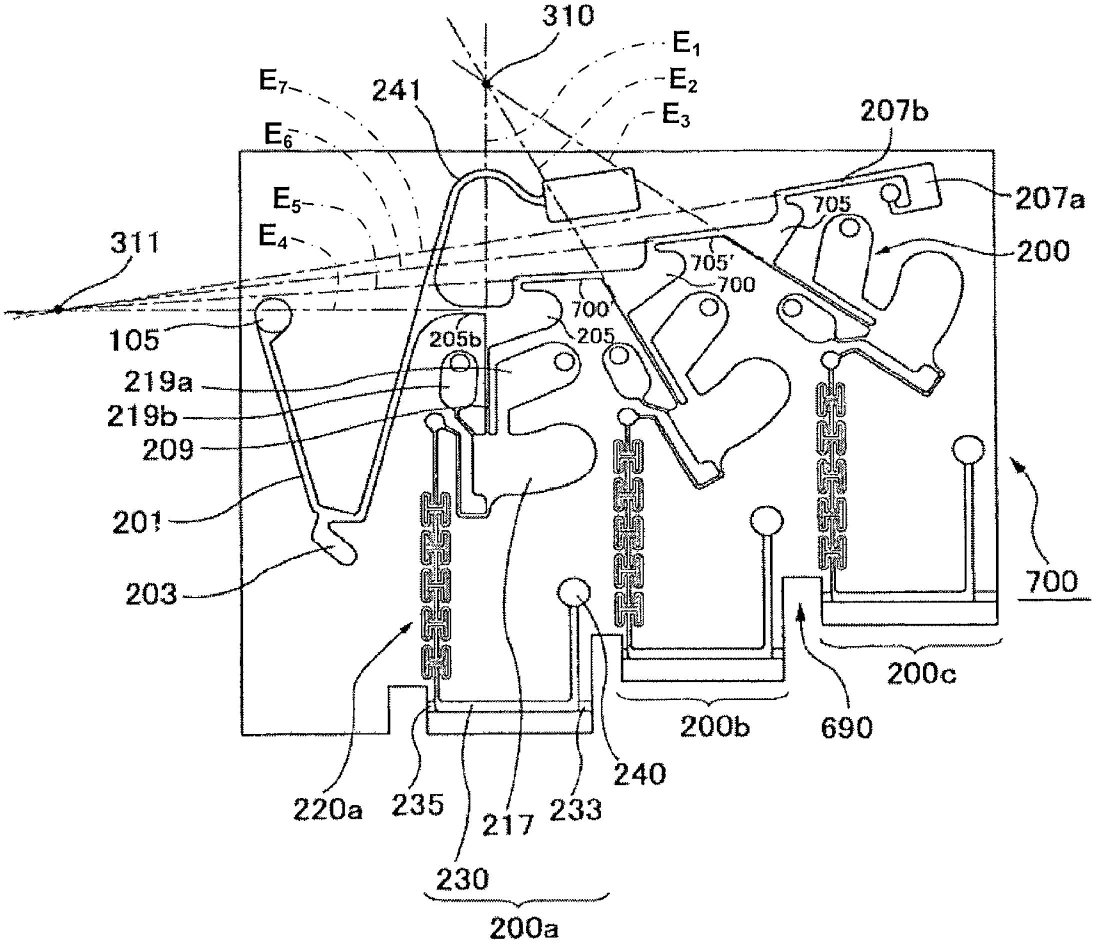
FIG. 32 is a plan view of FIG. 31.
Figure 33:
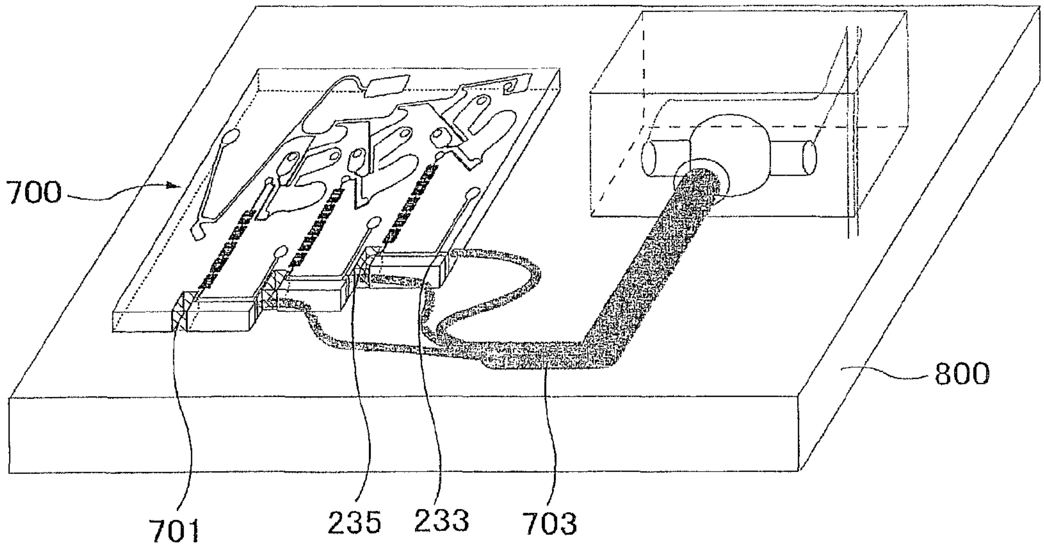
FIG. 33 shows a detecting device with a test chip of FIG. 31 laid thereon.

FIG. 31 is a perspective view of a test chip according to a third embodiment of the present invention, FIG. 32 is a plan view of FIG. 31, and FIG. 33 shows a detecting device having the test chip of FIG. 31 placed thereon. The third embodiment has the same configuration as that of the first embodiment except that a plurality of determining sections (**200*a*, 200*b*, 200*c*) 200 comprising a measuring section, a mixing section, etc. are provided so that a plurality of tests may be performed, and that the configuration in the vicinity of the substrate of the light inlet 233 and the light outlet 235** differs from that of the first embodiment. Identical notations and numerals represent identical structural elements.

A test chip 100 of the third embodiment comprises an inlet 105 of a sample comprising a target component, a centrifugal separation tube 201, a first holding section 203, a plurality of determining sections (**200*a*, 200*b*, 200*c*) 200, a waste fluid reservoir 207, and a regulation tube 241. Each of the determining sections 200 comprises a removing tube 209, a primary mixing section 217, a reagent reservoir (219*a*, 219*b*) 219 having a reagent to be stored, a secondary mixing section 220 comprising mixer sections 220*a*, a photodetection path 230, a light inlet 233, a light outlet 235, and an outlet 240. Furthermore, each of the determining sections 200*a*, 200*b*, and 200*c* has a first measuring section 205, a second measuring section 700, and a third measuring section 705. The first measuring section 205 is connected to the second measuring section 700 via the measuring section connecting tube 700', and the second measuring section 700 is connected with the third measuring section 705 via a measuring section connecting tube 705'. In addition, the third measuring section 705 is connected to a waste fluid reservoir 207. Here, volumes of each of the measuring sections are formed so that they may become smaller in this order as they move away from the centrifugal separation tube 201**, as shown in the following formula (1).

The first measuring section 205>the second measuring section 700>the third measuring section 705 (1)

Furthermore, as shown in FIG. 32, extension lines from each removing tube 209 for each of the determining sections 200 intersect on the first axis of rotation 310. In addition, extension lines of a measuring section connecting tube **205*b*, which is a connecting portion of the first measuring section 205, and the centrifugal separation tube 201, the measuring section connecting tube 700', the measuring section connecting tube 705'**, and a waste fluid reservoir connecting section 207*b*, which is a connecting portion of the waste fluid reservoir 207 and the third measuring section 705, intersect one another on the second axis of rotation 311, as shown in FIG. 32. Such a design enables efficient introduction of the target component 510 measured by the primary mixing section 217 from each removing tube 209 in each determining section 200 by rotation around the first axis of rotation 310. This is because that the direction of the centrifugal force of the rotation around the first axis of rotation 310 and extending directions of the removing tubes 209 are almost coincident with each other. In addition, the target component 510 may be efficiently introduced into the first measuring sections 205 in each determining section 200, the second measuring section 700, and the third measuring section 705 by rotation around the second axis of rotation 311. This is because that the direction of the centrifugal force of the rotation around the second axis of rotation 311 is almost coincident with the extending directions of the measuring section connecting tube 205*b*, the measuring section connecting tube 700', the measuring section connecting tube 705', and the waste fluid reservoir connecting section 207*b*.

In this third embodiment, after separation of the target component 510 in the centrifugal separation tube 201, the target component 510 is introduced from the centrifugal separation tube 201 by rotation around the second axis of rotation 311 to the first measuring section 205. Here, target component 510 that has overflowed from the first measuring section 205 is introduced to the second measuring section 700. In addition, target component 510 that has overflowed from the second measuring section 700 is introduced to the third measuring section 705. Furthermore, target component 510 that has overflowed from the third measuring section 705 is introduced to the waste fluid reservoir 207. Such introduction of the target component 510 to each measuring section may deliver the desired amounts of the target component 510 into each of the first measuring section 205, the second measuring section 700, and the third measuring section 705. At this point, in each measuring section, volumes are designed to become larger as each measuring section is closer to the centrifugal separation tube 201. Accordingly, overflow from the first measuring section 205 of the target component 510 introduced into the first measuring section 205 to the centrifugal separation tube 201 side may be reduced.

In addition, since the target component 510 may be measured in the desired amounts and determined in each of the determining sections 200, a plurality of items may be tested at once.

Figure 34:
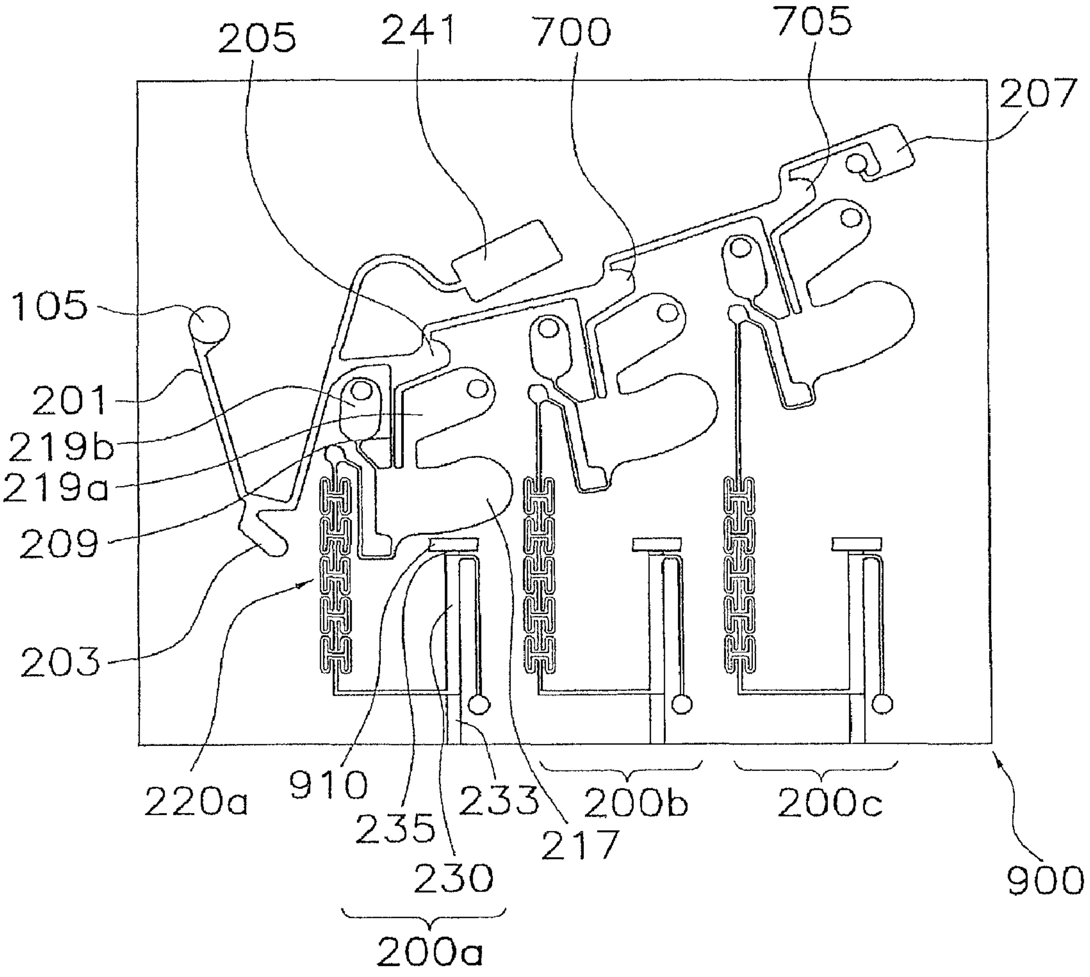
FIG. 34 is a plan view of another test chip according to the third embodiment of the present invention.

Furthermore, in the substrate of the test chip 700 are provided a light inlet 233 for introducing a light into a photodetection path 230, and an opening 690 wherein a light outlet 235 for allowing light to exit therefrom is exposed. Here, the light inlet 233 and the light outlet 235 are optical waveguides that allow light to pass therethrough. This test chip 700 is placed on a detecting device 800, as shown in FIG. 33. An optical fiber 703 is connected to the light inlet 233 of each of the determining sections 200, and then a photodetection section 701, such as a photodiode on the detecting device 800, is inserted into the opening 690 of the test chip 700 to perform determination of the target component 510. In addition, light detection may be performed by inserting a photodetection section, such as a photodiode, in a hole section 910 provided in the substrate adjacent to the light outlet 235, as shown in FIG. 34.

Figure 35:
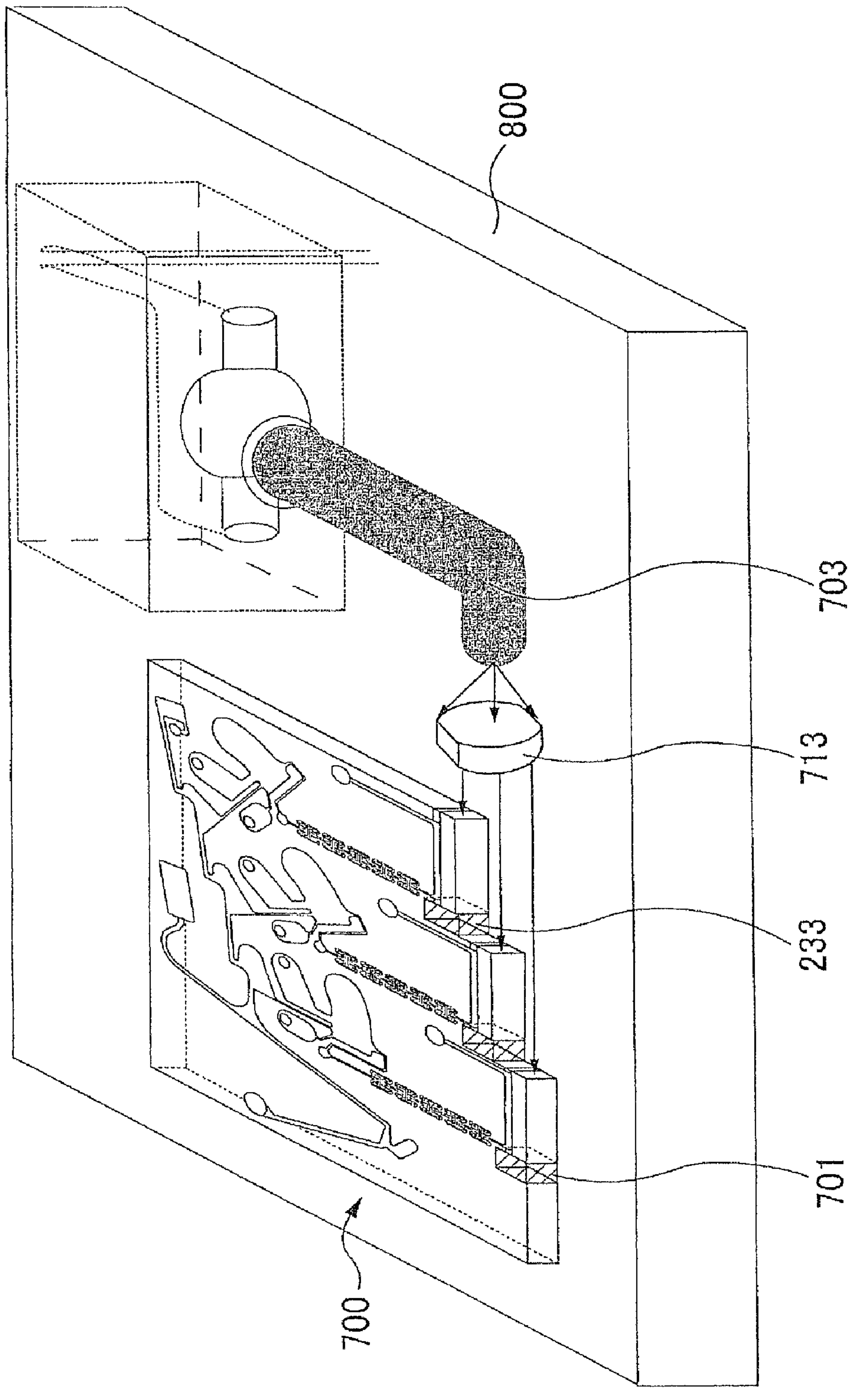
FIG. 35 shows an example of a method of irradiating light in a photodetection path.

Furthermore, as shown in FIG. 35, light from an optical fiber 703 may be converted into a parallel beam by a lens 713, and then the light having larger luminous flux may be introduced into each of the light inlets 233.

Other Embodiments

Figure 36:
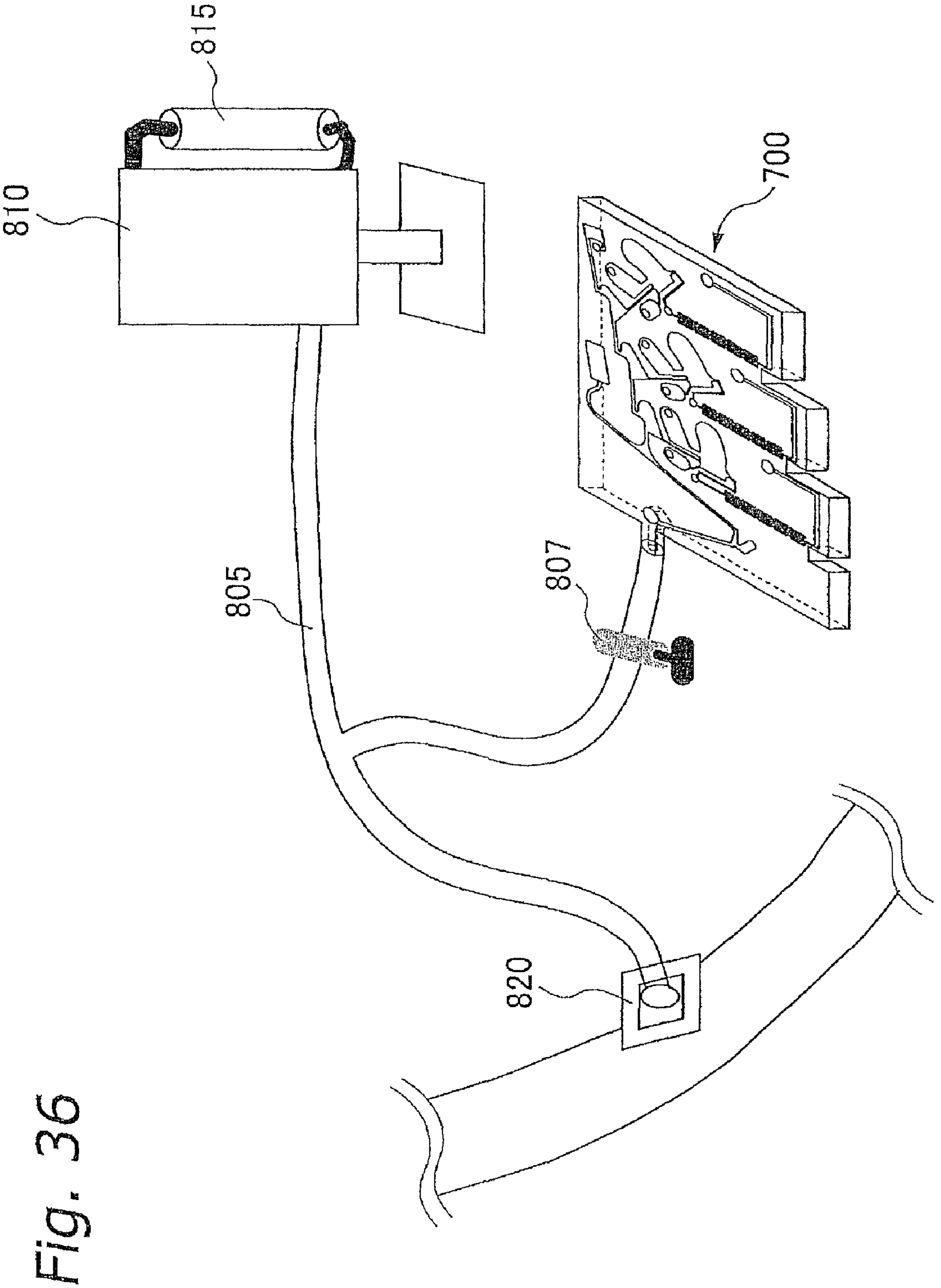
FIG. 36 shows a test chip of another embodiment.

The test chip of the embodiment may be utilized in combination with a dialysis apparatus. FIG. 36 is a schematic diagram of the test chip of the embodiment connected to a dialysis apparatus. An inlet of the test chip performs blood collection from skin via a blood liquid sending tube 805 and a shunt, or a needle 820. In addition, the blood liquid sending tube 805 is connected with the dialysis apparatus 810 having hollow fibers 815. Furthermore, in order to adjust liquid sending to the test chip, a valve Z is provided near the inlet. Dialysis apparatus 810 is used in order to assist the decline in the elimination function of waste matter, such as urea nitrogen and creatine in blood, due to renal function degeneracy. Although such real time measurement of the concentration of waste matter in blood is difficult, use of the test chip of the embodiment in combination with the dialysis apparatus enables real time measurement. An accurate concentration of the waste matter in the blood may be adjusted by feedback of the test results.

Figure 37:
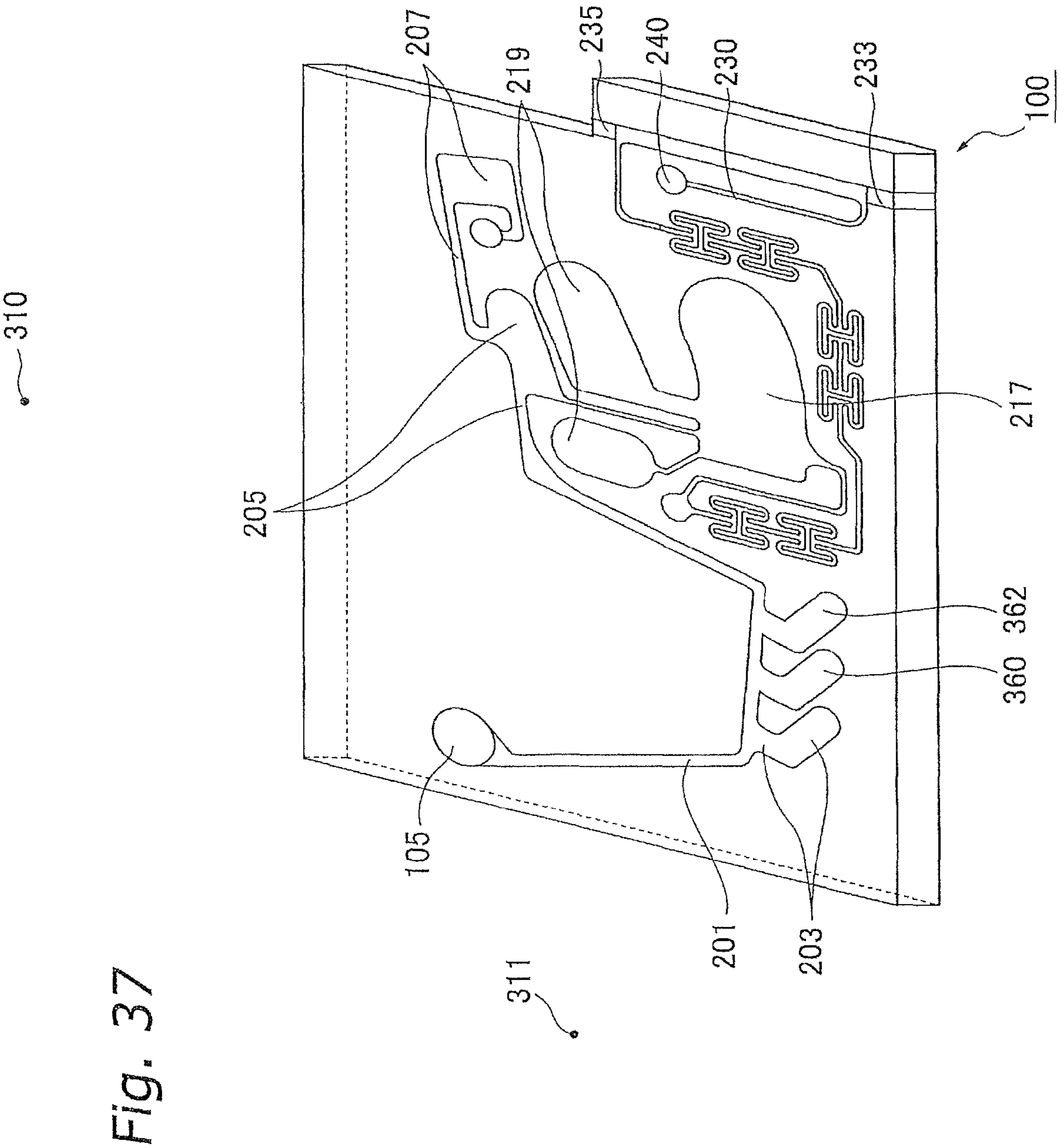
FIG. 37 is a perspective view of a test chip 100 having a plurality of holding sections provided therein.

The first holding sections 19 and 203 are provided in the centrifugal separation tube 9 and 201 of the embodiment, a plurality of holding sections, such as the second holding section 360 and the third holding section 362 may be provided. FIG. 37 is a perspective view of a test chip 100 having a plurality of holding sections. The second holding section 360 and the third holding section 362 are provided in the bottom of a centrifugal separation tube 201 in the same manner as the first holding section. Furthermore, non-target components 520 are introduced into the second holding section 360 and the third holding section 362, by rotation around the first axis of rotation 310, and non-target components 520 are held during rotation around the second axis of rotation 311. Thus, by further providing a plurality of holding sections, non-target components 520 that cannot be held only by the first holding section may be held in the second holding section. For example, even when a larger amount of sample 500 are to be introduced into the centrifugal separation tube 209, and a larger amount of a non-target components 520 are to be separated, the target component 510 may be separated in the centrifugal separation tube 209 by introducing the larger amount of the non-target components 520 into the first holding section and the second holding section.

Although a regulation tube is not provided in FIG. 37, the regulation tube may be provided therein.

Figure 38:
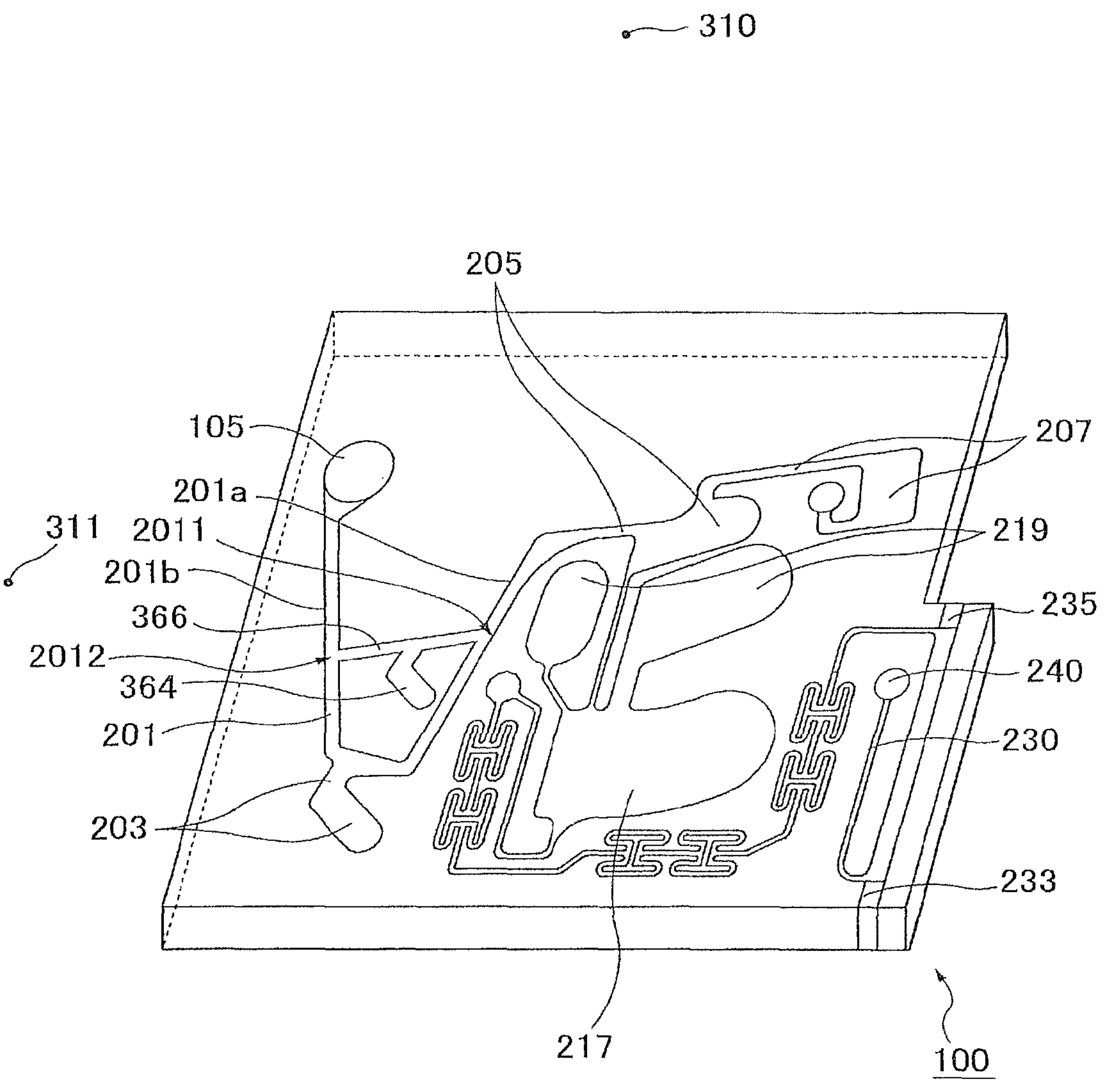
FIG. 38 is a perspective view of a test chip 100 having a bypass tube 366 and a third holding section 364 provided therein.

(c) Although the first holding sections 19 and 203 are provided in the centrifugal separation tubes 9 and 201 of the embodiment, a bypass tube 366 for connecting both sides of the centrifugal separation tube may further be provided, and a third holding section 364 may be provided in the bypass tube 366. FIG. 38 is a perspective view of a test chip 100 having the bypass tube 366 and the third holding section 364.

The centrifugal separation tube 201 has a first tube 201*a* extending from the bottom of the centrifugal separation tube 201 to one first end portion 2011 of the centrifugal separation tube 201 connected to the first measuring section 205, and a second tube 201*b* extending to another second end portion 2012 of from the bottom. The bypass tube 366 connects the first tube 201*a* and the second tube 201*b* of this centrifugal separation tube 201. A third holding section 364 is provided in a bypass tube 366, non-target components 520 are introduced by rotation around the first axis of rotation 310 therein, and the section maintains the non-target components 520 during rotation around the second axis of rotation 311.

When a large amount of sample 500 that fills the centrifugal separation tube 201 and the bypass tube 366 are to be introduced into the test chip 100 of the above configurations, on the one hand, during rotation around the first axis of rotation 310, the non-target components 520 are held in the first holding section 203 in the bottom of the centrifugal separation tube 201, and simultaneously they are held in the third holding section 364 connected to the bypass tube 366. Accordingly, the target component 510 in the sample 500 is separated into the centrifugal separation tube 201 and the bypass tube 366. On the other hand, when a smaller amount of sample 500 than an amount which fills the bypass tube 366 is introduced only into the centrifugal separation tube 201, during the rotation around the first axis of rotation 310, the non-target components 520 are separated only into the first holding section 203 in the bottom of the centrifugal separation tube 201, and are held therein. Note that when the first holding section 203 is only set to have a larger volume in order to hold a large amount of the non-target components delivered from a large amount of the sample, not only the non-target components 520, but also the target component 510, will be separated into the first holding section 203 in the separation of a small amount of the samples, reducing the amount of the target components 510 after separation. As described above, according to the amount of the sample 500, the target component 510 and the non-target components 520 may be efficiently separated by providing the third holding section 364 in the bypass tube 366.

Furthermore, the distance between the first end portion 2011, which is a connecting portion from the bypass tube 366 to the first tube 201*a*, and the first axis of rotation 310, is smaller than the distance between the second end portion 2012, which is a connecting portion from the bypass tube 366 to the second tube 201*b*, and the first axis of rotation 310. When the sample is incorporated from the inlet connected to the second tube 201*b* of the centrifugal separation tube 201 by rotation of the first axis of rotation 310, the bypass tube 366 will be filled after the interior of the centrifugal separation tube 201 is filled. Accordingly, the bypass tube 366 will not work for a smaller amount of the sample 500, but the bypass tube 366 will work only for a larger amount of sample. In addition, the angle made by the bypass tube 366 and the connecting portion of the second tube 201*b* is preferably less than 90 degrees. Thus, since the bypass tube 366 inclines with respect to the bottom of the centrifugal separation tube 201, during the incorporation of the sample 500 from the inlet, the bypass tube 366 will be filled after the interior of the centrifugal separation tube 201 is filled.

Figure 39:
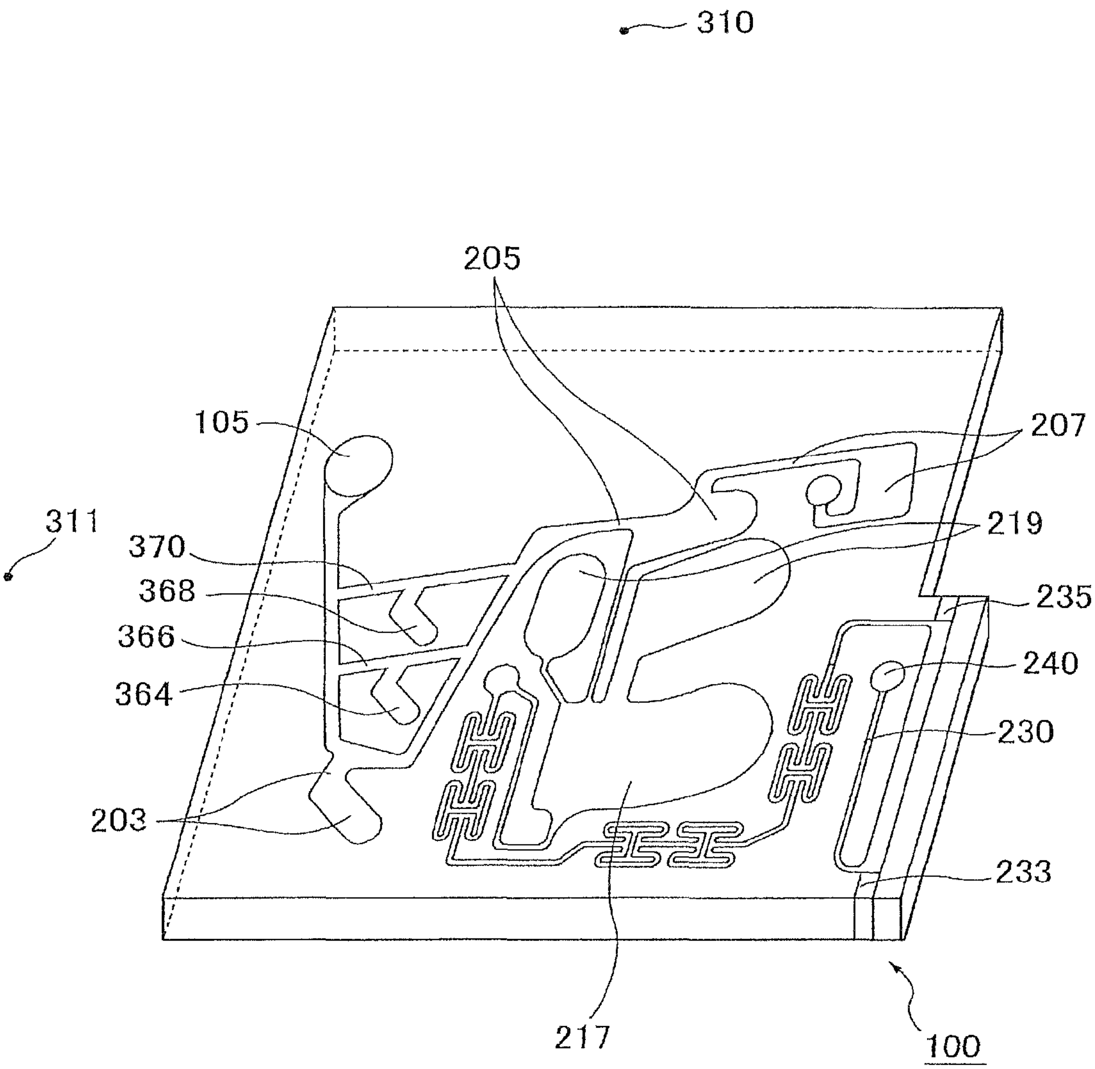
FIG. 39 is a perspective view of a test chip 100 having a plurality of bypass tubes and a third holding section provided therein.

Furthermore, as shown in FIG. 39, two or more bypass tubes and the third holding sections may be provided. In FIG. 39, the bypass tube 366 and the third holding section 364, and a bypass tube 370 and a fourth holding section 368, are provided.

Figure 40:
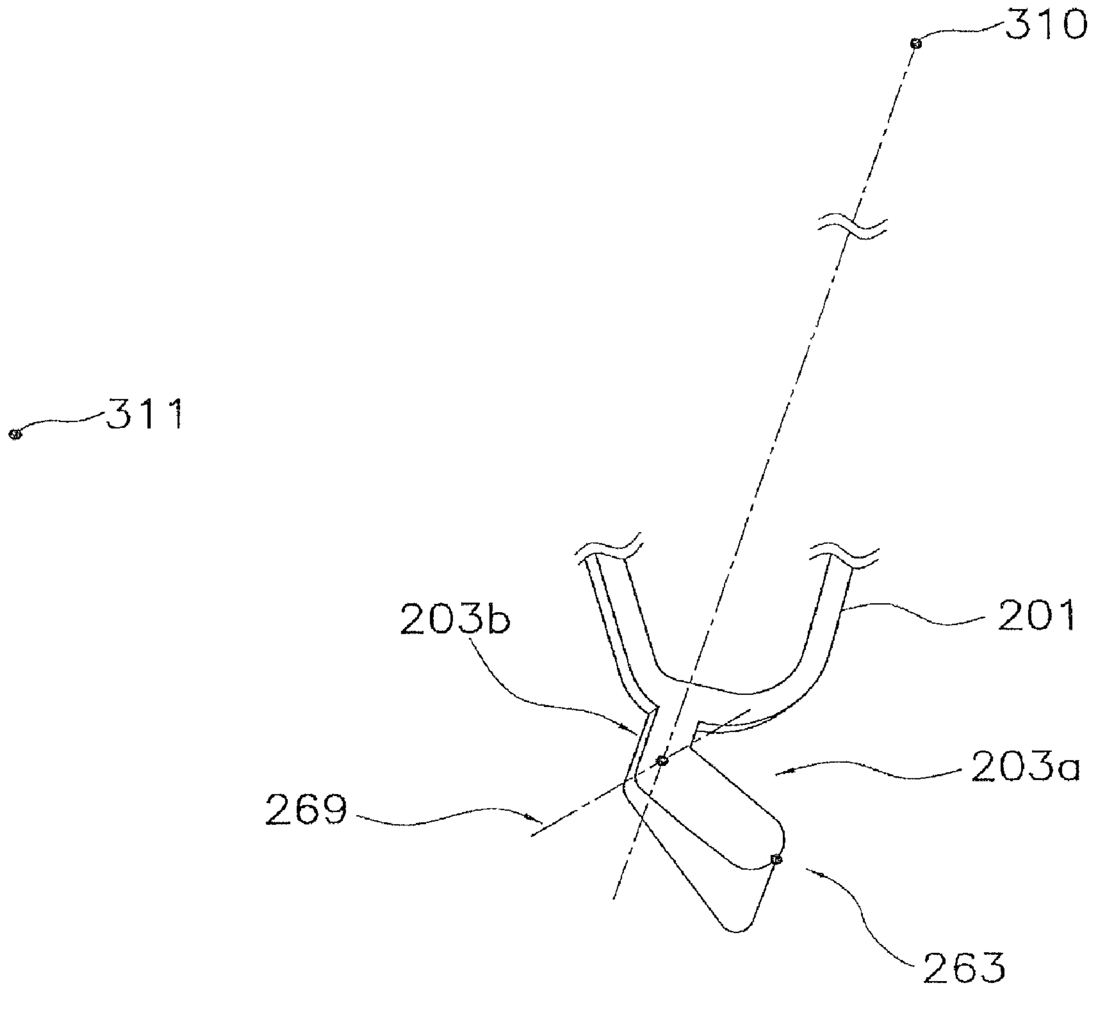
FIG. 40 is an enlarged perspective view of a first holding section that is inclined in the depth direction.

(d) Inclination in the depth direction is preferably given to the holding section main unit of the first holding sections 19 and 203 in the above described embodiment. FIG. 40 is an enlarged perspective view of the first holding section having an inclination in the depth direction. The first holding section has a holding section main unit 203 and a holding section connecting tube 203*b*. As the distance between a point within the holding section main unit 203*a* and the second axis of rotation becomes larger, the holding section main unit 203*a* becomes deeper. Here, the depth of the holding section main unit 203*a* represents the direction intersects almost perpendicular to the principal plane of the test chip.

Thus, since the depth of the holding section connecting tube 203*b* as an inlet port of the holding section main unit 203*a* is small, and the depth of the holding section main unit 230*a* becomes larger as the distance from the holding section connecting tube 203*b* becomes larger, backflow of the non-target components 520 from the holding section main unit 203*a* through the holding section connecting tube 203*b* may be prevented during rotation around the second axis of rotation 311. In addition, by providing a larger dimension in the depth direction, a larger volume of the holding section main unit 203*a* can be realized, without enlarging the size of the test chip. Accordingly, miniaturization of the test chip may be achieved while improving the separation efficiency of the target component 510.

In the same manner as the second holding section and third holding section, described in other embodiments, miniaturization of the test chip may be advantageously achieved while improving separation efficiency by providing inclination in the depth direction.

Figure 41:
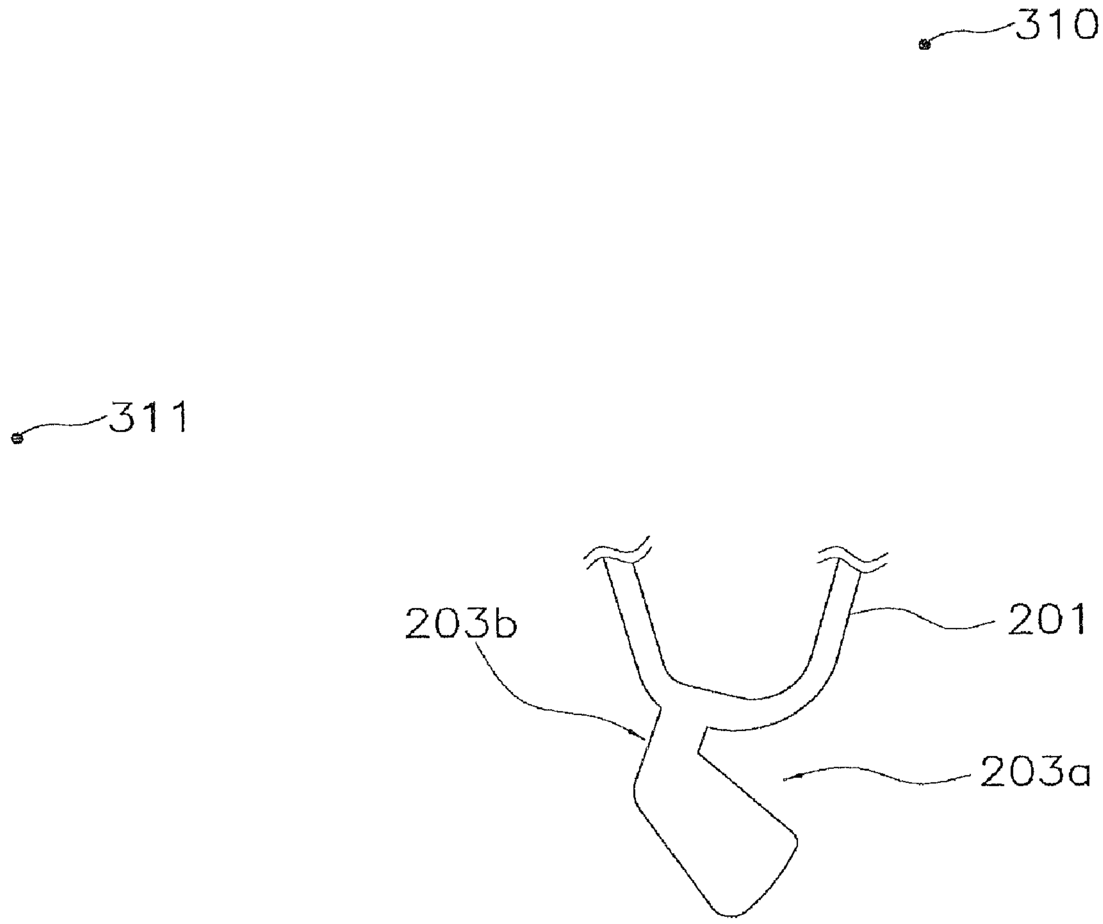
FIG. 41 is an enlarged perspective view of a first holding section having a varying cross-sectional area.

Similarly, in the holding section main unit of the first holding sections 19 and 203 in the previously described embodiments, the holding section main units preferably have a larger cross-sectional area as the holding section main units separate from the second axis of rotation 311 as shown in FIG. 41. For example, a cross-sectional area in the direction of the principal plane of test chip 100 preferably becomes larger as it separates from the second axis of rotation. Since the cross-sectional area in the holding section connecting tube 203*b* as an inlet port of the holding section main unit is small, and a cross-sectional area of holding section main unit becomes larger as the distance from the holding section connecting tube 203*b* becomes distant, backflow of the non-target components from the holding section main unit via the holding section connecting tube 203*b* may be prevented during rotation around the second axis of rotation 311.

Experiment 1

Figure 42:
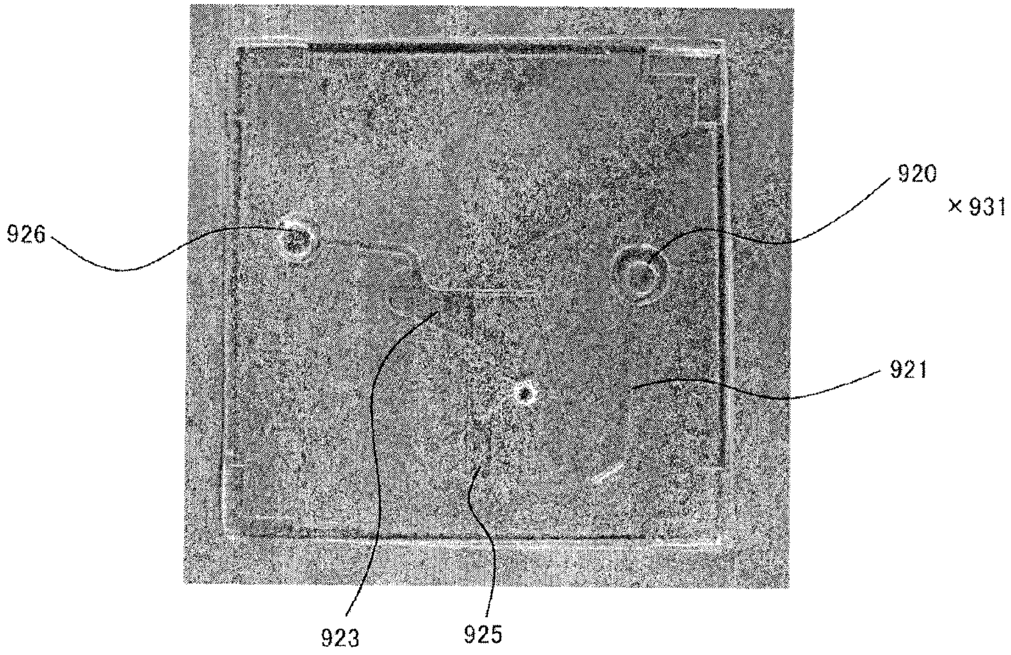
FIG. 42 shows a test chip of Experiment 1.

In Experiment 1, an experiment was performed in order to determine whether measurement of a target component was accurately performed in a first and a second axis of rotation. A test chip shown in FIG. 42 has an inlet 920 for incorporating a sample, a centrifugal separation tube 921, a first measuring section 923, an outlet 925, and a waste fluid reservoir 926. This test chip has the same configuration as that of the test chip 1 shown in the embodiment, and also has the same relationship between each section of test chip 1, and a first axis of rotation 930 and a second axis of rotation 931 as the test chip 1 in the embodiment.

The test chip has a minimum channel width in each section of 200 micrometers, a first measuring section 923 volume of 0.25 microliters, a channel width in a fluid reservoir of 1 mm, and all channel depths are 200 micrometers. Pure water colored with an ink was introduced into this test chip. Rotation around the first axis of rotation 930 and the second axis of rotation 931 were carried out with a turning radius of 1.3 cm, and an rotating speed of 3000 rpm.

Step 1:

The test chip was first rotated for 10 seconds by rotation around the first axis of rotation 930.

Step 2:

Next, by rotation for 10 seconds of the test chip around the second axis of rotation 931, the pure water was introduced into the first measuring section 923 from the centrifugal separation tube 921. At this point, the pure water that exceeded a predetermined volume of the first measuring section 923 was introduced into the waste fluid reservoir 926.

Step 3:

Furthermore, by rotation for 10 seconds of the test chip around the first axis of rotation 930, the pure water measured in the first measuring section 923 was introduced into the outlet 925.

Figure 43:
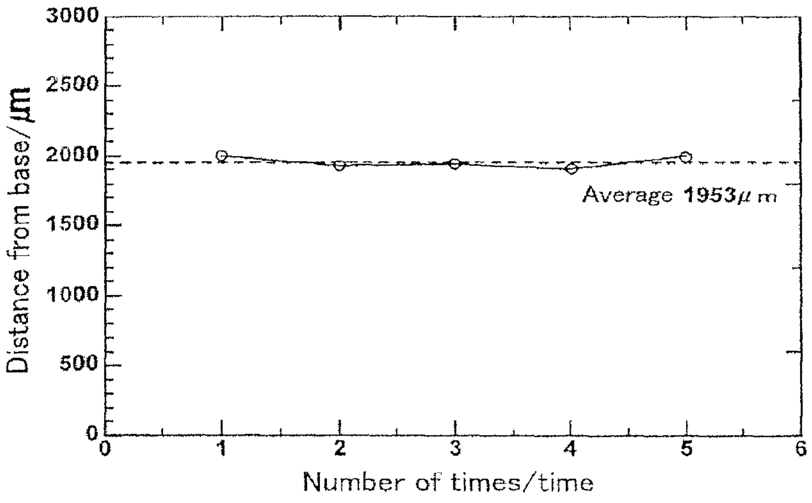
FIG. 43 shows the results of Experiment 1.
Figure 44A:
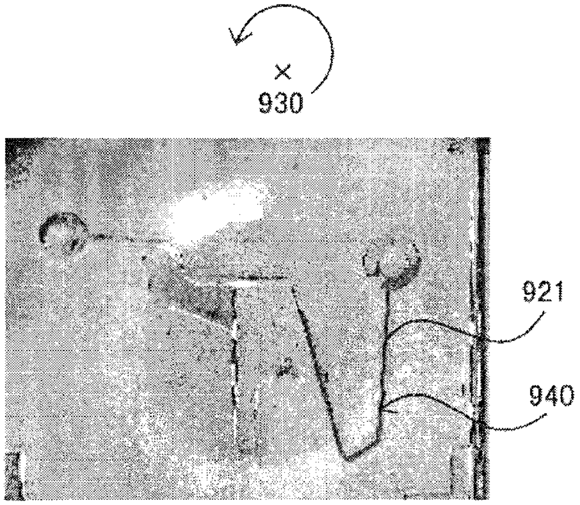
FIG. 44A shows the results (1) of Comparative Example 1.
Figure 44B:
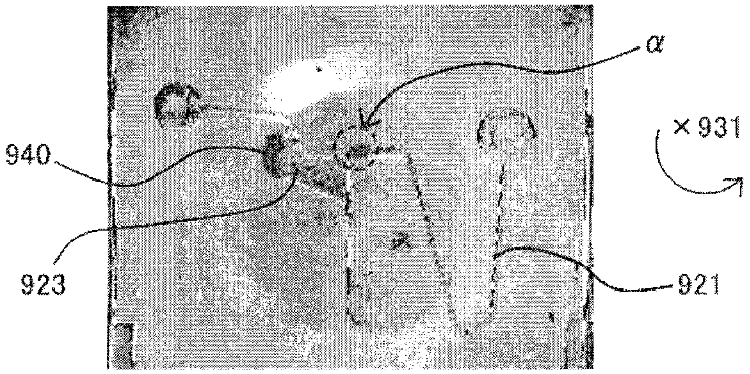
FIG. 44B shows the results (2) of Comparative Example 1.
Figure 44C:
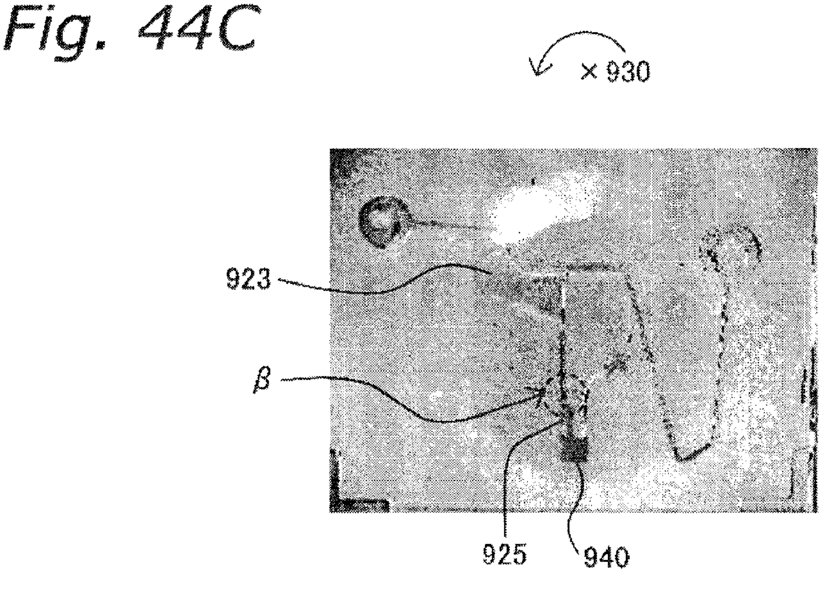
FIG. 44C shows the results (3) of Comparative Example 1.

This operation was performed 5 times. FIG. 43 shows the results. The results of FIG. 44A to FIG. 44C show that measurement of almost equivalent amounts of solution has been performed. Accordingly, the results show that the rotation of the test chip as shown in Experiment 1 can accurately measure the solution.

Comparative Example 1

An MPC polymer (2-methacryroyloxyethyl-phosphorylcholine polymer) dissolved in an ethanol solution with a concentration of 3 wt % was coated twice onto all of channels of an inlet 920, a centrifugal separation tube 921, a first measuring section 923, an outlet 925, and a waste fluid reservoir 926 etc. of a test chip by Experiment 1. Conditions of a standard serum 940 were observed using this test chip. The same method as that in Experiment 1 was adopted. FIG. 44A to FIG. 44C show the results. FIG. 44A shows a step 1, and the result obtained when rotating the test chip of Comparative Example 1 around a first axis of rotation 930. FIG. 44B shows a step 2, in which the standard serum 940 is introduced into the first measuring section 923 from the centrifugal separation tube 921 by rotation around the second axis of rotation 931. Since the volume of the first measuring section 923 is larger than the volume of a connecting portion connecting the first measuring section 923 to the centrifugal separation tube 921 at this point, the capillary phenomenon makes the standard serum 940 backflow in the direction of the centrifugal separation tube 921 in point cc. In addition, FIG. 44C shows a step 3, in which the standard serum 940 is introduced into the outlet 925 from the first measuring section 923 by rotation around the first axis of rotation. Since the volume of the outlet 925 is larger than the volume of the connecting portion for connecting the outlet 925 to the first measuring section 923 at this point, at a point 13, the standard serum 940 backflows in the direction of the first measuring section 923 due to the capillary phenomenon, disabling accurate measurement. It was shown that although the MPC has an effect of preventing deposition of proteins etc. in a blood sample onto a channel surface, on the other hand, it will cause backflow due to the reduction in the angle of contact as described above.

Experiment 2

Figure 45A:
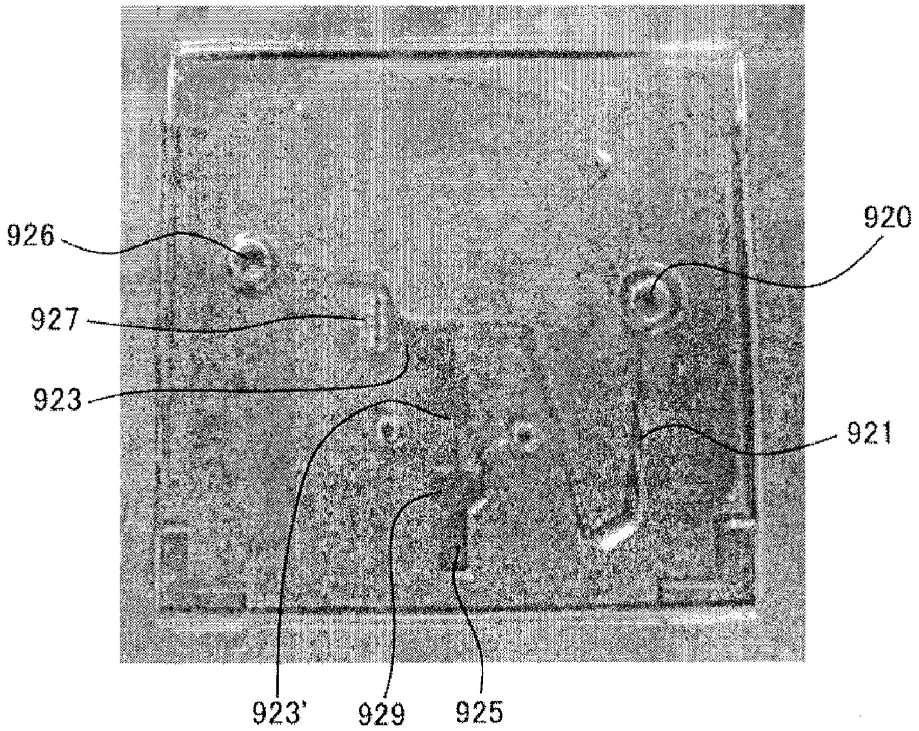
FIG. 45A shows a test chip of Experiment 2.
Figure 45B:
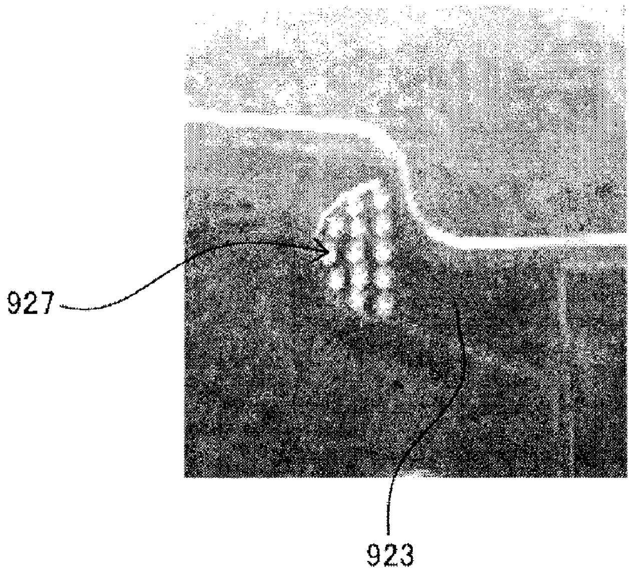
FIG. 45B is an enlarged view of a first measuring section.
Figure 46A:
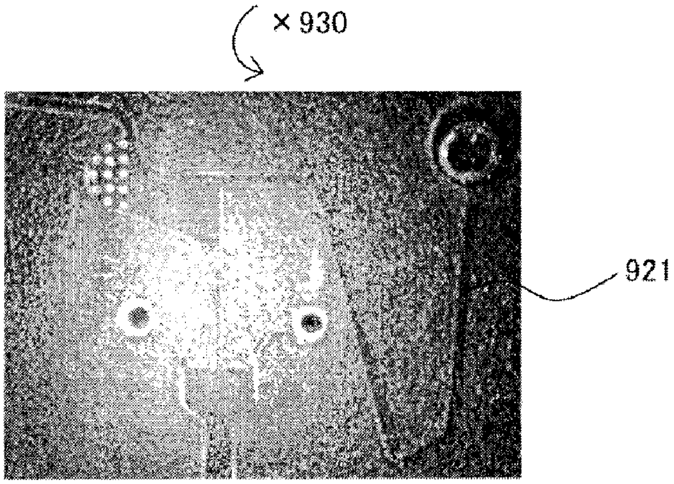
FIG. 46A shows the results (1) of Experiment 2.
Figure 46B:
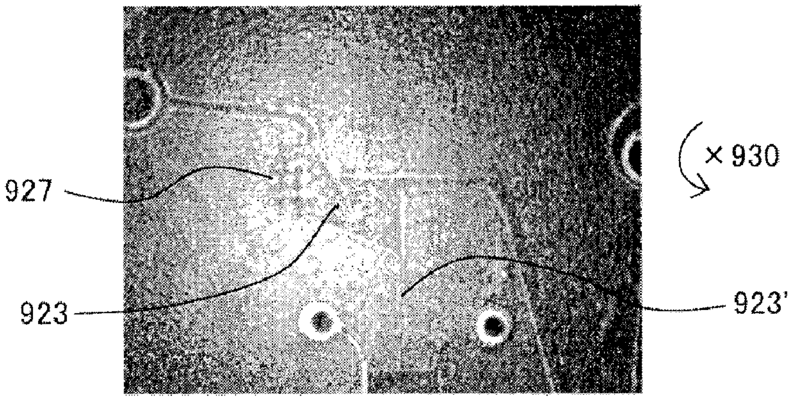
FIG. 46B shows the results (2) of Experiment 2.
Figure 46C:
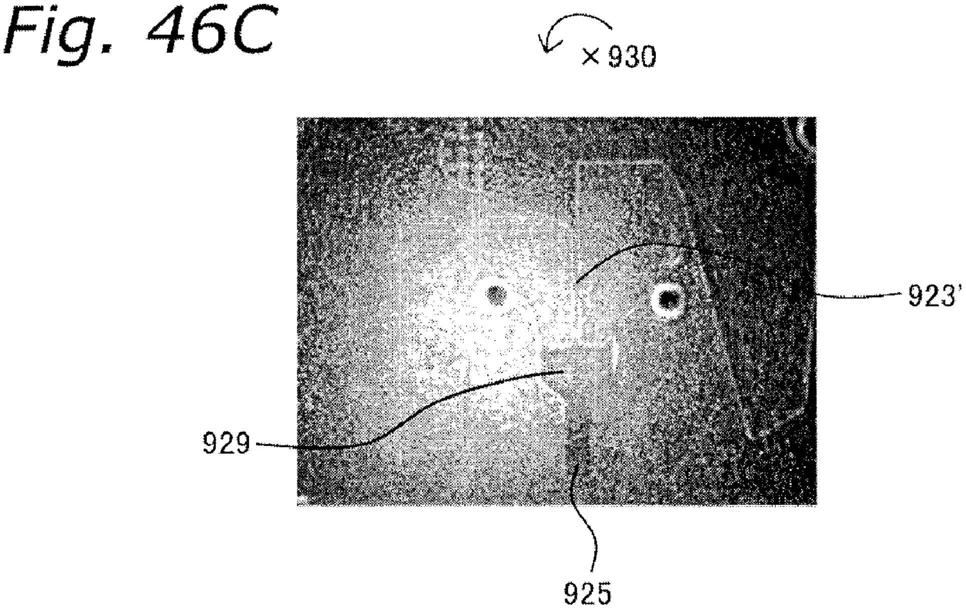
FIG. 46C shows the results (3) of Experiment 2.

FIG. 45A shows a test chip of Experiment 2, and FIG. 45B is an enlarged view of a first measuring section. Poles 927 were provided in the first measuring section 927 of the test chip of Experiment 2. In addition, an aluminum valve 929 was provided between a connecting portion 923' connected to the first measuring section 923, and an outlet 925. Other configurations are same as that of Comparative Example 1. MPC is applied to the entire channel. The experimental method is the same as that of Comparative Example 1. Each of the poles 927 has a cylindrical form and has a diameter of 200 micrometers, and a distance between poles of 200 micrometers. In addition, the channel width of the outlet 929 is 0.8 mm. FIG. 46A to FIG. 46C show the results of Experiment 2.

FIG. 46A shows a step 1, and shows the result obtained when rotating the test chip of Comparative Example 1 around the first axis of rotation 930. FIG. 46B shows a step 2, in which a standard serum 940 is introduced into the first measuring section 923 from the centrifugal separation tube 201 by rotation around the second axis of rotation 931. At this point, backflow of the standard serum 940 from the first measuring section 923 in the direction of the centrifugal separation tube 921 is prevented. In addition, FIG. 46C shows a step 3, in which the standard serum 940 is introduced into the outlet 925 via the connecting portion 923' from the first measuring section 923 by rotation around the first axis of rotation 930. At this point, backflow of the standard serum 940 from the outlet 925 in the direction of the first measuring section 923 is prevented.

Accordingly, it was made clear that prevention of backflow of an introduced solution could be performed, by providing poles or an aluminum valve in a section in which the capillary phenomenon was caused.

INDUSTRIAL APPLICABILITY

Since separation and measurement of a target component are performed by only the rotation of a test chip, connection of the test chip with an apparatus, such as a pump, will not be needed for separation and measurement, allowing simplification of the overall structure of the apparatus having the test chip placed thereon. Furthermore, since separation and measurement may be performed in one chip, miniaturization of the test chip may be achieved. Accordingly, the present invention may be utilized for portable test chips and the like.

What is claimed is:

1. A measuring chip for separating and measuring a target component in a sample by rotation around a first axis and a second axis of rotation, comprising:

a centrifugal separation tube for centrifugally separating the target component from the sample by rotating the measuring chip around the first axis of rotation;

a first holding section provided in the bottom of the centrifugal separation tube, wherein non-target components in the sample are introduced therein by rotation around the first axis of rotation, and the first holding section holding the non-target components during rotation around the second axis of rotation; and a plurality of measuring sections that measure the target component introduced from the centrifugal separation tube by rotation around the second axis of rotation;

wherein a first measuring section of the plurality of measuring sections is connected with one end of the centrifugal separation tube, a measuring section after the first measuring section is connected to a preceding one of the measuring sections so as to introduce the target component into a following one of the measuring sections from the preceding one of the measuring sections, and the volume of the following measuring section is smaller than the volume of the preceding measuring section.

2. The measuring chip according to claim 1, wherein the measuring chip further comprises removing tubes connected to each of the measuring sections; and each extension line of each of the removing tubes intersects with the first axis of rotation.

3. The measuring chip according to claim 1, wherein the first measuring section of the plurality of measuring sections has a measuring section connecting tube that connects the centrifugal separation tube and the measuring section;

each of the measuring sections after the following one of the measuring sections has a measuring section connecting tube that connects the preceding one of the measuring sections and the following measuring section; and an extension line of the measuring section connecting tube of the first measuring section and extension lines of each of the measuring section connecting tubes of the measuring sections after the following one of the measuring sections intersect at the second axis of rotation.

* * * * *